(12) United States Patent
Chase et al.

(10) Patent No.: US 10,307,409 B2
(45) Date of Patent: Jun. 4, 2019

(54) MUSCARINIC COMBINATIONS AND THEIR USE FOR COMBATING HYPOCHOLINERGIC DISORDERS OF THE CENTRAL NERVOUS SYSTEM

(71) Applicant: Chase Pharmaceuticals Corporation, Washington, DC (US)

(72) Inventors: Thomas N. Chase, Washington, DC (US); Kathleen E. Clarence-Smith, Washington, DC (US)

(73) Assignee: Chase Pharmaceuticals Corporation, Washington, DC (US)

( * ) Notice: Subject to any disclaimer, the term of this patent is extended or adjusted under 35 U.S.C. 154(b) by 0 days.

(21) Appl. No.: 15/260,996

(22) Filed: Sep. 9, 2016

(65) Prior Publication Data

US 2016/0375001 A1 Dec. 29, 2016

Related U.S. Application Data

(63) Continuation-in-part of application No. PCT/US2016/020837, filed on Mar. 4, 2016.

(60) Provisional application No. 62/351,382, filed on Jun. 17, 2016, provisional application No. 62/217,081, filed on Sep. 11, 2015, provisional application No. 62/204,021, filed on Aug. 12, 2015, provisional application No. 62/129,289, filed on Mar. 6, 2015.

(51) Int. Cl.
| | |
|---|---|
| *A61K 31/167* | (2006.01) |
| *A61K 31/216* | (2006.01) |
| *A61K 31/439* | (2006.01) |
| *A61K 31/517* | (2006.01) |
| *A61K 31/4178* | (2006.01) |
| *A61K 31/4439* | (2006.01) |
| *A61K 31/4725* | (2006.01) |
| *A61K 31/454* | (2006.01) |
| *A61K 9/70* | (2006.01) |
| *A61K 45/06* | (2006.01) |
| *A61K 9/00* | (2006.01) |
| *A61K 31/166* | (2006.01) |
| *A61K 31/44* | (2006.01) |

(52) U.S. Cl.
CPC ........ *A61K 31/4439* (2013.01); *A61K 9/0056* (2013.01); *A61K 9/7023* (2013.01); *A61K 31/166* (2013.01); *A61K 31/216* (2013.01); *A61K 31/4178* (2013.01); *A61K 31/439* (2013.01); *A61K 31/44* (2013.01); *A61K 31/454* (2013.01); *A61K 31/4725* (2013.01); *A61K 31/517* (2013.01); *A61K 45/06* (2013.01)

(58) Field of Classification Search
CPC .. A61K 31/167; A61K 31/216; A61K 31/439; A61K 31/454; A61K 31/4439; A61K 31/4175; A61K 31/4725
See application file for complete search history.

(56) References Cited

U.S. PATENT DOCUMENTS

| | | | |
|---|---|---|---|
| 5,534,520 A | 7/1996 | Fisher et al. | |
| 2008/0306103 A1 | 12/2008 | Fisher et al. | |
| 2011/0021503 A1* | 1/2011 | Chase | A61K 31/27 514/215 |
| 2011/0071135 A1* | 3/2011 | Chase | A61K 31/166 514/215 |
| 2011/0245294 A1 | 10/2011 | Paborji et al. | |
| 2012/0088785 A1 | 4/2012 | Rich | |
| 2013/0289019 A1 | 10/2013 | Chau | |
| 2015/0231122 A1 | 8/2015 | Clarence-Smith et al. | |

OTHER PUBLICATIONS

International Search Report for PCT/US2016/020837 dated Aug. 8, 2016.
Written Opinion for PCT/US2016/020837 dated Aug. 8, 2016.
Chase et al, "High Dose Donepezil Treatment of Alzheimer's Disease—Preliminary Results from CPC-201 and CPC-212 Trials", http://www.chasepharmaceuticals.com/blog/high-dose-donepezil-treatment-of-alzheimers-disease-poster-presented-on-december-9-by-thomas-n.-chase-md (Dec. 2015).
International Search Report for PCT/US2016/050879 dated Nov. 18, 2016.

* cited by examiner

*Primary Examiner* — Zohreh A Fay
(74) *Attorney, Agent, or Firm* — Roy Issac

(57) ABSTRACT

A combination of a muscarinic cholinergic receptor agonist, a non-anticholinergic antiemetic agent and a non-selective, peripheral anticholinergic agent for the treatment of hypocholinergic disorders of the central nervous system.

3 Claims, No Drawings

MUSCARINIC COMBINATIONS AND THEIR USE FOR COMBATING HYPOCHOLINERGIC DISORDERS OF THE CENTRAL NERVOUS SYSTEM

CROSS-REFERENCE TO RELATED APPLICATIONS

This application claims priority benefit of U.S. Provisional Patent Application Ser. No. 62/217,081, filed Sep. 11, 2015, and U.S. Provisional Patent Application Ser. No. 62/351,382, filed Jun. 17, 2016; the contents of all of which are incorporated herein by reference in their entirety. This application is also a continuation-in-part of PCT/US2016/020837 filed Mar. 4, 2016, which claims priority benefit of U.S. Provisional Patent Application Ser. No. 62/129,289 filed Mar. 6, 2015, and U.S. Provisional Patent Application Ser. No. 62/204,021 filed Aug. 12, 2015; the contents of all of which are incorporated herein by reference in their entirety.

FIELD OF THE INVENTION

The invention pertains to the field of the treatment of hypocholinergic disorders of the central nervous system, in particular of Alzheimer's Disease (AD), Alzheimer type dementia, Parkinson's dementia, Progressive Supranuclear Palsy (PSP), Mild Cognitive Impairment (MCI), Lewy body diseases, Frontotemporal lobe dementia (FTD), Frontotemporal lobar degeneration, Pick's disease, Post-stroke dementia, Vascular dementia, Traumatic brain injury (TBI), Senile dementia, Autism, anorexia nervosa, falls, post-operative delirium, Down Syndrome, chronic neuropathic pain, schizophrenia, Tourette syndrome, Tardive dyskinesia, Huntington's disease, Friedrich's ataxia, Cognitive Impairment associated with Multiple Sclerosis, and other disorders of the nervous system involving a deficit in acetyl-choline neurotransmission; and to a new competitive and safe treatment, a triple combination comprising a cholinergic agonist agent, a non-anticholinergic antiemetic agent and a cholinergic receptor antagonist. More particularly, the invention proposes a combination of a muscarinic agonist which is a Muscarinic Cholinergic Receptor Agonist (MCRA), an antiemetic agent, and a muscarinic antagonist which is a non-selective, peripheral muscarinic receptor antagonist having anticholinergic activity, herein below referred to as non-selective Peripheral Anti-Cholinergic Agent ("nsPAChA").

Definitions

"CNS": Central Nervous System.
"PNS": Peripheral Nervous System.
"Muscarinic type receptors (mAChRs)": Five subtypes of muscarinic receptors, M1 through M5, have been identified.
"MCRA(s)": Cholinergic Receptor Agonist(s) acting on the mAChRs, including orthosteric activators and allosteric activators, in particular both allosteric agonists and positive allosteric modulators, of mAChR subtypes.
"naAEA(s)": non-anticholinergic Anti-Emetic Agent(s).
"Non-anticholinergic" refers to antiemetic medications not primarily regarded as anticholinergic agents; they are entirely devoid of anticholinergic activity or have an extremely low ability to prevent acetylcholine from acting at its cholinergic receptor sites.
"nsPAChA(s)": non-selective, peripheral AntiCholinergic Agent(s) acting on the AChRs which are present in the PNS.
"Non-selective": refers to nsPAChAs, and applies to muscarinic anticholinergic agents exhibiting inhibitory activity on the mAChRs broadly across the various subtypes of muscarinic M-receptors, namely the M1-M5 receptors.
"Peripheral": refers to muscarinic anticholinergic agents and applies to anticholinergics that are largely unable (or have a limited ability) to enter the central nervous system following systemic administration, and thus do not affect brain function to a clinically appreciable degree. These drugs can include both quaternary and tertiary amine anticholinergic agents, especially those having low lipid solubility.
"Anticholinergic therapy": the treatment with an anticholinergic agent of such medical conditions as gastro-intestinal cramping, nausea, retching, vomiting, fecal incontinence, bladder spasms, urinary incontinence, overactive bladder, asthma, motion sickness, muscular spasms, and smooth muscle contractive disorders; or the treatment, if any, with an anticholinergic agent of side effects caused by MCRAs, including, but not limited to gastro-intestinal cramping, nausea, retching, vomiting, fecal incontinence, diarrhea bladder spasms, urinary incontinence, overactive bladder, asthma, motion sickness, muscular spasms, and smooth muscle contractive disorders.
"MTD": maximum (or maximal) tolerated dose, i.e. the highest dose of a drug or treatment that does not cause unacceptable side effects. The maximum tolerated dose is determined in clinical trials by testing increasing doses on different groups of people until the highest dose with acceptable side effects is found (NCI Drug Dictionary).
"CSF": Cerebrospinal Fluid.
"IR": Immediate Release of the active ingredient from a composition.
"ER": Extended Release, including sustained release, controlled release and slow release of the active ingredient from a composition by any administration route, in particular, but not limited to oral and parenteral (including transcutaneous, transdermal, intramuscular, intravenous, and subcutaneous routes).
"AChE": Acetyl Choline esterase
"AChEI(s)": Acetyl Choline Esterase Inhibitor(s).
"Transdermal delivery": administration of drug via the skin which targets, without limitation, skin tissues just under the skin, other tissues or organs under the skin, systemic circulation, and/or the central nervous system.
"Transdermal Therapeutic System (TTS)": administration of drug via transdermal delivery using transdermal drug formulations and transdermal patches incorporating such transdermal drug formulations.
"comprising" means that the compositions and methods include the recited elements, but do not exclude others. "comprising" is inclusive of the terms "consisting of" and "consisting essentially of".
"consisting essentially of" means that the methods and compositions may include additional steps, components or ingredients, but only if the additional steps, components or ingredients do not materially alter the basic and novel characteristics of the claimed methods and compositions. In certain embodiments, "consisting essentially of" means that the subsequently named component(s) is necessarily included but that another unlisted ingredient(s) that does not materially affect the basic and novel properties can also be present. For example, when used to define compositions and methods, "consisting essentially of" means excluding other elements of any essential significance to the combination for the intended use. Thus, for example, a composition consisting essentially of the elements as defined herein would not exclude trace contaminants and pharmaceutically acceptable carriers.

"and/or" is used herein to mean both "and" as well as "or".

"pharmaceutically acceptable salt" means either a pharmaceutically acceptable acid addition salt or a pharmaceutically acceptable base addition salt of a currently disclosed compound that may be administered without any resultant substantial undesirable biological effect(s) or any resultant deleterious interaction(s) with any other component of a pharmaceutical composition in which it may be contained.

"combination therapy" means treating a patient with the triple combination of a cholinergic agonist agent, a non-anticholinergic antiemetic agent and a cholinergic receptor antagonist as a therapeutic platform in rotating, alternating and/or simultaneous treatment schedules. Combination therapy may include a temporal overlap of other therapeutic agents, depending on the clinical course of a given hypocholinergic disease in a subject.

BACKGROUND OF THE INVENTION

Reduced levels of neurotransmitters including acetylcholine occur in dementias of the Alzheimer type. In particular, a deficit in acetylcholine-mediated transmission is thought to contribute to the cognitive and neurobehavioral abnormalities associated with these disorders. Accordingly, drugs known to augment cholinergic transmission in the CNS are the mainstay of current therapy. Other diseases of the nervous system also involve decreased cholinergic transmission and are referred to as "hypocholinergic syndromes and disorders of the Central Nervous System (CNS)". In addition to AD, and AD-type dementia, such diseases, herein below referred to as "hypocholinergic disorders" also include, but are not limited to, Alzheimer's Disease (AD), AD-type dementia, Progressive Supranuclear Palsy (PSP), Mild Cognitive Impairment (MCI), Lewy Body Disease dementia (LBD), Parkinson disease dementia (PDD), post-stroke dementia, vascular dementia, Traumatic Brain Injury (TBI), Senile dementia, Autism, Anorexia Nervosa, falls, post-operative delirium, Down syndrome, Tourette syndrome, tardive dyskinesia, Frontotemporal lobe dementia (FTD), Frontotemporal lobar degeneration, Pick's disease, Huntington's disease, Friedrich's ataxia, chronic neuropathic pain, schizophrenia, Cognitive Impairment associated with Multiple Sclerosis, and other disorders of the nervous system involving a deficit in acetyl-choline neurotransmission. It is well documented that schizophrenic patients experience cognitive disturbances that are not well addressed by current medications (reviewed in Foster et al, 2014).

MCRAs have been reported to dose-dependently improve the cognitive disturbances associated with schizophrenia, but the effect of MCRAs is of limited size and dose-dependent side effects prevent further increases in the MCRA doses.

Acetylcholinesterase inhibitors (AChEIs) are now not only part of the standard of care for patients suffering from a dementia of the Alzheimer type, but are also widely used off-label for various other chronic often progressive hypocholinergic disorders of the nervous system. As a general mechanism of action, AChEIs enhance acetylcholine-mediated neurotransmission. All act in the human CNS to increase and prolong the availability of acetylcholine by inhibiting its degradatory enzyme acetylcholinesterase (AChE). Four AChEIs have been approved by the U.S. FDA for the treatment of dementias of the Alzheimer type: tacrine, donepezil [Aricept®], rivastigmine [Exelon®] and galantamine [Razadyne®]. Rivastigmine has also been approved for the treatment of Parkinson's disease dementia. AChEIs are available in various formulations including immediate release forms such as tablets, capsules and solutions as well as rapid dissolving and extended release forms for oral administration as well as those for parenteral (e.g. transdermal) administration.

Unfortunately, however, none of the available AChEIs offers more than modest clinical benefit for patients suffering from any of the aforementioned dementing disorders, as traditionally administered, even when these medications are administered at their maximum safe and tolerated doses. This is the first problem limiting the success of AChEI therapy of Alzheimer type dementias.

A second problem limiting the success of current AChEI therapy of Alzheimer type dementias is that, even at recommended amounts, AChEIs produce dose limiting adverse reactions, mainly if not exclusively, by over-stimulating peripheral cholinergic receptors of the muscarinic type. As a result, signs and symptoms of untoward gastrointestinal, pulmonary, cardiovascular, urinary, and other systems dysfunction occur. These side effects commonly include, anorexia, nausea, vomiting, diarrhea, abdominal pain, weight loss; increased bronchial secretions, dyspnea, bronchoconstriction and bronchospasm; bradycardia, supraventricular cardiac conduction abnormalities, vasodilation, hypotension, dizziness and syncope; urinary bladder spasm, increased urinary frequency, and incontinence; flushing and diaphoresis; fatigue, headache, lacrymation, miosis, and loss of binocular vision (Physicians' Desk Reference 2008, Thomson PDR, Montvale, N.J.).

Use of AChEIs with a nsPAChA (U.S. Pat. No. 8,404,701, the disclosure of which is incorporated herein by reference in its entirety) or with a non-anticholinergic antiemetic agent has been described (U.S. Pat. No. 8,877,768, the disclosure of which is incorporated herein by reference in its entirety).

Another way to increase the cholinergic transmission in the brain is to stimulate post-synaptic cholinergic receptors by administering an agonist of the muscarinic receptors, but the results were generally disappointing.

In fact, many MCRAs have been studied in the last two decades but, except for cevimeline (EVOXAC®), which is marketed in the U.S.A. for the limited indication of the treatment of symptoms of dry mouth in patients with Sjögren's Syndrome, none of the MCRAs showed a significant activity on the CNS which could be used for the treatment of Alzheimer type dementia or of hypocholinergic disorders.

In a primate study, the muscarinic ligand (5R,6R)-6-(3-butylthio-1,2,5-thiadiazol-4-yl)-1-azabicyclo[3.2.1]octane (BuTAC) exhibited high affinity for muscarinic receptors, but induced vomiting that was mitigated by administration of domperidone (M. B. Andersen et al. Neuropsychopharmacology 2003; 28:1168-1175). No trial in humans with this muscarinc agonist apparently followed this study.

The (E)-N-methoxy-1-(1-methyl-1,2,5,6-tetrahydropyridin-3-yl)methanimine, a non-selective muscarinic acetylcholine receptor partial agonist with cognition-acting properties known as milameline and described in U.S. Pat. No. 6,037,347, the disclosure of which is incorporated herein by reference in its entirety, was investigated for the treatment of Alzheimer's disease. However, the drug, while possessing a pharmacological profile consistent with that of a muscarinic partial agonist, produced central cholinergic action in rats and monkeys at doses slightly higher than those stimulating peripheral cholinergic receptors (Schwarz R D, Callahan M J, Coughenour L L, Dickerson M R, Kinsora J J, Lipinski W J, Raby C A, Spencer C J, Tecle: "Milameline (CI-979/RU35926): a muscarinic receptor agonist with cognition-activating properties: biochemical and in vivo characterization"; J Pharmacol Exp Ther. 1999 November; 291(2):812-22—Schwarz 1999, the disclosure of which is incorporated herein by reference in its entirety). The development of milameline seems to be discontinued.

Similarly, the (3R)—N-methoxyquinuclidine-3-carboximidoyl cyanide hydrochloride known as sabcomeline and described in U.S. Pat. No. 5,278,170, the disclosure of which is incorporated herein by reference in its entirety, is a selective M1 receptor partial agonist that was under development for the treatment of Alzheimer's disease (Loudon J M, Bromidge S M, Brown F, et al.: "SB 202026: a novel muscarinic partial agonist with functional selectivity for M1 receptors"; J Pharmacol Exp Ther. 1997 December; 283(3):1059-68—Louden 1997, the disclosure of which is incorporated herein by reference in its entirety). It was submitted to phase III clinical trials before being discontinued (R & D Focus Drug News, Mar. 8, 2004).

Another MCRA, the 5-[4-(hexylsulfanyl)-1,2,5-thiadiazol-3-yl]-1-methyl-1,2,3,6-tetrahydropyridine, known as tazomeline and described in U.S. Pat. No. 5,041,455, the disclosure of which is incorporated herein by reference in its entirety, acts as a non-selective muscarinic acetylcholine receptor agonist. It was in clinical trials for the treatment of cognitive dysfunction such as that seen in Alzheimer's disease and schizophrenia, but, according to Wikipedia (Sep. 9, 2015), its "development was apparently scrapped for unknown reasons" and no sign of an effective development is known.

A close analog of tazomeline, the 3-(4-hexyloxy-1,2,5-thiadiazol-3-yl)-1-methyl-5,6-dihydro-2H-pyridine known as xanomeline and described in U.S. Pat. No. 5,043,345, the disclosure of which is incorporated herein by reference in its entirety, has been disclosed as a muscarinic acetylcholine receptor agonist with reasonable selectivity for the M1 and M4 subtypes. The efficacy of xanomeline, which stimulates muscarinic receptors in the brain and in the periphery was studied in patients with Alzheimer disease in a 6-month double-blind, placebo-controlled, parallel group trial. Compared to placebo, xanomeline was shown to significantly improve cognitive and behavioral symptoms of Alzheimer disease (Bodick et al, 1997; Shekhar et al, 2008), but also caused dose-dependent unacceptable side effects, including bradycardia, gastro-intestinal distress, excessive salivation, and sweating. Such side effects prevented the use of doses of xanomeline that could achieve maximum anti-dementia efficacy and reflect stimulation of cholinergic receptors outside the brain.

Xanomeline is also described in a transdermally administrable form in U.S. Pat. No. 5,980,933, the disclosure of which is incorporated herein by reference in its entirety, and a clinical experimentation of said preparation was announced. The paper Mirza, N. et al., CNS Drug Review, 9(2): 159-186 (2003) confirmed a phase II clinical trial with transdermal xanomeline, but no specific result appeared in the literature after that date.

A xanomeline fluorinated analog, the 3-[3-(3-(3-fluorophenyl)-2-propyn-1-ylthio)-1,2,5-thiadiazol-4-yl]-1,2,5,6-tetrahydro-1-methylpyridine oxalate, known as EUK 1001, was disclosed by Xiaoping Lei in CN1821243B and considered a promising therapeutic agent for the treatment of AD and age-related memory disorders (Yihui Cui, Dong Wang, Wen Si, Wen Lv, Yan Niu, Xiaoping Lei, Yinhe Hu and Xiaohua Cao: "Enhancement of memory function in aged mice by a novel derivative of xanomeline"; Cell Research; 2008; 18:1151-1153 published online 21 Oct. 2008—Yihui Cui 2008 the disclosure of which is incorporated herein by reference in its entirety). However, no result of clinical trials in human being using EUK1001 has been reported in the literature.

Dose-limiting adverse events attending the use of drugs that stimulate cholinergic transmission, such as xanomeline, appear to primarily reflect the excessive stimulation of peripheral cholinergic receptors, especially those of the muscarinic type (mAChRs), such that in both healthy volunteers and Alzheimer's patients many of these side effects have been reported for xanomeline; in the patient population this led to a discontinuation rate higher than 50% while the effects on cognition were not robust and mainly seen at the highest doses tested (Mirza2003).

As a matter of fact, for the MCRAs tested in clinical trials for the treatment of Alzheimer disease, the milameline maximum tolerated dose was determined as being 2 mg four times per day (J. J. Sramek et al. Life Sciences 1998, 62/3: 195-202);

the xanomeline minimum intolerated dose was reached at 115 mg three times a day, and 100 mg three times a day was defined as the MTD by J. J. Sramek et al. (J Clin Pharmacol 1995; 35:800-806), who also observed that higher xanomeline concentrations appear to be associated with reduced tolerance to the drug; the literature also shows that, in a 6-month double-blind, placebo-controlled, parallel group efficacy study, 59% of patients discontinued treatment after receiving 75 mg xanomeline orally three times daily, mainly because of adverse events, predominantly gastrointestinal (N. R. Mirza et al. CNS Drug Reviews Vol. 9, No. 2, pp. 159-186, 2003).

In conclusion, the development of all of the above MCRAs was discontinued because the results of the studies were disappointing not due to a basic muscarinic inactivity of the products but because said products had limited efficacy at doses that were tolerable in patients, and induced dose-limiting, intolerable adverse effects at higher doses.

In a review published in NEUROLOGY, 49, July 1997, by H. Robert Brashear, MD, of the book "Muscarinic Agonists and the Treatment of Alzheimer Disease" (Edited by Abraham Fisher—R. G. Landes, 1996), the reviewer concluded his comment as follows: "It will be of interest to most clinicians who treat Alzheimer's disease and valuable to chemical researchers, basic neuroscientists, biochemists, and pharmacologists investigating cholinergic dysfunction and therapy". Despite this clear interest and the extensive studies made on a series of compounds during the last two decades, none of the studied compounds became a drug for the treatment this disease for the reasons set forth above.

In addition, MCRAs consisting of allosteric modulators of the $M_1$-muscarinic acetylcholine receptor are extensively studied and are the object of copious patent and scientific literature.

A review by B. J. Melancon, J. C Tarr, J. D. Panarese, M. R. Wood and C. W. Lindsley published in Drug Discovery Today; Volume 18, Numbers 23/24, December 2013, "Allosteric modulation of the $M_1$ muscarinic receptor: improving cognition and a potential treatment for schizophrenia and Alzheimer's disease" (Melancon et al.), the disclosure of which is incorporated herein by reference in its entirety, illustrates the role of the $M_1$ receptor in Alzheimer's disease and in schizophrenia by referring to selected allosteric modulators of the $M_1$ receptor.

This review also reports that positive allosteric modulator MK-7622 entered Phase II clinical trials as an adjunct therapy to AChEIs in patients with AD. This positive allosteric modulator of the $M_1$ receptor, 3-[(1S,2S)-2-hydroxycyclohexyl]-6-[(6-methylpyridin-3-yl)methyl]benzo[h]quinazolin-4(3H)-one, is described in U.S. Pat. No. 8,883,810, the disclosure of which is incorporated herein by reference in its entirety.

The precise causes of vomiting and related gastrointestinal symptoms induced bycholinergic therapy are not known. Presumably, these symptoms reflect cholinergic receptor hyperstimulation attending the administration of muscarinic agonists or of AChEIs.

An improvement in the treatment of Alzheimer type dementia is attained by a combined therapy associating a non-selective, peripheral anticholinergic agent, at a dose of from 20% to 200% the current daily doses, with an AChEI, at a dose up to about 6 times the maximal recommended dose of said AChEI, as disclosed in U.S. Pat. No. 8,404,701, the disclosure of which is herein incorporated by reference in its entirety. By such a treatment, a higher acetylcholinesterase inhibition in the CNS is achieved and greater relief of the symptoms of Alzheimer type dementia is enabled. This result was obtained by successfully inferring that the good dose-response obtained with the AChEIs, i.e. with enzyme inhibitors, would allow an increase of the inhibition of AChE in the CNS with a safe increase of the AChEI dose. Conversely, in the case of the muscarinic receptors, nothing in the literature suggests how to effectively take advantage of the properties of MCRAs. In particular, the literature does not give any indication or suggestion for exploiting the potentiality of said muscarinic agonists in the treatment of disease.

U.S. Pat. No. 8,877,768, the disclosure of which is herein incorporated by reference in its entirety, discloses a combined therapy associating a non-anticholinergic-antiemetic agent, at a dose of from 50% to 300% the current IR daily doses, with an AChEI, at a dose up to 4 times the maximal recommended doses of said AChEI when administered alone. However, the antiemetics, which are non-anticholinergic by definition, do not interfere with both the central and peripheral therapeutic activity of the AChEIs.

U.S. Pat. No. 8,883,810 (see also WO 2010/059773), the contents of which are incorporated herein in their entirety for reference, describing MK-7622, cites the combination of a class of aryl methyl benzoquinazolinone compounds disclosed therein with other drugs to render the administration safer or more effective or to reduce the risk of side effects or toxicity of said aryl methyl benzoquinazolinones. These combinations include anticholinergic drugs but the document does not disclose any non-selective, peripheral anticholinergic drug. On the contrary, it specifically cites biperiden and trihexyphenidyl hydrochloride as anticholinergics, both being central anticholinergic agents for the treatment of the Parkinson's disease. Centrally acting anticholinergics would block the beneficial effects of MCRAs on hypocholinergic disorders of the brain.

Similarly, U.S. Pat. No. 8,853,219, the contents of which are incorporated herein in their entirety for reference, discloses chemical compounds as muscarinic agonists that can be used to treat normal cognitive impairment that accompanies aging, or to treat disorders such as Alzheimer's disease, dementia, autism and schizophrenia; and also discloses their combination with any anticholinergic agent, including those that cross the Blood Brain Barrier (BBB) and also those that, as taught by WO 2009/120277 in the case of the AChEIs, do not cross the BBB.

However, the problem of dose-limiting adverse effects encountered during the clinical trials involving MCRAs, which can be expected to occur with any muscarinic receptor agonist remains unsolved.

SUMMARY OF THE INVENTION

The present inventors have found that the aforementioned observation of J. J. Sramek et al. (J Clin Pharmacol 1995; 35:800-806) concerning the apparently inseparable muscarinic activity/adverse effects relationship may be annulled, while on one side preserving the full therapeutic muscarinic activity of the agonist in the brain and on the other side by eliminating the dose-limiting adverse effects, by combining said muscarinic agonist with a nsPAChA and with a naAEA.

In fact, it has been found that a combination of MCRAs with a naAEA and a nsPAChA surprisingly acts synergistically to attenuate the dose-limiting side effects of MCRAs, thus enabling a safe, greater increase in the MTD of MCRAs and consequent increase in the efficacy of MCRAs, said increase, contrary to what observed by Sramek et al. (J Clin Pharmacol 1995; 35:800-806), is now possible and permits the utilization of the full, real potency of the muscarinic agonist.

In particular, it has been found that an MCRA/antiemetic/nsPAChA combination allows the safe administration of MCRAs doses—for the MCRAs already submitted to clinical investigation—never attained heretofore. In particular, said antiemetic/nsPAChA combination, when concurrently or sequentially administered in combination with a MCRA, is able not only to neutralize the adverse effects that hindered the development of a muscarinic agonist for the treatment of central disorders due to a deficit of acetylcholine in the brain, but also to increase the concentrations of acetylcholine in the CNS.

Thus, by using an MCRA/antiemetic/nsPAChA combination, safe administration of even high doses of a MCRA can be achieved for a patient suffering from hypocholinergic disorders of the central nervous system, such as Alzheimer's disease (AD), AD-type dementia, Progressive Supranuclear Palsy (PSP), Mild Cognitive Impairment (MCI), Lewy Body Disease dementia (LBD), Frontotemporal lobe dementia (FTD), Frontotemporal lobar degeneration, Parkinson disease dementia (PDD), post-stroke dementia, vascular dementia, Traumatic Brain Injury, Senile dementia, Autism, Anorexia Nervosa, Down syndrome, chronic neuropathic pain, Tourette syndrome, tardive dyskinesia, Pick's disease, Huntington's disease, Friedrich's ataxia, falls, post-operative delirium, schizoaffective disorders, schizophrenia, Cognitive Impairment associated with Multiple Sclerosis, and and other disorders of the nervous system involving a deficit in acetyl-choline neurotransmission. The combination allows said MCRA to safely activate the acetylcholine receptors and to improve cognition.

The finding of the present invention represents a further progress in the treatment of hypocholinergic disorders, especially in view of the lack of efficacy of the muscarinic cholinergic receptor agonists at the doses administered to the patients and of the apparently irreducible adverse effects induced by said agonists at the administered doses.

This finding of the present invention eliminates the dose-limit that, in the past, caused the failure of all the clinical trials, thus providing a method for treating Alzheimer type dementia as well as hypocholinergic disorders of the CNS by enabling the full efficacy of MCRAs. The method of the present invention comprises treating a patient in need of such a treatment with a high dose of a nsPAChA, in combination with an antiemetic and a MCRA. This treatment method precludes the onset of MCRA-associated peripheral dose-limiting adverse effects as well as the onset of nsPAChA central adverse effects, because these anticholinergics are substantially peripheral.

Thus, the present invention provides a combination comprising, as Components:
(a) a muscarinic cholinergic receptor agonist (MCRA);
(b) a non-anticholinergic antiemetic agent (naAEA); and
(c) a non-selective peripheral anticholinergic agent (nsPAChA).

The present invention also provides a method of using the above triple combination for the treatment of hypocholinergic disorders in CNS.

In addition, the present invention provides the above combination wherein said Components (b) and (c) are formulated in the same unit form. Herein below, the (b)+(c) fixed-dose combination will also designated as "Component (b/c).

The present invention also provides the above triple combination, wherein said Components (a) and (c) are formulated in the same unit form. Herein below, the (a)+(c) fixed-dose combination will also designated as "Component (a/c)".

Furthermore, the present inventors found that, in order to assure safe treatment of hypocholinergic disorders and sure synergy with the third component of the combination, i.e. the nsPAChA Component (c), the non-anticholinergic antiemetic agent must be administered concurrently with the MCRA from the beginning of the therapeutic treatment of a patient submitted to this cholinergic treatment for the first time. In order to assure said safe treatment, said naAEA and said MCRA are preferably present in said combination as a fixed-dose combination consisting of a pharmaceutical composition wherein said naAEA and said MCRA are formulated in a dosage unit form in admixture with a pharmaceutical carrier.

Thus, the present invention also provides the above combination, wherein said Components (a) and (b) are formulated in the same unit form. Herein below, the (a)+(b) fixed-dose combination will also designated as "Component (a/b)".

According to the present invention, the novel pharmaceutical composition in dosage unit form comprising, as active ingredients, (a) a MCRA; and (b) a naAEA, in admixture with a pharmaceutical carrier or vehicle, is a particularly advantageous embodiment of the present invention.

A further particularly advantageous embodiment is a pharmaceutical composition in dosage unit form comprising as active ingredients:
(a) a MCRA selected from the group consisting of xanomeline and pharmaceutically acceptable salts thereof and MK-7622 and pharmaceutically acceptable salts thereof, at a dose capable of increasing the acetylcholine supply in the CNS of a patient suffering from a hypocholinergic disorder; and (b) a naAEA selected from the group consisting of ondansetron and pharmaceutically acceptable salts and solvates thereof, domperidone and pharmaceutically acceptable salts and solvates thereof, metoclopramide and pharmaceutically acceptable salts and solvates thereof, in an amount of from 50% to 300% the maximum amount contained in the commercial preparations of said naAEA, in admixture with a pharmaceutical carrier, as a preferred Component (a/b) of the combination of the present invention.

The present invention also provides the above combination as a fixed-dose combination wherein said Components (a), (b) and (c) are formulated in the same unit form.

The present invention also provides the addition of an AChEI to the above MCRA/naAEA/nsPAChA combination, thus assuring a maximum supply of acetylcholine to the CNS by the administration of a combination of the four components. Herein below, the fourth AChEI component will also be designated as "Component (d)".

Finally, the present invention provides a kit comprising a combination selected from the group consisting of
(i) a MCRA in a pharmaceutical composition in a dosage unit form wherein said MCRA is in admixture with a pharmaceutical carrier; and
(ii) a fixed-dose combination comprising a nsPAChA and a naAEA in a dosage unit form wherein said combination is in admixture with a pharmaceutical carrier;
(i) a naAEA in a pharmaceutical composition in a dosage unit form wherein said naAEA is in admixture with a pharmaceutical carrier; and
(ii) a fixed-dose combination comprising a MCRA and a nsPAChA in a dosage unit form wherein said MCRA and said nsPAChA are formulated together in admixture with a pharmaceutical carrier;
(i) a nsPAChA in a pharmaceutical composition in a dosage unit form wherein said nsPAChA is in admixture with a pharmaceutical carrier; and
(ii) a fixed dose combination comprising a MCRA and a naAEA in a dosage unit form wherein said MCRA and said naAEA are formulated together in admixture with a pharmaceutical carrier.

The fixed-dose combination consisting of a pharmaceutical composition comprising a MCRA and a naAEA in a dosage unit form wherein said combination is in admixture with a pharmaceutical carrier is a novel entity that is a further object of the present invention.

This kit, which may also contain an AChEI in a pharmaceutical composition in dosage unit form wherein said AChEI is in admixture with a pharmaceutical carrier, can simplify the administration of the above combination to patients suffering from hypocholinergic disorders of the CNS, who are often not sufficiently able to manage multiple packages.

DETAILED DESCRIPTION

The present invention provides a pharmaceutical combination comprising as Components:
(a) a muscarinic receptor agonist selected from the group consisting of muscarinic cholinergic receptor agonists (MCRA);
(b) a naAEA; and
(c) a muscarinic receptor antagonist selected from the group consisting of the non-selective, peripheral anticholinergic agents (nsPAChAs).

According to an embodiment, said pharmaceutical combination comprises as Components:

(a) a MCRA, in a pharmaceutical composition in admixture with a pharmaceutical carrier;
(b) a naAEA, in a pharmaceutical composition in admixture with a pharmaceutical carrier; and
(c) a nsPAChA, in a pharmaceutical composition in admixture with a pharmaceutical carrier.

According to another embodiment, said pharmaceutical combination comprises as Components:
(a) a MCRA, in a pharmaceutical composition in admixture with a pharmaceutical carrier;
(b) a naAEA, in a pharmaceutical composition in admixture with a pharmaceutical carrier; and
(c) a nsPAChA selected from the group consisting of oxybutynin and pharmaceutically acceptable salts thereof, in a pharmaceutical composition consisting of a TTS, in admixture with a pharmaceutical carrier.

According to a particularly advantageous embodiment, said pharmaceutical combination comprises as Components:
(a/b) a pharmaceutical composition in dosage unit form comprising
   (a) a MCRA; and
   (b) a naAEA,
   in admixture with a pharmaceutical carrier; and
(c) a nsPAChA selected from the group consisting of oxybutynin and pharmaceutically acceptable salts thereof, in a pharmaceutical composition consisting of a TTS, in admixture with a pharmaceutical carrier.

A preferred pharmaceutical combination comprises
(a) a MCRA selected form the group consisting of cevimeline and pharmaceutically acceptable salts thereof; milameline and pharmaceutically acceptable salts thereof; xanomeline and pharmaceutically acceptable salts thereof and MK-7622 and pharmaceutically acceptable salts thereof, in a pharmaceutical composition in admixture with a pharmaceutical carrier;
(b) a naAEA selected from the group consisting of ondansetron and pharmaceutically acceptable salts and solvates thereof, domperidone and pharmaceutically acceptable salts and solvates thereof and metoclopramide and pharmaceutically acceptable salts and solvates thereof, in a pharmaceutical composition in admixture with a pharmaceutical carrier; and
(c) a nsPAChA consisting of oxybutynin and pharmaceutically acceptable salts thereof, in a TTS in admixture with a pharmaceutical carrier.

This combination may be used for the treatment of Alzheimer type dementia and more generally for hypocholinergic disorders of the central nervous system, including Parkinson's disease dementia, Lewy Body Dementia, Frontotemporal Lobar Dementia, Mild Cognitive Impairment (MCI), Vascular Dementia, Traumatic Brain Injury, falls, post-operative delirium, Down Syndrome, Anorexia nervosa, and Schizophrenia.

The MCRAs Component (a)

Any MCRA which is able to cross the brain blood barrier of a human in order to stimulate the muscarinic cholinergic receptors in the CNS may be used as Component (a) according to the present invention.

Advantageously, the MCRA used as Component (a) is one of the muscarinic cholinergic agonists that have extensively, but unsuccessfully been investigated in relation to the possibility of using them for the treatment of Alzheimer type dementia, as well as $M_1$ receptor positive allosteric modulators that are believed to be useful in the treatment of this and other diseases involving the muscarinic $M_1$ receptor.

Preferably, said MCRA is selected from the group consisting of
1-methylpiperidine-4-spiro-5'(2'-ethyl-1',4'-thiazoline-3'-one) (AF267) and pharmaceutically acceptable salts and solvates thereof, especially its hydrochloride (AF 267B) described in EP 0711292;
cis-2'-methylspiro {1-azabicyclo[2.2.2]octane-3,5'-[1,3] oxathiolane} described in U.S. Pat. Nos. 4,855,290 and 5,571,918 (cevimeline), and pharmaceutically acceptable salts and solvates thereof, especially its hydrochloride hemihydrate;
3-[3-(3-(3-fluorophenyl)-2-propyn-1-ylthio)-1,2,5-thiadiazol-4-yl]-1,2,5,6-tetrahydro-1-methylpyridine described in CN 1821243B and pharmaceutically acceptable salts and solvates thereof, especially its oxalate (EUK 1001);
(E)-N-methoxy-1-(1-methyl-1,2,5,6-tetrahydropyridin-3-yl)methanimine described in U.S. Pat. No. 6,037,347 (milameline) and pharmaceutically acceptable salts and solvates thereof, especially its hydrochloride;
2-ethyl-8-methyl-2,8-diazaspiro[4.5]decane-1,3-dione described in U.S. Pat. No. 3,056,796 (RS-86) and pharmaceutically acceptable salts and solvates thereof, especially its hydrobromide;
(3R)—N-methoxyquinuclidine-3-carboximidoyl cyanide described in U.S. Pat. No. 5,278,170 (sabcomeline) and pharmaceutically acceptable salts and solvates thereof, especially its hydrochloride;
(3R)-3-(prop-2-yn-1-yloxy)-1-azabicyclo[2.2.2]octane (talsaclidine) described in U.S. Pat. No. 5,286,864, and pharmaceutically acceptable salts and solvates thereof, especially its fumarate;
5-[4-(hexylthio)-1,2,5-thiadiazol-3-yl]-1-methyl-1,2,3,6-tetrahydropyridine described in U.S. Pat. No. 5,041,455 (tazomeline) and pharmaceutically acceptable salts and solvates thereof, especially its hydrochloride;
3-(4-hexyloxy-1,2,5-thiadiazol-3-yl)-1-methyl-5,6-dihydro-2H-pyridine described in U.S. Pat. No. 5,041,455 and EP 0384288 (xanomeline) and pharmaceutically acceptable salts and solvates thereof, especially its oxalate and L-tartrate;
(4-n-butyl-1-[4-(2-methylphenyl)-4-oxo-1-butyl]-piperidine (AC-42) and pharmaceutically acceptable salts and solvates thereof, especially its hydrogen chloride;
(5R,6R)-6-(3-butylthio-1,2,5-thiadiazol-4-yl)-1-azabicyclo[3.2.1]octane (BuTAC), mentioned above, and pharmaceutically acceptable salts thereof, described for example as squalene synthetase inhibitor in U.S. Pat. No. 5,750,538 and anti-hypercholesterolemic agent;
1-[1'-(2-methylbenzyl)-1,4'-bipiperidin-4-yl]-1,3-dihydro-2H-benzimidazol-2-one (TBPB) and pharmaceutically acceptable salts and solvates thereof;
4-Fluoro-6-methyl-1-[1-(tetrahydro-2H-pyran-4-yl)-4-piperidinyl]-1,3-dihydro-2H-benzimidazol-2-one and pharmaceutically acceptable salts and solvates thereof, described in WO 2007/036715;
5-Fluoro-6-methyl-1-[1-(tetrahydro-2H-pyran-4-yl)-4-piperidinyl]-1,3-dihydro-2H-benzimidazol-2-one and pharmaceutically acceptable salts and solvates thereof, described in WO 2007/036718 and U.S. Pat. No. 8,288,412;
4-(R)-ethyl-3-(2-methylbenzamido)-1,4'-bipiperidine-1'-carboxylate and pharmaceutically acceptable salts and solvates thereof, described in WO 2010/096703;

ethyl 3-[(3-exo)-(2-benzamidoethyl)amino]-8-azabicyclo[3.2.1]octane-8-carboxylate and pharmaceutically acceptable salts and solvates thereof, described in U.S. Pat. No. 8,697,691;

5-(3-ethyl-1,2,4-oxadiazol-5-yl)-1,4,5,6-tetrahydropyrimidine (MCD-386) and pharmaceutically acceptable salts and solvates thereof, described in U.S. Pat. No. 8,853,219;

3-Methyl-5-(piperidin-3-yl)-1,2,4-oxadiazole, its enantiomers and pharmaceutically acceptable salts and solvates thereof, described in U.S. Pat. No. 8,853,219; and 3-[(1S,2S)-2-hydroxycyclohexyl]-6-[(6-methylpyridin-3-yl)methyl]benzo[h]quinazolin-4(3H)-one (MK-7622), described in U.S. Pat. No. 8,883,810 and pharmaceutically acceptable salts and solvates thereof, especially the fumarate, the methanesulfonate or the hydrochloride.

The amount of the MCRA Component (a) of the combination, i.e. a single MCRA dose, may vary according to intrinsic muscarinic cholinergic receptor potency of said component and is present in an amount from 1-times to up to six times the maximum amount contained in the commercial products or of the maximal, single MCRA dose administered during the clinical trials of each MCRA, that is considered to be equivalent to the Maximum Tolerated Dose as determined during the clinical trials. Advantageously, said dose is from 1.2-times to 4-times and even from 1.2-times to 6-times higher than the maximum amount contained in the commercial products or of the maximal, single MCRA dose administered during the clinical trials.

In general, and particularly when data from commercial products or clinical trials is not available, for an individual patient, the MCRA Component (a) in the combination of the present invention is present in an amount from 1-times to up to 6-times greater than the amount of MCRA Component (a) that first induces vomiting and/or diarrhea in said patient when the MCRA Component (a) is administered alone.

For most patients, the above criteria will result in the MCRA Component (a) in the combination of the present invention being present in an amount from 0.5 mg to 1500 mg.

In particular, the maximum dose/unit form approved for cevimeline (as hydrochloride hemihydrate) is 30 mg, to be administered three times per day.

However, as set forth above, cevimeline is the sole MCRA approved for a pharmacological treatment, said treatment having no relation with any form of dementia.

Among the other MCRAs tested in clinical trials for the treatment of Alzheimer disease, in view of the aforementioned Mirza et al 2003 (CNS Drug Reviews Vol. 9, No. 2, pp. 159-186) paper showing that, in the context of the present invention the maximum tolerated dose of said xanomeline is considered as being 75 mg three times per day, i.e. 225 mg/day.

Thus, for example, in the combination of the present invention cevimeline, as hydrochloride hemihydrate, is present in an amount of from 30 mg to 180 mg, advantageously from more than 30 mg to 180 mg, preferably from 36 mg to 180 mg; milameline, as hydrochloride, is present in an amount of from 2 mg to 12 mg, preferably from 2.4 mg to 12 mg, normally from more than 2 mg to 8 mg; xanomeline, as free base, as oxalate or as L-tartrate, is present in an amount of from 75 mg to 450 mg, preferably from 90 mg to 450 mg, normally from more than 75 mg to 180 mg; and MK-7622, especially as hydrochloride, methanesulfonate or fumarate, is present in an amount of from 5 mg to 270 mg, advantageously from more than 5 mg to 270 mg, normally from 15 mg to 225 mg. For the administration for the treatment of a hypocholinergic disorder in a patient, each MCRA is formulated in a pharmaceutical composition in dosage unit form in admixture with a pharmaceutical carrier or vehicle.

In the combination of the present invention, xanomeline may be present in a pharmaceutical composition in dosage unit form, in admixture with a pharmaceutical carrier or vehicle in a TTS formulation, in particular in a patch for transdermal administration. Advantageously, xanomeline is released from a patch in an amount giving xanomeline plasma concentrations of from 15.572 ng/ml to 78.6 ng/ml.

According to the present invention, the safe daily dose of said MCRA may be up to six times the average maximal tolerated dose of said MCRA determined in its clinical trials when used alone, thanks to the competitive action of the MCRA and of the synergistically acting naAEA/naPAChA combination. Normally, it is from 1 times to 6 times, advantageously from 1.2 times to 6 times said maximal tolerated MCRA dose or from 1 times to 6 times, advantageously from 1.2 times to 6 times the maximal daily dose of each MCRA, as previously administered alone to patients during the respective clinical trials.

In particular, using the combination of the present invention, the daily dose of cevimeline, as hydrochloride hemihydrate, is in general from 90 mg to 540 mg, advantageously from more than 90 mg to 540 mg, preferably from 108 mg to 540 mg, normally from 108 mg to 360 mg; the daily dose of milameline, as hydrochloride, in general is from 8 mg to 48 mg, advantageously from more than 8 mg to 48 mg, preferably from 9.6 mg to 48 mg, normally from 9.6 mg to 32 mg; the daily dose of xanomeline, as oxalate or L-tartrate, in general is from 300 mg to 1350 mg, advantageously from more than 300 mg to 1350 mg or from 337.5 mg to 1350 mg, normally from 337.5 mg to 900 mg; and the daily dose of MK-7622, as hydrochloride, fumarate or methanesulfonate, in general is from 5 mg to 270 mg, advantageously from more than 5 mg to 270 mg or preferably from 6 mg to 270 mg, normally from 15 mg to 225 mg.

The naAEAs Component (b)

Antiemetic medications commonly used to treat emesis, and not primarily regarded as anticholinergic agents, that are entirely devoid of anticholinergic activity or have an extremely low ability to prevent acetylcholine from acting at its cholinergic receptor sites in the brain may be used as Component (b) of the pharmaceutical combination of the present invention.

Preferably, said Component (b) is a non-anticholinergic antiemetic agent selected from the group consisting of (b1) 5HT3-antagonists, (b2) DA-antagonists, (b3) H1-antagonists, (b4) cannabinoids, and (b5) NK1-antagonists.

Typical non-anticholinergic antiemetic agents are
  5-HT3 receptor antagonists (5HT3-antagonists), such as 9-methyl-3-[(2-methyl-1H-imidazol-1-yl)methyl]-1,2,3,9-tetrahydrocarbazol-4-one (ondansetron) and pharmaceutically acceptable salts and solvates thereof, in particular its hydrochloride dihydrate, described in EP 191562; 3S-ondansetron; 3R-onsdansetron; (3R)-10-oxo-8-azatricyclo[5.3.1.03,8]undec-5-yl 1H-indole-3-carboxylate (dolasetron) and pharmaceutically acceptable salts and solvates thereof, in particular its monomethanesulfonate (mesylate or mesilate) monohydrate, described in EP 266730; 1-methyl-N-(9-methyl-9-azabicyclo[3.3.1]non-3-yl)-indazole-3-carboxamide (granisetron) and pharmaceutically acceptable salts and solvates thereof, in particular its hydrochloride, described in EP 200444; [(1S,5S)-8-methyl-8-azabicyclo[3.2.1]oct-3-yl]1H-indole-3-carboxylate (tropisetron) and pharmaceutically acceptable salts and solvates thereof, in particular its monohydrochloride, described in U.S. Pat. No. 4,789,673; 1-phenylmethyl-2-piperazinyl-1H-benzimidazole (lerisetron) and pharmaceutically acceptable salts and solvates thereof, in particular its hydrochloride, described in EP 512939; (R)-5-[(1-methyl-3-indolyl)carbonyl]-4,5,6,7-tetrahydro-1H-benzimidazole (ramosetron) and pharmaceutically acceptable salts and solvates thereof, in particular its hydrochloride, described in U.S. Pat. No. 5,344,927; (3aR)-2-[(3S)-1-azabicyclo[2.2.2]oct-3-yl]-2,3,3a,4,5,6-hexahydro-1H-benz[de]isoquinolin-1-one (palonosetron) and pharmaceutically acceptable salts and solvates thereof, in particular its hydrochloride, described in U.S. Pat. No. 5,202,333; 2,3,4,5-tetrahydro-5-methyl-2-[(5-methyl-1H-imidazol-4-yl)methyl]-1H-pyrido[4,3-b]indol-1-one (alosetron) and pharmaceutically acceptable salts and solvates thereof, in particular its hydrochloride, described in U.S. Pat. No. 5,360,800; and (±)-6-chloro-,3,4-dihydro-4-methyl-3-oxo-N-(quinuclidinyl)-2H-1,4-benzoxazine-8-carboxamide (azasetron) and pharmaceutically acceptable salts and solvates thereof, in particular its hydrochloride, described in U.S. Pat. No. 4,892,872; which are known to be serotonin receptors blockers in the central nervous system and gastrointestinal tract and have been proposed for use to treat post-operative and cytotoxic drug nausea and vomiting;

dopamine antagonists ("DA-antagonists"), such as 5-chloro-1-(1-[3-(2-oxo-2,3-dihydro-1H-benzo[d]imidazol-1-yl)propyl]piperidin-4-yl)-1H-benzo[d]imidazol-2(3H)-one (domperidone) and pharmaceutically acceptable salts and solvates thereof, particularly its maleate; 1-[1-[4-(4-fluorophenyl)-4-oxo-butyl]-3,6-dihydro-2H-pyridin-4-yl]-3H-benzoimidazol-2-one (droperidol); 4-[4-(4-chlorophenyl)-4-hydroxy-1-piperidyl]-1-(4-fluorophenyl)-butan-1-one (haloperidol); 3-(2-chloro-10H-phenothiazin-10-yl)-N,N-dimethyl-propan-1-amine (chlorpromazine) and pharmaceutically acceptable salts and solvates thereof, particularly its hydrochloride; 2-chloro-10-[3-(4-methyl-1-piperazinyl)propyl]-10H-phenothiazine (prochlorperazine), and pharmaceutically acceptable salts and solvates thereof, particularly its dimaleate, dimesylate or 1,2-ethanedisulfonate (1:1) (edisilate); dimethyl[1-(10H-phenothiazin-10-yl)propan-2-yl]amine (promethazine) and pharmaceutically acceptable salts and solvates thereof, particularly its hydrochloride; 4-aminosalicylamide and benzamide derivatives like 4-amino-5-chloro-N-[2-(diethylamino)ethyl]-2-methoxybenzamide (metoclopramide) and pharmaceutically acceptable salts and solvates thereof such as its monohydrochloride monohydrate; 4-amino-5-bromo-N-[2-(diethylamino)ethyl]-2-methoxybenzamide (bromopride) and pharmaceutically acceptable salts and solvates thereof, particularly its monohydrochloride and its dihydrochloride monohydrate; 4-amino-N-(1-benzylpiperidin-4-yl)-5-chloro-2-methoxybenzamide (clebopride) and pharmaceutically acceptable salts and solvates thereof, particularly its malate or its hydrochloride monohydrate; N-[(1-allylpyrrolidin-2-yl)methyl]-6-methoxy-1H-benzo[d][1,2,3]triazole-5-carboxamide (alizapride) and pharmaceutically acceptable salts and solvates thereof, particularly its hydrochloride; (L)-2-methoxy-N-((1-propylpyrrolidin-2-yl)methyl)-5-sulfamoylbenzamide (levosulpiride); N-{[4-(2-dimethylaminoethoxy)phenyl]methyl}-3,4,5-trimethoxy-benzamide (trimethobenzamide) and pharmaceutically acceptable salts and solvates thereof, particularly its hydrochloride;

which act in the brain and especially at the chemoreceptor trigger zone and are known to be used to treat nausea and vomiting associated with neoplastic disease, radiation sickness, opioids, cytotoxic drugs and general anesthetics;

H1 histamine receptor antagonists ("H1-antagonists"), such as 1-[(4-chlorophenyl)-phenyl-methyl]-4-[(3-methylphenyl)methyl]piperazine (meclizine or meclozine) and pharmaceutically acceptable salts and solvates thereof, particularly its dihydrochloride monohydrate; dimethyl[1-(10H-phenothiazin-10-yl)propan-2-yl]amine (promethazine) and pharmaceutically acceptable salts and solvates thereof, particularly its hydrochloride; 3-(2-chloro-10H-phenothiazin-10-yl)-N,N-dimethyl-propan-1-amine (chlorpromazine) or a salt thereof, particularly its hydrochloride; 2-chloro-10-[3-(4-methyl-1-piperazinyl)propyl]-10H-phenothiazine (prochlorperazine) and pharmaceutically acceptable salts and solvates thereof, particularly its dimaleate, dimesylate or 1,2-ethanedisulfonate (1:1) (edisilate); and 2-(2-{4-[(4-chlorophenyl)(phenyl)methyl]piperazin-1-yl}ethoxy)ethanol (hydroxyzine) and pharmaceutically acceptable salts and solvates thereof such as its hydrochloride or 1,1'-methylene-bis (2-hydroxy-3-naphthalenecarboxylic acid salt (pamoate), which are known to be effective in many conditions, including motion sickness and severe morning sickness in pregnancy;

cannabinoid receptor agonists ("cannabinoids"), such as cannabis; (6aR-trans)-6a,7,8,10a-tetrahydro-6,6,9-trimethyl-3-pentyl-6H-dibenzo[b,d]pyran-1-ol (dronabinol); (6aR,10aR)-rel-3-(1,1-dimethylheptyl)-6,6a,7,8,10,10a-hexahydro-1-hydroxy,6,6-dimethyl-9H-dibenzo[b,d]pyran-9-one (nabilone); and (−)-cis-3-[2-hydroxy-4-(1,1-dimethylheptyl)-phenyl]-trans-4-(3-hydroxypropyl)cyclohexanol (CP 55,940);

which are known to be used in patients with cachexia and cytotoxic nausea and vomiting; and antagonists of the neurokinin 1 receptor (NK1-antagonists) such as 5-[[(2R,3S)-2-[(1R)-1-[3,5-bis(trifluoromethyl)phenyl]ethoxy]-3-(4-fluorophenyl)-4-morpholinyl]methyl]-1,2-dihydro-3H-1,2,4-triazol-3-one (aprepitant); (2S,4S)-4-(4-Acetyl-1-piperazinyl)-N-[(1R)-1-[3,5-bis(trifluoromethyl)phenyl]ethyl]-2-(4-fluoro-2-methylphenyl)-N-methyl-1-piperidinecarboxamide (casopitant); 2-[3,5-bis(trifluoromethyl)phenyl]-N,2-dimethyl-N-[4-(2-methylphenyl)-6-(4-methyl-1-piperazinyl)-3-pyridinyl]propanamide (netupitant) described in U.S. Pat. No. 6,297,375, 6,719,996 and 6,593,417; the disclosures of which are incorporated herein in their entirety; and (5S,8S)-8-({(1R)-1-[3,5-bis(trifluoromethyl)phenyl]ethoxy}methyl)-8-phenyl-1,7-diazaspiro[4.5]decan-2-one (rolapitant), described in U.S. Pat. No. 7,049,320 and, for an injectable form thereof, in U.S. Pat. No. 9,101,615; the disclosures of which are incorporated herein in their entirety;

which are known to be neurokinine-1 receptors blockers in both the central and peripheral nervous system and have been proposed for use to treat cytotoxic drug nausea and vomiting.

Advantageous naAEAs are the compounds available in drugs for current antiemetic therapy, in particular, alosetron hydrochloride, available at the oral dose/unit form (in alosetron) of 0.5-1 mg;

azasetron hydrochloride or mesilate monohydrate, available at the oral or i.v. dose/unit form of 10 mg;

dolasetron mesylate monohydrate, available at the oral dose/unit form (in dolasetron) of 50-100 mg;

granisetron hydrochloride, available at the oral dose (in granisetron) of 1-2 mg or in a 52 $cm^2$ transdermal patch containing 34.3 mg of granisetron releasing 3.1 mg of granisetron per 24 hours (herein below indicated as 23.1 mg/24 h";

ondansetron hydrochloride dihydrate, available at the oral dose (in ondansetron) of 4-8 mg;

palonosetron hydrochloride, available at a the oral dose (in palonosetron) of 0.5 mg and i.v. dose (in palonosetron) of 0.25 mg;

tropisetron hydrochloride, available at the oral dose (in tropisetron) of 5 mg;

domperidone, available at the dose of 10 mg;

haloperidol, available at the oral dose of 1-10 mg;

chlorpromazine hydrochloride, available at the oral dose (in chlorpromazine) of 25-100 mg;

prochlorperazinedimaleate, available at the oral dose of 5 mg;

metoclopramide hydrochloride, available dihydrate, at the oral dose (in metoclopramide) of 10 mg;

bromopride dihydrochloride monohydrate, available at the oral dose (in bromopride) of 10 mg;

clebopride malate (1:1), available at a oral dose (in clebopride) of 1 mg;

levosulpiride, at the oral dose of 25-100 mg;

alizapride hydrochloride, available at the oral dose (in alizapride) of 50 mg;

trimethobenzamide hydrochloride, available at the oral dose (in trimethobenzamide) of 100 mg meclizine (also called meclozine), available at the oral dose of 12.5-50 mg;

promethazine hydrochloride, available at the oral dose (in promethazine) of 25 mg;

dronabinol, available at the oral dose of 0.5-1 mg;

aprepitant, available at the oral dose of 40-125 mg;

netupitant, available at the oral dose of 300 mg; and casopitant, at the oral dose of 50 mg;

rolapitant, available at the oral dose of 60 mg;

the palonosetron-0.5 mg/netupitant-300 mg oral fixed-dose combination.

In the pharmaceutical combination to improve the treatment of human dementias of the Alzheimer type according to the present invention, the non-anticholinergic antiemetic agent Component (b) is formulated in a pharmaceutical composition in admixture with a pharmaceutical carrier to be administered in combination with the MCRA Component (a), and the nsPAChA Component (c).

The amount of the MCRA Component (a), sufficient to maximally alleviate disease-associated cognitive and other neurobehavioral symptoms; is illustrated in the above "The MCRAs" section.

The Component (b) is advantageously selected from the group consisting of alosetron and pharmaceutically acceptable salts and solvates thereof, especially its hydrochloride; azasetron and pharmaceutically acceptable salts and solvates thereof, especially its hydrochloride; ondansetron and pharmaceutically acceptable salts and solvates thereof, especially its monohydrochloride dihydrate; granisetron and pharmaceutically acceptable salts and solvates thereof, especially its hydrochloride; dolasetron and pharmaceutically acceptable salts and solvates thereof, especially its monomethanesulfonate monohydrate, ramosetron and pharmaceutically acceptable salts and solvates thereof, especially its hydrochloride; tropisetron and pharmaceutically acceptable salts and solvates thereof, especially its hydrochloride; palonosetron and pharmaceutically acceptable salts and solvates thereof, especially its hydrochloride; domperidone and pharmaceutically acceptable salts and solvates thereof, especially its maleate; chlorpromazine and pharmaceutically acceptable salts and solvates thereof, especially its hydrochloride; prochlorperazine and its salts and solvates, especially its dimaleate and dimesylate; promethazine and pharmaceutically acceptable salts and solvates thereof, especially its hydrochloride; metoclopramide and pharmaceutically acceptable salts and solvates thereof, especially its hydrochloride monohydrate; bromopride and pharmaceutically acceptable salts and solvates thereof, especially its monohydrochloride or the dihydrochloride monohydrate; alizapride and pharmaceutically acceptable salts and solvates thereof, especially its hydrochloride; clebopride and pharmaceutically acceptable salts and solvates thereof, especially its malate and the hydrochloride monohydrate; meclizine (meclozine) and pharmaceutically acceptable salts and solvates thereof, especially its hydrochloride monohydrate; promethazine and pharmaceutically acceptable salts and solvates thereof, especially its hydrochloride; chlorpromazine and pharmaceutically acceptable salts and solvates thereof, especially its hydrochloride; prochlorperazine and pharmaceutically acceptable salts and solvates thereof, especially its dimaleate, its dimesylate and its the 1,2-ethanedisulfonate (1:1) (edisilate); hydroxyzine and pharmaceutically acceptable salts and solvates thereof such as the dihydrochloride or the 1,1'-methylene bis(2-hydroxy-3-naphthalenecarboxylic acid (pamoate); dronabinol; nabilone; aprepitant; netupitant, rolapitant; and casopitant.

In the combination of the present invention, the non-anticholinergic antiemetic agent, Component (b) is present in an amount of from 50% to 600%, normally 50% to 300%, of the amount of the said non-anticholinergic antiemetic agent contained as a sole active ingredient in the currently used brand or generic drugs. Each of said typical non-anticholinergic antiemetic agents is present, in admixture with a pharmaceutical carrier or vehicle, in a pharmaceutical composition in dosage unit form, as Component (b), in an amount ranging from 50% of the minimum amount to 600%, and in some cases beyond 600%, advantageously from 50% to 300%, normally from 100% to 300%, of the maximum amount of said typical non-anticholinergic antiemetic agent contained in the corresponding, currently used generic or brand drug for its antiemetic indication in IR form. Advantageously, the currently used brand or generic drugs containing the maximum amount of said naAEA may be used as Component (b) of the combination of the present invention.

Advantageous naAEA in said Component (b) is selected from the group consisting of alosetron and pharmaceutically acceptable salts and solvates thereof, in particular the hydrochloride, in an amount (in alosetron) of from 0.25 mg to 6 mg; azasetron and pharmaceutically acceptable salts and solvates thereof, in particular the hydrochloride, in an amount (in azasetron) of from 5 mg to 60 mg; dolasetron and pharmaceutically acceptable salts and solvates thereof, in particular the mesylate, in an amount (in dolasetron) of from 25 mg to 600 mg; granisetron and pharmaceutically acceptable salts and solvates thereof, in particular the hydrochloride, in an amount (in granisetron) of from 0.5 mg to 6 mg; ondansetron and pharmaceutically acceptable salts and solvates thereof, in particular the hydrochloride dihydrate, in an amount (in ondansetron) of from 2 mg to 64 mg; palonosetron and pharmaceutically acceptable salts and solvated thereof, in particular its hydrochloride, in an amount (in palonosetron) of from 0.25 mg to 3 mg; ramosetron and pharmaceutically acceptable salts and solvates thereof, in particular its hydrochloride, in an amount (in ramosetron) of from 0.0125 mg to 0.3 mg; tropisetron and pharmaceutically acceptable salts and solvates thereof, in particular the hydrochloride, in an amount of from 2.5 mg to 30 mg; domperidone and pharmaceutically acceptable salts and solvates thereof, in an amount (in domperidone) of from 5 mg to 60 mg; haloperidol, in an amount of from 0.5 mg to 60 mg; chlorpromazine and pharmaceutically acceptable salts and solvates thereof, in particular the hydrochloride, in an amount (in chlorpromazine) of from 12.5 mg to 600 mg; prochlorperazine and pharmaceutically acceptable salts and solvates thereof, in particular the dimaleate, in an amount (in prochlorperazine) of from 2.5 mg to 30 mg; metoclopramide and pharmaceutically acceptable salts and solvates thereof, in particular the monohydrochloride monohydrate, in an amount (in metoclopramide) of from 5 mg to 60 mg; bromopride and pharmaceutically acceptable salts and solvates, in particular the monohydrochloride and the dihydrochloride monohydrate, in an amount (in bromopride) of from 5 mg to 60 mg; clebopride and pharmaceutically acceptable salts and solvates thereof, in particular the hydrogen malate and the hydrochloride monohydrate, in an amount (in clebopride) of from 0.25 mg to 3 mg; levosulpiride, in an amount of from 12.5 mg to 600 mg; alizapride and pharmaceutically acceptable salts thereof, in particular the hydrochloride, in an amount (in alizapride) of from 25 mg to 300 mg; trimethobenzamide and pharmaceutically acceptable salts thereof such as the monohydrochloride, in an amount (in trimethobenzamide) of from 50 mg to 600 mg; meclizine (also called meclozine) and pharmaceutically acceptable salts and solvates thereof, in an amount (in meclizine) of from 6.25 mg to 300 mg; promethazine and pharmaceutically acceptable salts and solvates thereof, in particular the hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant, in an amount of from 25 mg to 300 mg; in a pharmaceutical composition in admixture with a pharmaceutical carrier.

According to an embodiment, the non-anticholinergic antiemetic is present, in an IR unit form, in an amount ranging from 50% to 200% of the maximum amount of said antiemetic agent contained in the currently administered IR dosage unit forms for the treatment of the above-cited disorders or, in an ER unit form, in an amount ranging from 75% to 300% of the maximum amount of said antiemetic agent contained in the currently administered IR dosage unit forms for the treatment of the above-cited disorders.

For example, according to this embodiment, among the advantageous non-anticholinergic antiemetic agents used as Component (b), in said composition ondansetron or a pharmaceutically acceptable salt or solvate thereof, in particular its hydrochloride dihydrate, is present in an amount (in ondansetron) of from 4 mg to 16 mg per dosage unit in an IR unit form or in an amount of from 6 mg to 48 mg, preferably from 16 mg to 32 mg, in an ER unit form; alosetron or a pharmaceutically acceptable salt thereof, in particular its hydrochloride, is present in an amount (in alosetron) of from 0.5 mg to 2 mg per dosage unit in an IR unit form or in an amount of from 0.75 mg to 3 mg, in an ER unit form; azasetron or a pharmaceutically acceptable salt thereof, in particular its hydrochloride, is present in an amount of from 5 mg to 20 mg per dosage unit in an IR unit form or in an amount of from 7.5 mg to 30 mg, preferably from 10 mg to 30 mg, in an ER unit form; ramosetron or a pharmaceutically acceptable salts thereof, in particular its hydrochloride, is present in an amount (in ramosetron) of from 0.025 mg to 0.1 mg per dosage unit in an IR unit form or in an amount of from 0.0375 mg to 0.3 mg, preferably from 0.05 mg to 0.3 mg, in an ER unit form; tropisetron or a pharmaceutically acceptable salt thereof, in particular its hydrochloride, is present in an amount (in tropisetron) of from 2.5 mg to 10 mg per dosage unit in an IR unit form or in an amount of from 3.75 mg to 15 mg, preferably from 5 mg to 15 mg, in an ER unit form; granisetron or a pharmaceutically acceptable salt thereof, in particular its hydrochloride, is present in an amount (in granisetron) of from 1 mg to 4 mg per dosage unit in an IR unit form or in an amount of from 1.5 mg to 6 mg, in an ER unit form; dolasetron, or a pharmaceutically acceptable salt thereof, in particular its mesilate, is present in an amount (in dolasetron) of from 50 mg to 200 mg per dosage unit in an IR unit form or in an amount of from 75 mg to 300 mg, in an ER unit form; palonosetron, or a pharmaceutically acceptable salt thereof, in particular its hydrochloride, is present (a) in an amount (in palonosetron) of from 0.25 mg to 1 mg in an IR dosage unit form or from 0.375 mg to 1.5 mg in an ER dosage unit form, or (b) in an amount (in palonosetron) of from 0.25 mg to 12 mg, in a fixed-dose combination with netupitant, in an amount of from 200 mg to 600 mg, said fixed-dose combination being in an IR dosage unit form; rolapitant, in an amount of form 30 mg to 120 mg, in an IR dosage unit form or in an amount of from 45 mg to 180 mg in an ER dosage unit form; domperidone or a pharmaceutically acceptable salt thereof, in particular its maleate, is present in an amount (in domperidone) of from 5 mg to 20 mg per dosage unit in an IR unit form or in an amount of from 7.5 mg to 30 mg, preferably from 10 mg to 30 mg, in an ER unit form; metoclopramide or a pharmaceutically acceptable salt or solvate thereof, in particular its monohydrochloride monohydrate, is present in an amount (in metoclopramide) of from 5 mg to 20 mg per dosage unit in an IR unit form or in an amount of from 7.5 mg to 30 mg, preferably from 10 mg to 30 mg, in an ER unit form; alizapride or a pharmaceutically acceptable salt thereof, in particular its hydrochloride, is present in an amount (in alizapride) of from 25 mg to 100 mg per dosage unit in an IR unit form or in an amount of from 37.5 mg to 300 mg, preferably from 100 mg to 300 mg, in an ER unit form; meclizine or a pharmaceutically acceptable salt thereof, in particular its hydrochloride is present in an amount (in meclizine) of from 25 mg to 100 mg per dosage unit in an IR unit form or in an amount of from 37.5 mg to 150 mg, preferably from 50 mg to 150 mg, in an ER unit form; chlorpromazine or a pharmaceutically acceptable salt thereof, in particular its hydrochloride is present in an amount (in chlorpromazine) of from 50 mg to 200 mg per dosage unit in an IR unit form or in an amount of from 75 mg to 300 mg, preferably from 100 mg to 300 mg, in an ER unit form; prochlorperazine or a pharmaceutically acceptable salt thereof, in particular its maleate is present in an amount (in prochlorperazine) of from 2.5 mg to 10 mg per dosage unit in an IR unit form or in an amount of from 3.75 mg to 15 mg, preferably from 5 mg to 15 mg, in an ER unit form; dronabinol is present in an amount of from 5 mg to 20 mg per dosage unit in an IR unit form or in an amount of from 7.5 mg to 30 mg, preferably from 10 mg to 30 mg, in an ER unit form; nabilone is present in an amount of from 0.5 mg to 2 mg per dosage unit in an IR unit form or in an amount of from 0.75 mg to 3 mg per dosage unit in an ER unit form; aprepitant is present in an amount of from 62.5 mg to 250 mg per dosage unit in an IR unit form or in an amount of from 93.75 mg to 325 mg, preferably from 125 mg to 325 mg, in an ER unit form; netupitant is present in an amount of from 150 mg to 600 mg, in an IR unit form or in an amount of from 225 to 900 mg, preferably from 300 mg to 900 mg, in an ER unit form; rolapitant, in an amount of form 30 mg to 120 mg, in an IR unit form or in an amount of from 45 mg to 180 mg, preferably from 60 mg to 180 mg, in an ER unit form; and casopitant is present in an amount of from 25 mg to 100 mg per dosage unit in an IR unit form or in an amount of from 37.5 mg to 150, preferably from 50 mg to 150 mg, in an ER unit form, in admixture with a pharmaceutical composition in dosage unit form.

Preferred Component (b) is a pharmaceutical composition in dosage unit form comprising a non-anticholinergic antiemetic agent selected from the group consisting of ondansetron and pharmaceutically acceptable salts and solvates thereof, in an amount (in ondansetron) of from 8 mg to 24 mg; granisetron and pharmaceutically acceptable salts and solvates thereof, in an amount (in granisetron) of from 1 mg to 3 mg; domperidone and pharmaceutically acceptable salts and solvates thereof, in an amount (in domperidone) of from 10 mg to 30 mg; metoclopramide and pharmaceutically acceptable salts and solvates thereof, in an amount (in metoclopramide) of from 10 mg to 30 mg; dronabinol, in an amount of from 10 mg to 30 mg; nabilone, in an amount of from 1 mg to 3 mg; aprepitant, in an amount of from 125 mg to 375 mg; netupitant, in an amount of from 300 mg to 900 mg; rolapitant, in an amount of form 60 mg to 180 mg; and casopitant, in an amount of from 50 mg to 150 mg, in admixture with a pharmaceutical carrier.

Ondansetron may also be used as formulated in a patch, for example as described by Farsiya Fathima et al. in Research in J. Pharm. And Tech. 4,4(5), May 2011, 806-814: "Formulation and Evaluation of Matrix-Type Transdermal Delivery System of Ondansetron Hydrochloride Using Solvent Casting Technique", or by Cho, J., Van Duong, A., Nguyen, L. T. T. et al. in Journal of Pharmaceutical Investigation (2016). doi:10.1007/s40005-016-0273-9, published online on 18 Aug. 2016: "Design of transdermal matrix patch containing ondansetron".

The nsPAChAs Component (c)

Any nsPAChAs, exhibiting inhibitory activity broadly across the various subtypes of muscarinic M-receptors, namely the M1-M5 receptors, as currently identified and are largely unable (have a limited ability) to enter the central nervous system following systemic administration and thus do not affect brain function to a clinically appreciable degree may be used as Component (c) according to the present invention. These nsPAChAs include both quaternary ammonium salts, sulfonium salts and tertiary amine anticholinergic agents, especially those having low lipid solubility.

The 4-diethylaminobut-2-ynyl 2-cyclohexyl-2-hydroxy-2-phenylethanoate, known under its International Non-proprietary Name as oxybutynin, as free base or a pharmaceutically acceptable salt thereof, is a well-known non-selective anticholinergic medication used by oral route to relieve urinary and bladder difficulties, including frequent urination and urge incontinence and all the above references emphasize this use. Thus, oxybutynin is a very good tool for administering anticholinergic therapy, but it is not "peripheral" as per the definition given above because it is able to cross the blood brain barrier ("BBB") to a non-negligible extent (Rebecca J McCrery and Rodney A Appell, Ther Clin Risk Manag. March 2006; 2/1: 19-24).

Oxybutynin is also commercially presented in a 39-cm$^2$ patch system containing 36 mg of oxybutynin and releasing 3.9 mg/day oxybutynin (OXYTROL®). This patch provides significant improvements in all the measured parameters with less systemic adverse effects, as summarized by J. Jayarajan and S. B. Radomski in a review presented on 4 Dec. 2013: "Pharmacotherapy of overactive bladder in adults: a review of efficacy, tolerability, and quality of life" (J. Jayarajan et al., Research and Reports in Urology 2014: 6), the disclosure of which is herein incorporated by reference in its entirety. However, oxybutynin is anyway deemed to cross the BBB owing to its high lipophilicity, neutrality, and small molecular size (C. A. Donnellan et al. BMJ 1997; 315:1363-4; R. Scheife and M. Takeda, Clin Ther. 2005; 27:144-53). the disclosure of which is herein incorporated by reference in its entirety.

Even when given by transdermal route, oxybutynin has been shown to penetrate the brain. Studies with radiolabeled [$^{14}$C]oxybutynin administered transdermally to rats have shown presence of radiolabel in the brain [Pharmaceutical and Medical Devices Agency Interview Form (PMDA is the Japanese Regulataory Agency, equivalent to FDA in the US)].

Oxybutynin is also commercially presented (GELNIQUE®) in a TTS consisting of a hydroalcoholic gel containing 100 mg oxybutynin chloride per gram of gel and available in a 1 gram (1.14 ml) unit dose. This TTS is deemed to have a pharmacokinetic profile similar to that of the patch delivery system, while producing lower N-desethyloxybutynin metabolite plasma concentrations (Vincent R Lucente et al.; Open Access Journal of Urology 2011/3, 35-42). Another commercial TTS system, presents oxybutynin in a hydroalcoholic gel containing 30 mg oxybutynin base per gram of gel and is available (ANTUROL®) in a 0.92 gram (1 mL) unit dose that contains 28 mg oxybutynin per gram of gel. Also Anturol® demonstrated plasma levels of oxybutynin comparable to the efficacious plasma levels observed for oral and patch therapies with lower N-desethyloxybutynin plasma levels (Anturol® Gel Summary by Antares Pharma).

The label for transdermal oxybutynin warns that a variety of CNS anticholinergic effects have been reported, including headache, dizziness, and somnolence. Patients should be monitored for signs of anticholinergic CNS effects, particularly after beginning treatment. The label further advises that patients should be told not to drive or operate heavy machinery until they know how transdermal oxybutynin affects them. The label also advises that if a patient experiences anticholinergic CNS effects, drug discontinuation should be considered. In addition, the label states that overdosage with oxybutynin has been associated with CNS anticholinergic effects including excitation, memory loss, stupor, disorientation and agitation on awakening. Hence, based on the existing literature, and the competing action of oxybutynin and an AChEI in the CNS, the combined use of such drugs would have made memory loss a-priori material risk for the treatment of Alzheimer type dementia.

The copending applications U.S. Ser. No. 14/991,273 and PCT/US2016/012610 disclose the combination of oxybutynin or a pharmaceutically acceptable salt thereof, in a transdermal therapeutic system ("TTS-oxybutynin"), with an acetylcholinesterase inhibitor for the treatment of Alzheimer type dementia. According to these documents, it is possible to administer high doses of an AChEI such as rivastigmine, in combination with TTS-oxybutynin without inducing AChEI-associated dose-limiting adverse effects due to the concurrent presence of oxybutynin in the combination. In addition, according to these documents, the treated subjects did not show any sign of central anticholinergic adverse effects such as mental or mood changes (e.g., confusion or memory loss, somnolence or convulsions).

Thus, according to the present invention, contrary to oral oxybutynin and to the TTS-oxybutynin label statement, TTS-oxybutynin may considered, in every aspect, as a nsPAChA.

Advantageously, the nsPAChAs used as Component (c), include, but are not limited to, quaternary ammonium nsPAChAs, sulfonium nsPAChAs, (1S)-(3R)-1-azabicyclo[2.2.2]oct-3-yl 3,4-dihydro-1-phenyl-2(1H)-iso-quinolinecarboxylate (solifenacin) and pharmaceutically acceptable salts and solvates thereof, 1-methylpiperidin-4-yl) 2,2-di(phenyl)-2-propoxyacetate (propiverine) and pharmaceutically acceptable salts and solvates thereof, 1,4,5,6-tetrahydro-1-methylpyrimidin-2-ylmethyl α-cyclohexyl-α-hydroxy-α-phenylacetate (oxyphencyclimine) and pharmaceutically acceptable salts and solvates thereof, (R)—N,N-diisopropyl-3-(2-hydroxy-5-methylphenyl)-3-phenylpropanamine (tolterodine) and pharmaceutically acceptable salts and solvates thereof, [2-[(1R)-3-(di(propan-2-yl)amino)-1-phenylpropyl]-4-(hydroxymethyl)phenyl]2-methylpropanoate (fesoterodine) and pharmaceutically acceptable salts and solvates thereof, and TTS-oxybutynin.

Said nsPAChAs, preferably, are compounds with a duration of action of at least 6 hours, advantageously from 8 to 24 hours, more advantageously from 10 to 24 hours, preferably from 12 to 24 hours, even nsPAChAs having an appropriate duration of action corresponding to the duration of action of the concomitantly administered MCRA may be successfully used.

Typical quaternary ammonium nsPAChAs or sulfonium nsPAChAs are compounds of formula I

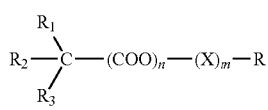

wherein
R is a radical selected from the group consisting of those of formulas (a)-(e)

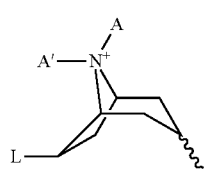

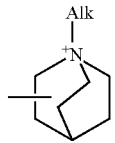

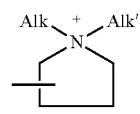

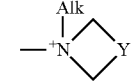

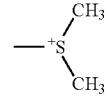

A being methyl and A' being $(C_1-C_4)$alkyl or 2-fluoroethyl group or A and A' forming a 1,4-butylene or 1,5-pentylene chain, L being hydrogen or methoxy, Alk and Alk' each being $(C_1-C_4)$alkyl and Y being a bivalent radical selected from the group consisting of 1,2-ethylene, 1,3-propylene, 1,4-butylene and 2-oxa-1,3-propylene; the corresponding counter ion being a pharmaceutically acceptable anion, such as a chloro, bromo, iodo, tartrate, hydrogen tartrate, succinate, maleate, fumarate, sulfate, hydrogen sulfate or methylsulfate anion;

n and m, independently, are zero or 1;

X is a $(C_2-C_3)$alkylene group;

$R_1$ and $R_2$ are each phenyl, cyclopentyl, cyclohexyl, 1-cyclohexenyl, 2-thienyl and, when R is a radical (a), also each represents $(C_1-C_4)$alkyl;

$R_3$ is H or OH or, only when R is a radical (a), also a COOAlk group, Alk being a $(C_1-C_4)$alkyl group.

Preferably, in the above formula I, at least one of m and n is 1.

Exemplary nsPAChAs of formula I above useful for the treatment of Alzheimer type dementia in combination with MCRAs are anisotropine methylbromide [R=(a), A=A'=CH$_3$, L=H; n=1; m=0; R$_1$=R$_2$=n-C$_3$H$_7$; R$_3$=H;];

ciclotropium bromide [R=(a), A=CH$_3$, A'=isopropyl, L=H; n=1; m=0; R$_1$=phenyl; R$_2$=cyclopentyl; R$_3$=H];

flutropium bromide [R=(a), A=CH$_3$, A'=2-fluoroethyl, L=H; n=1; m=0; R$_1$=R$_2$=phenyl; R$_3$=OH];

homatropine methylbromide [R=(a), A=A'=CH$_3$, L=H; n=1; m=0; R$_1$=phenyl; R$_2$=R$_3$=H];

sintropium bromide; [R=(a), A=CH$_3$, A'=isopropyl, L=H; n=1; m=0; R$_1$=R$_2$=n-C$_3$H$_7$; R$_3$=H];

tematropium metilsulfate [R=(a), A=A'=CH$_3$, L=H; n=1; m=0; R$_1$=phenyl; R$_2$=COOC$_2$H$_5$; R$_3$=H];

tropenziline bromide [R=(a), A=A'=CH$_3$, L=methoxy; n=1; m=0; R$_1$=R$_2$=phenyl, R$_3$=OH];

trospium chloride [R=(a), A+A'=1,4-butylene, L=H; n=1; m=0; R$_1$=R$_2$=phenyl; R$_3$=OH];

clidinium bromide [R=(b)-3-, Alk=methyl; n=1; m=0; R$_1$=R$_2$=phenyl; R$_3$=OH];

droclidinium bromide [R=(b)-3-, Alk=methyl; n=1; m=0; R$_1$=phenyl; R$_2$=cyclopentyl; R$_3$=OH];

benzilonium bromide [R=(c)-3-, both Alk and Alk'=ethyl; n=1; m=0; $R_1=R_2$=phenyl; $R_3$=OH];

benzopyrronium bromide [R=(c)-3-, both Alk and Alk'=methyl; n=1; m=0; $R_1=R_2$=phenyl; $R_3$=OH];

cyclopyrronium bromide [R=(c)-3-, Alk=methyl and Alk'=ethyl; n=1; m=0; $R_1$=phenyl; $R_2$=cyclopentyl; $R_3$=H];

glycopyrronium bromide (glycopyrrolate) [R=(c)-3-, both Alk and Alk'=methyl; n=1; m=0; $R_1$=phenyl; $R_2$=cyclopentyl; $R_3$=H];

heteronium bromide [R=(c)-3-, both Alk and Alk'=methyl n=1; m=0; $R_1$=phenyl; $R_2$=2-thienyl; $R_3$=OH];

hexopyrronium bromide [R=(c)-3-, both Alk and Alk'=methyl; n=1; m=0; $R_1$=phenyl; $R_2$=cyclohexyl; $R_3$=H];

oxypyrronium bromide [R=(c)-2-, both Alk and Alk'=methyl; n=1; m=1; X=1,2-ethylene; $R_1$=phenyl; $R_2$=cyclohexyl; $R_3$=OH];

ritropirronium bromide [R=(c)-3-, both Alk and Alk'=methyl; n=1; m=0; $R_1$=phenyl; $R_2$=cyclopentyl; $R_3$=OH];

etipirium iodide [R=(d), Alk=methyl, Y=1,2-ethylene; n=1; m=1; X=1,2-ethylene; $R_1=R_2$=phenyl; $R_3$=OH];

fenclexonium methylsulfate [R=(d), Alk=$CH_3$, Y=1,3-propylene; n=0; m=1; X=1,2-ethylene; $R_1$=phenyl; $R_2$=1-cyclohexenyl; $R_3$=H];

tricyclamol chloride (procyclidine methochloride) [R=(d), Alk=methyl, Y=1,2-ethylene; n=0; m=1; X=1,2-ethylene; $R_1$=phenyl; $R_2$=cyclohexyl; $R_3$=OH];

tiemonium iodide [R=(d), Alk=methyl, Y=2-oxa-1,3-propylene; n=0; m=1; X=1,2-ethylene; $R_1$=phenyl; $R_2$=2-thienyl; $R_3$=OH];

hexasonium iodide [R=(e); n=1; m=1; X=1,2-ethylene; $R_1$=phenyl; $R_2$=cyclohexyl; $R_3$=H]; and oxysonium iodide [R=(e); n=1; m=1; X=1,2-ethylene; $R_1$=phenyl; $R_2$=cyclohexyl; $R_3$=OH.

Other typical, commercial nsPAChAs, not included in Formula I above, include, but are not limited to, cimetropium bromide, otilonium bromide, prifinium bromide, timepidium bromide, scopolamine methobromide, scopolamine butylbromide, scopolamine methonitrate, isopropamide iodide, valethamate bromide, atropine methobromide, atropine methonitrate, diponium bromide, pipenzolate bromide, penthienate bromide, benactizine methobromide, diphemanil, emeprioum bromide and dibutoline sulfate.

Advantageous nsPAChAs are the tertiary amine or quaternary ammonium compounds available in drugs for current anticholinergic therapy, in particular anisotropine methyl bromide, available with a maximum dose/unit form of 100 mg; butylscopolamine bromide, with a maximum dose/unit form of 10 mg; cimetropium bromide, with a maximum dose/unit form of 50 mg; clidinium bromide, with a maximum dose/unit form of 2.5 mg; ER fesoterodine fumarate, with a maximum dose/unit form of 8 mg; glycopyrronium bromide, with a maximum dose/unit form of 2 mg; otilonium bromide, with a maximum dose/unit form of 40 mg; oxyphencyclimine hydrochloride with a maximum dose/unit form of 10 mg: prifinium bromide, with a maximum dose/unit form of 30 mg; IR propiverine hydrochloride, with a maximum dose/unit form of 15 mg; ER propiverine hydrochloride, with a maximum dose/unit form of 30 mg; solifenacin succinate, with a maximum dose/unit form of 10 mg; timepidium bromide, with a maximum dose/unit form of 30 mg; IR trospium chloride, with a maximum dose/unit form of 20 mg; ER trospium chloride, with a maximum dose/unit form of 60 mg; TTS-oxybutynin, available as a patch releasing 3.9 mg/24 h oxybutynin, or as a gel in an amount as illustrated above; and valethamate bromide, with a maximum dose/unit form of 10 mg.

Azoniaspiro [3β-benziloyloxy-(1α,5α)-nortropane-8,1'-pyrrolidine]chloride (formula I, A+A'=1,4-butylene) described in U.S. Pat. No. 3,480,626, known under its International Non-proprietary Name trospium chloride; the tartrate, maleate, fumarate and succinate salts of trospium; solifenacin, described in U.S. Pat. No. 6,017,927, and the compound thereof with succinic acid; propiverine hydrochloride, described in DD 106643, and its quaternary methylpropiverinium iodide and methylpropiverinium bromide, described in WO2014/025569; oxyphencyclimine, described in GB 795758, and the hydrochloride thereof; tolterodine, described in U.S. Pat. No. 5,382,600, and the hydrogen tartrate thereof; fesoterodine, described in U.S. Pat. No. 5,382,600, and the fumarate thereof, and TTS-oxybutynin are the preferred nsPAChAs. Other pharmaceutical acceptable salts of trospium, in particular those with succinic acid and tartaric acid, are cited in US 2006/0293356.

Thus, according to an advantageous embodiment the nsPAChA is preferably selected from the group consisting of anisotropine pharmaceutically acceptable quaternary salts, butylscopolamine pharmaceutically acceptable salts, cimetropium pharmaceutically acceptable salts, clidinium pharmaceutically acceptable salts, fesoterodine and pharmaceutically acceptable salts thereof, glycopyrronium pharmaceutically acceptable salts, otilonium pharmaceutically acceptable salts, oxyphencyclimine and pharmaceutically acceptable salts thereof, prifinium pharmaceutically acceptable salts, propiverine and pharmaceutically acceptable salts thereof, solifenacin and pharmaceutically acceptable salts thereof, tolterodine and pharmaceutically acceptable salts thereof, timepidium pharmaceutically acceptable salts, trospium pharmaceutically acceptable salts, TTS-oxybutynin; and valethamate pharmaceutically acceptable salts.

Glycopyrronium bromide; trospium chloride, which is a long-acting nsPAChA whose absorbed amount, even though poor, has an average plasma half-life of about 18 hours; solifenacin succinate, which also has a long half-life; propiverine hydrochloride and the aforementioned quaternary ammonium salts thereof, and TTS-oxybutynin are particularly preferred.

The nsPAChA Component (c) of the present invention can be formulated in pharmaceutical compositions comprising, as an active ingredient thereof, said nsPAChA in admixture with a pharmaceutical carrier.

Said Component (c) is present in an amount that allows the reduction of peripherally mediated adverse effects that would be caused by the administration of doses of MCRA which are higher that the maximal tolerated dose found for each of them in the clinical trials of said MCRA.

In a preferred embodiment, the amount of a nsPAChA, such as of each of the aforementioned tertiary amine and quaternary ammonium nsPAChAs that is commercially available for the anticholinergic therapy, may be from 0.5 times to 8 times, generally from 0.5 to 6 times, the maximum amount contained in the IR-forms of the marketed drugs. More particularly, according to this preferred embodiment the nsPAChA amount in a compositions as IR-formulation, generally is from 0.5 to 4 times, preferably from 1.2 to 4 times the maximum amount contained in the marketed drugs in IR form and the nsPAChA amount in a compositions as ER-formulation is from 0.75-times to 6-times, preferably from 1.2-times to 6-times the maximum amount contained in the marketed drugs in IR form or in an amount of from 0.75-times to 4-times, preferably from 1.2-times to 4-times the maximum amount contained in the marketed drugs in ER form.

According to a preferred embodiment, the combination of the present invention comprises, as advantageous Component (c), a nsPAChA selected from the group consisting of glycopyrronium pharmaceutically acceptable salts, in an amount that is equivalent to from 1 mg to 24 mg of glycopyrronium bromide; propiverine and pharmaceutically acceptable salts thereof, in an amount that is equivalent to from 15 mg to 240 mg of propiverine hydrochloride; solifenacin and pharmaceutically acceptable salts thereof, in an amount that is equivalent to from 5 mg to 60 mg of solifenacin succinate; trospium pharmaceutically acceptable salts, in an amount that is equivalent to from 20 mg to 480 mg of trospium chloride; and TTS-oxybutynin, in an amount releasing from 3.9 mg/24 h to 7.8 mg/24 h oxybutynin.

According to a more specific embodiment, the combination of the present invention comprises, as Component (c), ansPAChA selected from the group consisting of anisotropine methylbromide, in an amount from 25 mg to 300 mg, advantageously from 60 mg to 300 mg, normally from 60 mg to 200 mg; cimetropium bromide, in an amount from 25 mg to 300 mg, advantageously from 60 mg to 300 mg, normally from 60 mg to 200 mg; clidinium bromide, in an amount from 1.25 mg to 15 mg, advantageously from 3 mg to 15 mg, normally from 3 mg to 10 mg; fesoterodine fumarate, in an amount from more than 4 mg to 480 mg, advantageously from 9.6 mg to 480 mg, normally from 9.6 mg to 320 mg; glycopyrronium bromide, in an amount from 1 mg to 16 mg, advantageously from 2.4 mg to 12 mg, normally from 2.4 mg to 8 mg; otilonium bromide, in an amount from 20 mg to 240 mg, advantageously from 48 mg to 240 mg, normally from 48 mg to 160 mg; oxyphencyclimine hydrochloride, in an amount from 5 mg to 60 mg, advantageously from 12 mg to 60 mg, normally from 12 mg to 40 mg; prifinium bromide, in an amount from 15 mg to 180 mg, advantageously from 36 mg to 180 mg, normally from 36 mg to 120 mg; propiverine hydrochloride, in an amount from 7.5 mg to 180 mg, advantageously from 17.5 mg to 180 mg, normally from 17.5 mg to 120 mg; solifenacin succinate, in an amount from 5 mg to 60 mg, advantageously from 10 mg to 40 mg, normally from 12 mg to 25 mg, and of 21 mg; timepidium bromide, in an amount from 15 mg to 180 mg, advantageously from 36 mg to 180 mg, normally from 36 mg to 120 mg; trospium chloride, in an amount of from 10 mg to 480 mg, advantageously from 10 mg to 360 mg, normally form 24 mg to 360 mg; and TTS-oxybutynin, in a released amount (from a patch) of from 3.9 mg/24 h to 7.8 mg/24 h, advantageously from 3.9 mg/24 h to 5.85 mg/24 h, normally of 3.9 mg/24 h.

In the above combination, propiverine hydrochloride is preferably present in an amount of from 18 mg to 90 mg in an IR-formulated composition, in admixture with a pharmaceutical carrier or in an amount of from 36 mg to 180 mg in an ER-formulated composition, in admixture with a pharmaceutical carrier. Similarly, in the above combination trospium chloride is preferably present in an amount of from 24 mg to 80 mg in an IR-formulated composition, in admixture with a pharmaceutical carrier or in an amount of from 72 mg to 240 mg in an ER-formulated composition, in admixture with a pharmaceutical carrier and TTS-oxybutynin is preferably present in a patch delivering from 3.9 mg/24 h to 7.8 mg/24 h oxybutynin. Solifenacin succinate is preferably present in an amount selected from the group consisting of from 5 mg to 60 mg, from 10 mg to 40 mg, from 12 mg to 30 mg, from 12 mg to 25 mg, and 21 mg.

In general, if these preferred nsPAChAs are in form of a pharmaceutical acceptable salt other than that of the corresponding, commercial nsPAChA, the nsPAChA amount that is present in the combination is preferably equivalent to that of said corresponding commercial nsPAChA.

The compositions prepared using the nsPAChAs as Component (c) of the combination according to the present invention allow the administration of normally 1.2- to 4-times, but even 1.2- to 6-times the maximal tolerated dose of MCRA, as averagely determined in the clinical trials, to patients suffering of Alzheimer type dementia, without clinically significant symptoms of peripheral cholinergic system overstimulation.

The compositions are preferably formulated in dosage unit forms for oral or parenteral, in particular transdermal, administration, wherein the active ingredient is mixed with a pharmaceutical carrier or vehicle.

The pharmaceutical compositions prepared using the nsPAChAs Component (c) according to the present invention are indicated in the treatment of hypocholinergic disorders in combination with a naAEA Component (b) and even high doses of a MCRA Component (a), concurrently or sequentially administered therewith, in order to improve to a greater extent said symptoms without adverse effects.

According to a particular embodiment, nsPAChAs Component (c) according to the present invention is in a fixed-dose combination with a naAEA Component (b), wherein said nsPAChAs Component (c) is present in an amount of from 100% to 600%, up to 800% the maximum amount contained in the commercial brand or generic products used for the anticholinergic therapy.

A particularly advantageous combination according to this particular embodiment is a fixed dose combination of a nsPAChA selected from the group consisting of propiverine and pharmaceutically acceptable salts thereof, in an amount corresponding to from 15 mg to 240 mg of propiverine hydrochloride, trospium pharmaceutically acceptable salts, in an amount corresponding to from 20 mg to 480 mg of trospium chloride; and glycopyrronium pharmaceutically acceptable salts corresponding to from 2 mg to 16 mg of glycopyrronium bromide, with a naAEA, in a pharmaceutical composition in admixrurewit a pharmaceutical carrier or vehicle.

Thus, the invention provides compositions and methods for treating hypocholinergic disorders, which comprises administering to a patient in need of said treatment the above-illustrated combination. In such a treatment, Component (a), Component (b) and Component (c) of the combination may be administered simultaneously or sequentially to said patient, Component (a) being indifferently administered before or after Component (b) and Component (c). Components (a), Component (b) and Component (c) may also be administered by the same or a different administration route.

The invention further provides the above combination comprising Component (a), Component (b) and Component (c), preferably each formulated in a pharmaceutical composition in admixture with a pharmaceutical carrier or vehicle, for use in the treatment of hypocholinergic disorders as herein above defined.

The invention may also include a fourth component, Component (d), that is an AChEI, also preferably formulated in a pharmaceutical composition in admixture with a pharmaceutical carrier or vehicle.

The Combinations

The present invention provides the combination of any MCRA, any naAEA and any nsPAChA as exemplified in the respective sections herein, each formulated in pharmaceutical composition in admixture with a pharmaceutical carrier.

In particular, the combination of the present invention may be a combination comprising or consisting essentially of (a) any of the MCRAs such as those described herein above, each in a pharmaceutical composition in dosage unit form, in admixture with a pharmaceutical carrier or vehicle, said MCRA being preferably selected from the group consisting of AF267 and pharmaceutically acceptable salts and solvates thereof; cevimeline and pharmaceutically acceptable salts and solvates thereof; EUK 1001 and pharmaceutically acceptable salts and solvates thereof; milameline and pharmaceutically acceptable salts and solvates thereof; RS-86 and pharmaceutically acceptable salts and solvates thereof; sabcomeline and pharmaceutically acceptable salts and solvates thereof; talsaclidine and pharmaceutically acceptable salts and solvates thereof; tazomeline and pharmaceutically acceptable salts and solvates thereof; xanomeline and pharmaceutically acceptable salts and solvates thereof; AC-42 and pharmaceutically acceptable salts and solvates thereof; TBPB and pharmaceutically acceptable salts and solvates thereof; 4-Fluoro-6-methyl-1-[1-(tetrahydro-2H-pyran-4-yl)-4-piperidinyl]-1,3-dihydro-2H-benzimidazol-2-one; and pharmaceutically acceptable salts and solvates thereof; 5-Fluoro-6-methyl-1-[1-(tetrahydro-2H-pyran-4-yl)-4-piperidinyl]-1,3-dihydro-2H-benzimidazol-2-one and pharmaceutically acceptable salts and solvates thereof; 4-(R)-ethyl-3-(2-methylbenzamido)-1,4'-bipiperidine-1'-carboxylate and pharmaceutically acceptable salts and solvates thereof; ethyl 3-[(3-exo)-(2-benzamidoethyl)amino]-8-azabicyclo[3.2.1]octane-8-carboxylate and pharmaceutically acceptable salts and solvates thereof; 5-(3-ethyl-1,2,4-oxadiazol-5-yl)-1,4,5,6-tetrahydropyrimidine (MCD-386) and pharmaceutically acceptable salts and solvates thereof; 3-Methyl-5-(piperidin-3-yl)-1,2,4-oxadiazole, its enantiomers and pharmaceutically acceptable salts and solvates thereof; and MK-7622 and pharmaceutically acceptable salts and solvates thereof;

(b) any of the naAEA such as those described herein, each in a pharmaceutical composition in admixture with a pharmaceutical carrier or vehicle, said naAEA being preferably selected from the group consisting of alosetron and pharmaceutically acceptable salts and solvates thereof; dolasetron and pharmaceutically acceptable salts and solvates thereof; granisetron and pharmaceutically acceptable salts and solvates thereof; ondansetron and pharmaceutically acceptable salts and solvates thereof; palonosetron and pharmaceutically acceptable salts and solvates thereof; domperidone and pharmaceutically acceptable salts and solvates thereof; tropisetron and pharmaceutically acceptable salts and solvates thereof; domperidone and pharmaceutically acceptable salts and solvates thereof; haloperidol; chlorpromazine and pharmaceutically acceptable salts and solvates thereof; prochlorperazine and pharmaceutically acceptable salts and solvates thereof; metoclopramide and pharmaceutically acceptable salts and solvates thereof; bromopride and pharmaceutically acceptable salts and solvates thereof; clebopride and pharmaceutically acceptable salts and solvates thereof; levosulpiride; alizapride and pharmaceutically acceptable salts thereof; trimethobenzamide and pharmaceutically acceptable salts thereof; meclizine (also called meclozine) and pharmaceutically acceptable salts and solvates thereof; promethazine and pharmaceutically acceptable salts and solvates thereof; dronabinol; nabilone; aprepitant; netupitant; rolapitant; casopitant; and (c) any of the nsPAChAs such as those described herein, each in a pharmaceutical composition in admixture with a pharmaceutical carrier or vehicle, said nsPAChA being preferably selected from the group consisting of anisotropine pharmaceutically acceptable salts, butylscopolamine pharmaceutically acceptable salts, cimetropium pharmaceutically acceptable salts, clidinium pharmaceutically acceptable salts, fesoterodine and pharmaceutically acceptable salts thereof, glycopyrronium pharmaceutically acceptable salts, otilonium pharmaceutically acceptable salts, oxyphencyclimine and pharmaceutically acceptable salts thereof, prifinium pharmaceutically acceptable salts, propiverine and pharmaceutically acceptable salts thereof, solifenacin and pharmaceutically acceptable salts thereof, tolterodine and pharmaceutically acceptable salts thereof, timepidium pharmaceutically acceptable salts, trospium pharmaceutically acceptable salts, TTS-oxybutynin and pharmaceutically acceptable salts thereof; and valethamate pharmaceutically acceptable salts.

In the avove combination, each of the Components (a), (b) and (c) are in pharmaceutical composition in dosage unit form wherein each of said components is in admixture with a pharmaceutical carrier or vehicle.

A particularly advantageous combination essentially consists of (a) a MCRA selected from the group consisting of cevimeline and pharmaceutically acceptable salts thereof, in an amount (in cevimeline) of from 34.5 mg to 180 mg; milameline and pharmaceutically acceptable salts thereof, in an amount (in milameline) of from 2.4 mg to 12 mg; xanomeline and pharmaceutically acceptable salts thereof, in an amount (in xanomeline) of from 90 mg to 450 mg; and MK-7622 and pharmaceutically acceptable salts thereof, in an amount (in MK-7622) of from from 5 mg to 270 mg; in a pharmaceutical composition in admixture with a pharmaceutical carrier or vehicle;

(b) a naAEA selected from the group consisting of ondansetron and pharmaceutically acceptable salts and solvates thereof, in an amount (in ondansetron) of fro 4 mg to 64 mg, domperidone and pharmaceutically acceptable salts and solvates thereof, in an amount, in domperidone of from 5 mg to 30 mg; and metoclopramide and pharmaceutically acceptable salts and solvates the, in an amount (in metoclopramide) of from 5 mg to 30 mg; in a pharmaceutical composition in admixture with a pharmaceutical carrier or vehicle; and (c) a nsPAChA consisting of oxybutynin and pharmaceutically acceptable salts thereof, in admixture with a pharmaceutical carrier or vehicle in a TTS, said TTS being a transdermal patch releasing from 3.9 mg/24 h to 7.8 mg/24 h, preferably 3.9 mg/24 h oxybutynin.

According to a first embodiment, an advantageous combination may be a combination comprising or consisting essentially of (a) a MCRA selected from the group consisting of cevimeline, cevimeline hydrochloride hemihydrate, milameline, milameline hydrochloride, xanomeline, xanomeline oxalate, xanomeline L-tartrate, racemic 3-Methyl-5-(piperidin-3-yl)-1,2,4-oxadiazole and pharmaceutically acceptable salts and solvates thereof, S-(+)-3-methyl-5-(piperidin-3-yl)-1,2,4-oxadiazole D-tartrate; R-(−)-3-Methyl-5-(piperidin-3-yl)-1,2,4-oxadiazole L-tartrate; MK-7622, MK-7622 hydrochloride, MK-7622 methanesulfonate and MK-7622 fumarate, in a pharmaceutical composition in admixture with a pharmaceutical carrier or vehicle.
(b) a naAEA, in a pharmaceutical composition in admixture with a pharmaceutical carrier or vehicle; and
(c) a nsPAChA, in a pharmaceutical composition in admixture with a pharmaceutical carrier or vehicle.

According to this first embodiment, a preferred combination may be a combination comprising or consisting essentially of
(a) a MCRA selected from the group consisting of cevimeline hydrochloride hemihydrate, in an amount of from 34.5 mg to 180 mg, xanomeline, as free base, as oxalate or as L-tartrate, in an amount of from 90 mg to 450 mg, milameline hydrochloride, in an amount of from 2.4 mg to 12 mg; and MK 7622, as free base, as hydrochloride, as fumarate or as methanesulfonate, in an amount consisting of from more than 5 mg to 15 mg, from more than 15 mg to 45 mg, from more than 45 mg to 270 mg, from more than 15 mg to 225 mg, from more than 45 mg to 225 mg, and from 54 mg to 180 mg, in a pharmaceutical composition in admixture with a pharmaceutical carrier or vehicle;
(b) a naAEA in a pharmaceutical composition in admixture with a pharmaceutical carrier or vehicle; and
(c) a nsPAChA in a pharmaceutical composition in admixture with a pharmaceutical carrier or vehicle.

Preferably, in this combination, cevimeline Component (a), as free base or hydrochloride hemihydrate, is present in an amount of from 36 mg to 180 mg; and MK-7622, as free base, as hydrochloride, as methanesulfonate or as fumarate, is present in an amount consisting of from 5 mg to 270 mg, in particular of from more than 5 mg to 15 mg, from more than 15 mg to 45 mg, from more than 45 mg to 270 mg, from more than 15 mg to 225 mg, from more than 45 mg to 225 mg, and from 54 mg to 180 mg.

The pharmaceutical combinations of this first embodiment of the present invention, are useful for the treatment of hypocholinergic disorders, and even high doses of a MCRA Component (a), may be present to improve symptoms without adverse effects to a greater extent.

Thus, the present invention provides a method for treating hypocholinergic disorders, which comprises administering to a patient in need of said treatment the triple combinations described herein in one embodiment. In such a treatment, Component (a), Component (b) and Component (c) of the combination may be administered simultaneously or sequentially to said patient, Component (a) being indifferently administered before or after Component (b) and Component (c). Components (a), Component (b) and Component (c) may also be administered by the same or a different administration route.

According to a second embodiment, the present invention provides a pharmaceutical combination comprising or consisting essentially of, as Components:
(a) a MCRA, in a pharmaceutical composition in admixture with a pharmaceutical carrier or vehicle
(b) a naAEA selected from the group consisting of (b1) 5HT3-antagonists, (b2) DA-antagonists, (b3) H1-antagonists, (b4) cannabinoids, (b5) NK1-antagonists, and the netupitant-palonosetron fixed-dose combination, in a pharmaceutical composition in admixture with a pharmaceutical carrier or vehicle; and
(c) a nsPAChA, in a pharmaceutical composition in admixture with a pharmaceutical carrier or vehicle.

Another advantageous combination is one comprising or consisting essentially of (a) a MCRA, in a pharmaceutical composition in admixture with a pharmaceutical carrier or vehicle.
(b) a naAEA consisting of a 5HT3-antagonist selected from the group consisting of alosetron and pharmaceutically acceptable salts and solvates thereof, azasetron and pharmaceutically acceptable salts and solvates thereof; ondansetron and pharmaceutically acceptable salts and solvates thereof; granisetron and pharmaceutically acceptable salts and solvates thereof; dolasetron and pharmaceutically acceptable salts and solvates thereof, ramosetron and pharmaceutically acceptable salts and solvates thereof; tropisetron and pharmaceutically acceptable salts and solvates thereof; and palonosetron and pharmaceutically acceptable salts and solvates thereof, in a pharmaceutical composition in admixture with a pharmaceutical carrier or vehicle; and
(c) a nsPAChA, in a pharmaceutical composition in admixture with a pharmaceutical carrier or vehicle.

According to this second embodiment, another advantageous triple combination is a combination comprising or consisting essentially of:
(a) a MCRA, in a pharmaceutical composition in admixture with a pharmaceutical carrier or vehicle;
(b) a naAEA consisting of a 5HT3-antagonist selected from the group consisting of alosetron and pharmaceutically acceptable salts and solvates thereof, in particular the hydrochloride, in an amount (in alosetron) of from 0.25 mg to 6 mg; azasetron and pharmaceutically acceptable salts and solvates thereof, in particular the hydrochloride, in an amount (in azasetron) of from 5 mg to 60 mg; dolasetron and pharmaceutically acceptable salts and solvates thereof, in particular the mesylate, in an amount (in dolasetron) of from 25 mg to 600 mg; granisetron and pharmaceutically acceptable salts and solvates thereof, in particular the hydrochloride, in an amount (in granisetron) of from 0.5 mg to 6 mg; ondansetron and pharmaceutically acceptable salts and solvates thereof, in particular the hydrochloride dihydrate, in an amount (in ondansetron) of from 2 mg to 64 mg; palonosetron and pharmaceutically acceptable salts thereof, in particular the hydrochloride, in an amount (in palonosetron) of from 0.25 mg to 3 mg; ramosetron and pharmaceutically acceptable salts thereof, in particular its hydrochloride, in an amount (in ramosetron) of from 0.0125 mg to 0.3 mg, tropisetron and pharmaceutically acceptable salts and solvates thereof, in particular the hydrochloride, in an amount of from 2.5 mg to 30 mg, in a pharmaceutical composition in admixture with a pharmaceutical carrier or vehicle; and
(c) a nsPAChA in a pharmaceutical composition in admixture with a pharmaceutical carrier or vehicle.

A specific MCRA/naAEA/nsPAChA combination comprises
(a) a MCRA, in a pharmaceutical composition in admixture with a pharmaceutical carrier or vehicle;
(b) a naAEA consisting of a fixed-dose combination comprising palonosetron, in an amount of from 0.25 mg to 3 mg of palonosetron or a pharmaceutically acceptable salt thereof such as its hydrochloride and from 150 mg to 600 mg of netupitant, in admixture with a pharmaceutical carrier or vehicle in an oral IR formulation; and
(c) a nsPAChA in a pharmaceutical composition in admixture with a pharmaceutical carrier or vehicle.

In said specific MCRA/naAEA/nsPAChA combination, the naAEA Component (b) preferably is a fixed-dose combination consisting of a pharmaceutical composition in dosage unit form comprising palonosetron hydrochloride, in an amount (in palonosetron) of 0.5 mg and of netupitant, in an amount of 300 mg, in admixture with a pharmaceutical carrier in an oral IR formulation.

According to this second embodiment, another advantageous combination is a combination comprising or consisting essentially of:
(a) a MCRA, in a pharmaceutical composition in admixture with a pharmaceutical carrier or vehicle;
(b) a naAEA consisting of a DA-antagonist consisting of domperidone and pharmaceutically acceptable salts and solvates thereof such as the maleate; chlorpromazine and pharmaceutically acceptable salts and solvates thereof such as the hydrochloride; prochlorperazine and its salts and solvates, particularly the dimaleate and the dimesylate; promethazine and pharmaceutically acceptable salts and solvates thereof such as the hydrochloride; and 4-aminosalicylamide derivatives such as metoclopramide and pharmaceutically acceptable salts and solvates thereof such as the hydrochloride monohydrate, bromopride and pharmaceutically acceptable salts and solvates thereof such as the monohydrochloride or the dihydrochloride monohydrate, alizapride and pharmaceutically acceptable salts and solvates thereof such as the hydrochloride, and clebopride and pharmaceutically acceptable salts and solvates thereof such as the malate and the hydrochloride monohydrate; in a pharmaceutical composition in admixture with a pharmaceutical carrier or vehicle; and
(c) a nsPAChA in a pharmaceutical composition in admixture with a pharmaceutical carrier or vehicle.

An advantageous combination according to this second embodiment is a combination comprising or consisting essentially of the following Components:
(a) a MCRA, in a pharmaceutical composition in admixture with a pharmaceutical carrier or vehicle;
(b) a naAEA consisting of a DA-antagonist consisting of domperidone or a pharmaceutically acceptable salt thereof, in particular its maleate, in an amount (in domperidone) of from 5 mg to 20 mg per dosage unit in an IR unit form or in an amount of from 7.5 mg to 60 mg, preferably from 10 mg to 60 mg, in an ER unit form; metoclopramide or a pharmaceutically acceptable salt or solvate thereof, in particular its monohydrochloride monohydrate, in an amount (in metoclopramide) of from 5 mg to 20 mg per dosage unit in an IR unit form or in an amount of from 7.5 mg to 30 mg, preferably from 10 mg to 30 mg, in an ER unit form; alizapride or a pharmaceutically acceptable salt thereof, in particular its hydrochloride, in an amount (in alizapride) of from 25 mg to 100 mg per dosage unit in an IR unit form or in an amount of from 37.5 mg to 300 mg, preferably from 100 mg to 300 mg, in an ER unit form; in a pharmaceutical composition in admixture with a pharmaceutical carrier or vehicle; and
(c) a nsPAChA in a pharmaceutical composition in admixture with a pharmaceutical carrier or vehicle.

A further advantageous combination according to this second embodiment, is a combination comprising or consisting essentially of the following Components:
(a) a MCRA, in a pharmaceutical composition in admixture with a pharmaceutical carrier or vehicle;
(b) a naAEA consisting of a histamine H1 receptor antagonists selected from the group consisting of meclizine (meclozine) and pharmaceutically acceptable salts and solvates thereof such as the hydrochloride monohydrate; promethazine and pharmaceutically acceptable salts and solvates thereof such as the hydrochloride; chlorpromazine and pharmaceutically acceptable salts and solvates thereof such as the hydrochloride, prochlorperazine and pharmaceutically acceptable salts and solvates thereof such as the dimaleate, the dimesylate or the 1,2-ethanedisulfonate (1:1) (edisilate); hydroxyzine and pharmaceutically acceptable salts and solvates thereof such as the dihydrochloride or the 1,1'-methylene bis(2-hydroxy-3-naphthalenecarboxylic acid (pamoate) salt; in a pharmaceutical composition in admixture with a pharmaceutical carrier or vehicle and
(c) a nsPAChA in a pharmaceutical composition in admixture with a pharmaceutical carrier or vehicle.

According to this second embodiment, a further advantageous combination is a combination comprising or consisting essentially of the following Components:
(a) a MCRA, in a pharmaceutical composition in admixture with a pharmaceutical carrier or vehicle;
(b) a naAEA consisting of a histamine H1 receptor antagonists selected from the group consisting of meclizine or a pharmaceutically acceptable salt thereof, in particular its hydrochloride, in an amount (in meclizine) of from 25 mg to 100 mg per dosage unit in an IR unit form or in an amount of from 37.5 mg to 150 mg, preferably from 50 mg to 150 mg, in an ER unit form; chlorpromazine or a pharmaceutically acceptable salt thereof, in particular its hydrochloride, in an amount (in chlorpromazine) of from 50 mg to 200 mg per dosage unit in an IR unit form or in an amount of from 75 mg to 300 mg, preferably from 100 mg to 300 mg, in an ER unit form; prochlorperazine or a pharmaceutically acceptable salt thereof, in particular its maleate, in an amount (in prochlorperazine) of from 2.5 mg to 10 mg per dosage unit in an IR unit form or in an amount of from 3.75 mg to 15 mg, preferably from 5 mg to 15 mg, in an ER unit form; in a pharmaceutical composition in admixture with a pharmaceutical carrier or vehicle; and
(c) a nsPAChA in a pharmaceutical composition in admixture with a pharmaceutical carrier or vehicle.

A preferred combination according to this second embodiment is a combination comprising or consisting essentially of the following Components:
(a) a MCRA, in a pharmaceutical composition in admixture with a pharmaceutical carrier or vehicle;
(b) a naAEA selected from the group consisting of alosetron hydrochloride, in an amount (in alosetron) of from 0.25 mg to 6 mg; azasetron hydrochloride, in an amount (in azasetron) of from 5 mg to 60 mg; dolasetron mesylate, in an amount (in dolasetron) of from 25 mg to 600 mg; granisetron hydrochloride, in an amount (in granisetron) of from 0.5 mg to 6 mg; ondansetron hydrochloride dihydrate, in an amount (in ondansetron) of from 2 mg to 64 mg; palonosetron hydrochloride, in an amount (in palonosetron) of from 0.25 mg to 3 mg; ramosetron hydrochloride, in an amount (in ramosetron) of from 0.0125 mg to 0.3 mg, tropisetron hydrochloride, in an amount (in tropisetron) of from 2.5 mg to 30 mg; domperidone and pharmaceutically acceptable salts and solvates thereof, in an amount (in domperidone) of from 5 mg to 60 mg; haloperidol, in an amount of from 0.5 mg to 60 mg; chlorpromazine hydrochloride, in an amount (in chlorpromazine) of from 12.5 mg to 600 mg; prochlorperazine dimaleate, in an amount (in prochlorperazine) of from 2.5 mg to 30 mg; metoclopramide monohydrochloride monohydrate, in an amount (in metoclopramide) of from 5 mg to 60 mg; bromopride monohydrochloride or dihydrochloride monohydrate, in an amount (in bromopride) of from 5 mg to 60 mg; clebopride hydrogen malate or hydrochloride monohydrate, in an amount (in clebopride) of from 0.25 mg to 3 mg; levosulpiride, in an amount of from 12.5 mg to 600 mg; alizapride hydrochloride, in an amount (in alizapride) of from 25 mg to 300 mg; trimethobenzamide monohydrochloride, in an amount (in trimethobenzamide) of from 50 mg to 600 mg; meclizine (also called meclozine) and pharmaceutically acceptable salts and solvates thereof, in an amount (in meclizine) of from 6.25 mg to 300 mg; promethazine hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant, in an amount of from 25 mg to 300 mg; in a pharmaceutical composition in admixture with a pharmaceutical carrier or vehicle; and (c) a nsPAChA in a pharmaceutical composition in admixture with a pharmaceutical carrier.

The pharmaceutical combination according to this second embodiment are indicated in the treatment of hypocholinergic disorders and even high doses of a MCRA Component (a), may be present said symptoms without adverse effects to a greater extent.

Thus, the present invention provides a method for treating hypocholinergic disorders, which comprises administering to a patient in need of said treatment the triple combinations described according to this second embodiment. In such a treatment, Component (a), Component (b) and Component (c) of the combination may be administered simultaneously or sequentially to said patient, Component (a) being indifferently administered before or after Component (b) and Component (c). Components (a), Component (b) and Component (c) may also be administered by the same or a different administration route.

According to a third embodiment, the invention provides a pharmaceutical combination comprising or consisting essentially of, as Components:
(a) a MCRA, in a pharmaceutical composition in admixture with a pharmaceutical carrier or vehicle;
(b) a naAEA, in a pharmaceutical composition in admixture with a pharmaceutical carrier or vehicle; and
(c) a nsPAChA selected form the group consisting of quaternary ammonium nsPAChAs, sulfonium nsPAChAs, solifenacin and pharmaceutically acceptable salts and solvates thereof, propiverine and pharmaceutically acceptable salts and solvates thereof, oxyphencyclimine and pharmaceutically acceptable salts and solvates thereof, tolterodine and pharmaceutically acceptable salts and solvates thereof, fesoterodine and pharmaceutically acceptable salts and solvates thereof; and TTS-oxybutynin and pharmaceutically acceptable salts thereof, in a pharmaceutical composition in admixture with a pharmaceutical carrier or vehicle.

According to this third embodiment, another combination is a combination comprising or consisting essentially of
(a) a MCRA, in a pharmaceutical composition in admixture with a pharmaceutical carrier or vehicle;
(b) a naAEA, in a pharmaceutical composition in admixture with a pharmaceutical carrier or vehicle; and
(c) a quaternary ammonium or a sulfonium nsPAChA of formula I

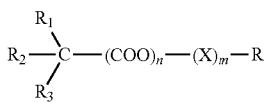

(I)

wherein
R is a radical selected from the group consisting of those of formulas (a)-(e)

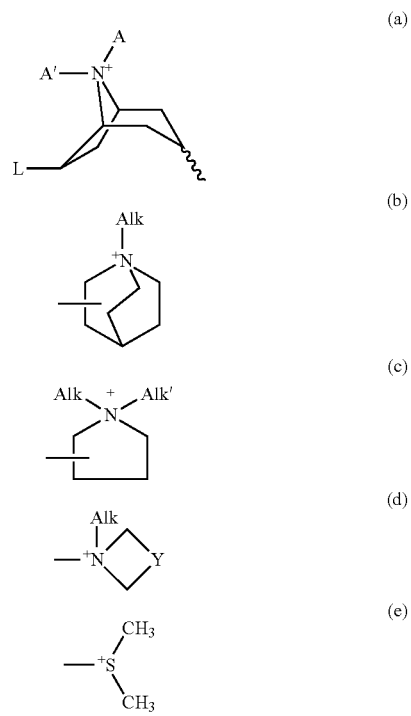

A being methyl and A' being $(C_1-C_4)$alkyl or 2-fluoroethyl group or A and A' forming a 1,4-butylene or 1,5-pentylene chain, L being hydrogen or methoxy, Alk and Alk' each being $(C_1-C_4)$alkyl and Y being a bivalent radical selected from the group consisting of 1,2-ethylene, 1,3-propylene, 1,4-butylene and 2-oxa-1,3-propylene; the corresponding counter ion being a pharmaceutically acceptable anion, such as a chloro, bromo, iodo, tartrate, hydrogen tartrate, succinate, maleate, fumarate, sulfate, hydrogen sulfate or methylsulfate anion;

n and m, independently, are zero or 1;

X is a $(C_2-C_3)$alkylene group;

$R_1$ and $R_2$ are each phenyl, cyclopentyl, cyclohexyl, 1-cyclohexenyl, 2-thienyl and, when R is a radical (a), also each represents $(C_1-C_4)$alkyl;

$R_3$ is H or OH or, only when R is a radical (a), also a COOAlk group, Alk being a $(C_1-C_4)$alkyl group, in a pharmaceutical composition in admixture with a pharmaceutical carrier or vehicle.

Preferably, in the above formula I, at least one of m and n is 1.

As a particular aspect of this embodiment, the invention provides a combination comprising or consisting essentially of, as Components:
(a) a MCRA;
(b) a naAEA; and
(c) a nsPAChA selected from the group consisting of anisotropine pharmaceutically acceptable quaternary salts, butylscopolamine pharmaceutically acceptable salts, cimetropium pharmaceutically acceptable salts, clidinium pharmaceutically acceptable salts, fesoterodine and pharmaceutically acceptable salts thereof, glycopyrronium pharmaceutically acceptable salts, otilonium pharmaceutically acceptable salts, oxyphencyclimine and pharmaceutically acceptable salts thereof, prifinium pharmaceutically acceptable salts, propiverine and pharmaceutically acceptable salts thereof, solifenacin and pharmaceutically acceptable salts thereof, tolterodine and pharmaceutically acceptable salts thereof, timepidium pharmaceutically acceptable salts, trospium pharmaceutically acceptable salts, TTS-oxybutynin; and valethamate pharmaceutically acceptable salts.

According to this particular aspect, of this embodiment, said nsPAChA of said combination is selected from the group consisting of glycopyrronium pharmaceutically acceptable salts, at a dose that is equivalent to from 1 mg to 24 mg of glycopyrronium bromide; propiverine and pharmaceutically acceptable salts thereof, at a dose that is equivalent to from 15 mg to 240 mg of propiverine hydrobromide; solifenacin and pharmaceutically acceptable salts thereof, at a dose that is equivalent to from 5 mg to 40 mg of solifenacin succinate; trospium pharmaceutically acceptable salts, at a dose that is equivalent to from 20 mg to 480 mg of trospium chloride; and TTS-oxybutynin, at a dose of from 3.9 mg to 7.8 mg. Said doses are referred to daily administered doses.

The above therapeutic doses are administered in a pharmaceutical compositions comprising said nsPAChAs in admixture with a pharmaceutical carrier or vehicle.

Thus, this particular aspect of this third embodiment provides a pharmaceutical combination comprising:
(a) a MCRA;
(b) a naAEA; and
(c) a pharmaceutical composition comprising a nsPAChA selected from the group consisting of glycopyrronium pharmaceutically acceptable salts, in an amount that is equivalent to from 0.5 mg to 16 mg of glycopyrronium bromide; propiverine and pharmaceutically acceptable salts thereof, in an amount that is equivalent to from 7.5 mg to 240 mg of propiverine hydrobromide; solifenacin and pharmaceutically acceptable salts thereof, in an amount that is equivalent to from 5 mg to 60 mg, preferably from 5 mg to 40 mg, of solifenacin succinate; trospium pharmaceutically acceptable salts, in an amount that is equivalent to from 20 mg to 480 mg of trospium chloride; and TTS-oxybutynin, in a released amount of from 3.9 mg/24 h to 7.8 mg/24 h, in admixture with a pharmaceutical carrier or vehicle.

This combination preferably provides the MCRA Component (a) and, respectively, the naAEA Component (b) each in a pharmaceutical composition in admixture with a pharmaceutical carrier or vehicle or in other fixed doses combinations, as illustrated herein below.

An advantageous combination according to this third embodiment is a combination comprising or consisting essentially of, as Components:
(a) a MCRA, in a pharmaceutical composition in admixture with a pharmaceutical carrier or vehicle;
(b) a naAEA, in a pharmaceutical composition in admixture with a pharmaceutical carrier or vehicle and
(c) a quaternary ammonium nsPAChA selected form the group consisting of trospium chloride, glycopyrronium bromide, cimetropium bromide, otilonium bromide, prifinium bromide, timepidium bromide, scopolamine methobromide, scopolamine butylbromide, scopolamine methonitrate, isopropamide iodide, valethamate bromide, atropine methobromide, atropine methonitrate, diponium bromide, pipenzolate bromide, penthienate bromide, benactizine methobromide, diphemanil, emeprioum bromide and dibutoline sulfate, in a pharmaceutical composition in admixture with a pharmaceutical carrier or vehicle.

A further advantageous combination according to this third embodiment is a combination comprising or consisting essentially of, as Components:
(a) a MCRA, in a pharmaceutical composition in admixture with a pharmaceutical carrier or vehicle;
(b) a naAEA, in a pharmaceutical composition in admixture with a pharmaceutical carrier or vehicle; and
(c) a nsPAChA selected from the group consisting of anisotropine methylbromide, in an amount from 25 mg to 300 mg, advantageously from 60 mg to 300 mg, normally from 60 mg to 200 mg; cimetropium bromide, in an amount from 25 mg to 300 mg, advantageously from 60 mg to 300 mg, normally from 60 mg to 200 mg; clidinium bromide, in an amount from 1.25 mg to 15 mg, advantageously from 3 mg to 15 mg, normally from 3 mg to 10 mg; fesoterodine fumarate, in an amount from more than 4 mg to 480 mg, advantageously from 9.6 mg to 480 mg, normally from 9.6 mg to 320 mg; glycopyrronium bromide, in an amount from 1 mg to 16 mg, advantageously from 2.4 mg to 12 mg, normally from 2.4 mg to 8 mg; otilonium bromide, in an amount from 20 mg to 240 mg, advantageously from 48 mg to 240 mg, normally from 48 mg to 160 mg; oxyphencyclimine hydrochloride, in an amount from 5 mg to 60 mg, advantageously from 12 mg to 60 mg, normally from 12 mg to 40 mg; prifinium bromide, in an amount from 15 mg to 180 mg, advantageously from 36 mg to 180 mg, normally from 36 mg to 120 mg; propiverine hydrochloride, in an amount from 7.5 mg to 180 mg, advantageously from 17.5 mg to 180 mg, normally from 17.5 mg to 120 mg; solifenacin succinate, in an amount from 5 mg to 60 mg, advantageously from 10 mg to 40 mg, normally from 12 mg to 30 mg, preferably from 12 mg to 25 mg or of 21 mg; timepidium bromide, in an amount from 15 mg to 180 mg, advantageously from 36 mg to 180 mg, normally from 36 mg to 120 mg; trospium chloride, in an amount 10 mg to 360 mg, advantageously from 24 mg to 360 mg, normally from 24 mg to 180 mg, in a pharmaceutical composition in admixture with a pharmaceutical carrier; and oxybutynin in a transdermal patch releasing from 3.9 mg/24 h to 7.8 mg/24 h oxybutynin; in a pharmaceutical composition in admixture with a pharmaceutical carrier or vehicle.

A further advantageous combination according to this third embodiment is a combination comprising or consisting essentially of, as Components:
(a) a MCRA, in a pharmaceutical composition in admixture with a pharmaceutical carrier or vehicle;
(b) a naAEA, in a pharmaceutical composition in admixture with a pharmaceutical carrier or vehicle; and
(c) a nsPAChA selected from the group consisting of propiverine hydrochloride, in an amount of from 18 mg to 90 mg in admixture with a pharmaceutical carrier in an IR-formulated composition or in an amount of from 36 mg to 180 mg in admixture with a pharmaceutical carrier in an ER-formulated composition, trospium chloride, in an amount of from 24 mg to 80 mg, in admixture with a pharmaceutical carrier in an IR-formulated composition or in an amount of from 72 mg to 240 mg, in admixture with a pharmaceutical carrier in an ER-formulated composition; solifenacin succinate, in an amount selected from the group consisting of from 5 mg to 60 mg, from 10 mg to 40 mg, from 12 mg to 30 mg, from 12 mg to 25 mg, and 21 mg, in admixture with a pharmaceutical carrier in an IR-formulated composition and oxybutynin, in admixture with a pharmaceutical carrier in a transdermal patch releasing from 3.9 mg/24 h to 7.8 mg/24 h oxybutynin; in a pharmaceutical composition in admixture with a pharmaceutical carrier or vehicle.

In said combination, Component (c) preferably is a nsPAChA selected from the group consisting of anisotropine methylbromide, in an amount of from 120 mg to 300 mg; butylscopolamine bromide, in an amount of from 12 mg to 40 mg; cimetropium bromide, in an amount of from 55 mg to 200 mg; clidinium bromide, in an amount of from 3 mg to 10 mg; fesoterodine fumarate, in an amount of from 9.6 mg to 32 mg; glycopyrronium bromide, in an amount of from 2.4 mg to 8 mg; otilonium bromide, in an amount of from 48 mg to 160 mg; oxyphencyclimine, in an amount of from 18 mg to 60 mg; prifinium bromide, in an amount of from 36 mg to 120 mg; propiverine hydrochloride IR, in an amount of from 18 mg to 90 mg; propiverine ER, in an amount of from 36 mg to 180 mg; solifenacin succinate, in an amount selected from the group consisting of from 5 mg to 60 mg, from 10 mg to 40 mg, from 12 mg to 30 mg, from 12 mg to 25 mg, and 21 mg; tolterodine tartrate, in an amount of from 4.8 mg to 16 mg; timepidium bromide, in an amount of from 36 mg to 120 mg; trospium chloride, in an amount of from 24 mg to 240 mg; oxybutynin transdermal patch releasing 3.9 mg/24 h oxybutynin; and valethamate bromide, in an amount of from 12 mg to 40 mg.

The pharmaceutical combinations according to this third embodiment are indicated in the treatment of hypocholinergic disorders and even high doses of a MCRA Component (a), may be present to improve said symptoms without adverse effects to a greater extent.

Thus, the invention provides a method for treating hypocholinergic disorders, which comprises administering to a patient in need of said treatment the above-illustrated combinations according to this third embodiment. In such a treatment, Component (a), Component (b) and Component (c) of the combination may be administered simultaneously or sequentially to said patient, Component (a) being indifferently administered before or after Component (b) and Component (c). Components (a), Component (b) and Component (c) may also be administered by the same or a different administration route.

According to a fourth embodiment, an advantageous combination may be a combination comprising or consisting essentially of (a) a pharmaceutical composition comprising cevimeline, as free base or as its hydrochloride hemihydrate, in an amount of from 36 mg to 180 mg, in an IR-formulated oral composition in admixture with a pharmaceutical carrier or vehicle;
(b) a pharmaceutical composition comprising a naAEA selected from the group consisting of alosetron and pharmaceutically acceptable salts and solvates thereof, azasetron and pharmaceutically acceptable salts and solvates thereof; ondansetron and pharmaceutically acceptable salts and solvates thereof; granisetron and pharmaceutically acceptable salts and solvates thereof; dolasetron and pharmaceutically acceptable salts and solvates thereof, ramosetron and pharmaceutically acceptable salts and solvates thereof; tropisetron and pharmaceutically acceptable salts and solvates thereof; and palonosetron and pharmaceutically acceptable salts and solvates thereof, domperidone and pharmaceutically acceptable salts and solvates thereof such as the maleate; chlorpromazine and pharmaceutically acceptable salts and solvates thereof such as the hydrochloride; prochlorperazine and its salts and solvates, particularly the dimaleate and the dimesylate; promethazine and pharmaceutically acceptable salts and solvates thereof such as the hydrochloride; metoclopramide and pharmaceutically acceptable salts and solvates thereof such as the hydrochloride monohydrate, bromopride and pharmaceutically acceptable salts and solvates thereof such as the monohydrochloride or the dihydrochloride monohydrate, alizapride and pharmaceutically acceptable salts and solvates thereof such as the hydrochloride, and clebopride and pharmaceutically acceptable salts and solvates thereof such as the malate and the hydrochloride monohydrate, dronabinol, nabilone, aprepitant, netupitant; rolapitant; and casopitant, in admixture with a pharmaceutical carrier or vehicle; and
(c) a pharmaceutical composition comprising a nsPAChA selected from the group consisting of glycopyrronium pharmaceutically acceptable salts; propiverine; pharmaceutically acceptable salts of propiverine; solifenacin; pharmaceutically acceptable salts of solifenacin; trospium pharmaceutically acceptable salts; and TTS-oxybutynin, in admixture with a pharmaceutical carrier or vehicle.

Another advantageous combination may be a combination comprising or consisting essentially of (a) a pharmaceutical composition comprising cevimeline, as free base or as its hydrochloride hemihydrate, in an amount of from 36 mg to 180 mg, in an IR-formulated oral composition in admixture with a pharmaceutical carrier or vehicle;
(b) a pharmaceutical composition comprising a naAEA selected from the group consisting of alosetron and pharmaceutically acceptable salts and solvates thereof, azasetron and pharmaceutically acceptable salts and solvates thereof; ondansetron and pharmaceutically acceptable salts and solvates thereof; granisetron and pharmaceutically acceptable salts and solvates thereof; dolasetron and pharmaceutically acceptable salts and solvates thereof, ramosetron and pharmaceutically acceptable salts and solvates thereof; tropisetron and pharmaceutically acceptable salts and solvates thereof; and palonosetron and pharmaceutically acceptable salts and solvates thereof, domperidone and pharmaceutically acceptable salts and solvates thereof such as the maleate; chlorpromazine and pharmaceutically acceptable salts and solvates thereof such as the hydrochloride; prochlorperazine and its salts and solvates, particularly the dimaleate and the dimesylate; promethazine and pharmaceutically acceptable salts and solvates thereof such as the hydrochloride; metoclopramide and pharmaceutically acceptable salts and solvates thereof such as the hydrochloride monohydrate, bromopride and pharmaceutically acceptable salts and solvates thereof such as the monohydrochloride or the dihydrochloride monohydrate, alizapride and pharmaceutically acceptable salts and solvates thereof such as the hydrochloride, and clebopride and pharmaceutically acceptable salts and solvates thereof such as the malate and the hydrochloride monohydrate, dronabinol, nabilone, aprepitant, netupitant; rolapitant; and casopitant, in admixture with a pharmaceutical carrier or vehicle; and
(c) a pharmaceutical composition comprising nsPAChA being preferably selected from the group consisting of anisotropine methylbromide, butylscopolamine bromide, cimetropium bromide, clidinium bromide, fesoterodine fumarate, glycopyrronium bromide, otilonium bromide, oxyphencyclimine hydrochloride, prifinium bromide, propiverine hydrochloride, solifenacin succinate, tolterodine tartrate, timepidium bromide, trospium chloride;

TTS-oxybutynin and valethamate bromide; in admixture with a pharmaceutical carrier or vehicle.

An advantageous combination according to this fourth embodiment may be a combination comprising or consisting essentially of, as Components:
(a) a pharmaceutical composition comprising cevimeline, as free base or as its hydrochloride hemihydrate, in an amount of from 36 mg to 180 mg, in admixture with a pharmaceutical carrier or vehicle.
(b) a pharmaceutical composition comprising a naAEA selected from the group consisting of alosetron hydrochloride, in an amount (in alosetron) of from 0.25 mg to 6 mg; azasetron hydrochloride, in an amount (in azasetron) of from 5 mg to 60 mg; dolasetron mesylate, in an amount (in dolasetron) of from 25 mg to 600 mg; granisetron hydrochloride, in an amount (in granisetron) of from 0.5 mg to 6 mg; ondansetron hydrochloride dihydrate, in an amount (in ondansetron) of from 2 mg to 64 mg; palonosetron hydrochloride, in an amount (in palonosetron) of from 0.25 mg to 3 mg; ramosetron hydrochloride, in an amount (in ramosetron) of from 0.0125 mg to 0.3 mg, tropisetron hydrochloride, in an amount (in tropisetron) of from 2.5 mg to 30 mg; domperidone and pharmaceutically acceptable salts and solvates thereof, in an amount (in domperidone) of from 5 mg to 60 mg; haloperidol, in an amount of from 0.5 mg to 60 mg; chlorpromazine hydrochloride, in an amount (in chlorpromazine) of from 12.5 mg to 600 mg; prochlorperazine dimaleate, in an amount (in prochlorperazine) of from 2.5 mg to 30 mg; metoclopramide monohydrochloride monohydrate, in an amount (in metoclopramide) of from 5 mg to 60 mg; bromopride monohydrochloride or dihydrochloride monohydrate, in an amount (in bromopride) of from 5 mg to 60 mg; clebopride hydrogen malate or hydrochloride monohydrate, in an amount (in clebopride) of from 0.25 mg to 3 mg; levosulpiride, in an amount of from 12.5 mg to 600 mg; alizapride hydrochloride, in an amount (in alizapride) of from 25 mg to 300 mg; trimethobenzamide monohydrochloride, in an amount (in trimethobenzamide) of from 50 mg to 600 mg; meclizine (also called meclozine) and pharmaceutically acceptable salts and solvates thereof, in an amount (in meclizine) of from 6.25 mg to 300 mg; promethazine hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant, in an amount of from 25 mg to 300 mg; in a pharmaceutical composition in admixture with a pharmaceutical carrier or vehicle; and
(c) a pharmaceutical composition comprising a nsPAChA selected from the group consisting of glycopyrronium pharmaceutically acceptable salts, in an amount that is equivalent to from 0.5 mg to 16 mg of glycopyrronium bromide; propiverine and pharmaceutically acceptable salts thereof, in an amount that is equivalent to from 7.5 mg to 240 mg of propiverine hydrobromide; solifenacin and pharmaceutically acceptable salts thereof, in an amount that is equivalent to from 5 mg to 60 mg, preferably from 5 mg to 40 mg, of solifenacin succinate; trospium pharmaceutically acceptable salts, in an amount that is equivalent to from 20 mg to 480 mg of trospium chloride; and TTS-oxybutynin, in a released amount of from 3.9 mg/24 h to 7.8 mg/24 h, in admixture with a pharmaceutical carrier or vehicle.

Another advantageous combination according to this fourth embodiment may be a combination comprising or consisting essentially of, as Components:
(a) a pharmaceutical composition comprising cevimeline, as free base or as its hydrochloride hemihydrate, in an amount of from 36 mg to 180 mg, in admixture with a pharmaceutical carrier or vehicle.
(b) a pharmaceutical composition comprising a naAEA selected from the group consisting of alosetron hydrochloride, in an amount (in alosetron) of from 0.25 mg to 6 mg; azasetron hydrochloride, in an amount (in azasetron) of from 5 mg to 60 mg; dolasetron mesylate, in an amount (in dolasetron) of from 25 mg to 600 mg; granisetron hydrochloride, in an amount (in granisetron) of from 0.5 mg to 6 mg; ondansetron hydrochloride dihydrate, in an amount (in ondansetron) of from 2 mg to 64 mg; palonosetron hydrochloride, in an amount (in palonosetron) of from 0.25 mg to 3 mg; ramosetron hydrochloride, in an amount (in ramosetron) of from 0.0125 mg to 0.3 mg, tropisetron hydrochloride, in an amount (in tropisetron) of from 2.5 mg to 30 mg; domperidone and pharmaceutically acceptable salts and solvates thereof, in an amount (in domperidone) of from 5 mg to 60 mg; haloperidol, in an amount of from 0.5 mg to 60 mg; chlorpromazine hydrochloride, in an amount (in chlorpromazine) of from 12.5 mg to 600 mg; prochlorperazine dimaleate, in an amount (in prochlorperazine) of from 2.5 mg to 30 mg; metoclopramide monohydrochloride monohydrate, in an amount (in metoclopramide) of from 5 mg to 60 mg; bromopride monohydrochloride or dihydrochloride monohydrate, in an amount (in bromopride) of from 5 mg to 60 mg; clebopride hydrogen malate or hydrochloride monohydrate, in an amount (in clebopride) of from 0.25 mg to 3 mg; levosulpiride, in an amount of from 12.5 mg to 600 mg; alizapride hydrochloride, in an amount (in alizapride) of from 25 mg to 300 mg; trimethobenzamide monohydrochloride, in an amount (in trimethobenzamide) of from 50 mg to 600 mg; meclizine (also called meclozine) and pharmaceutically acceptable salts and solvates thereof, in an amount (in meclizine) of from 6.25 mg to 300 mg; promethazine hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant, in an amount of from 25 mg to 300 mg; in a pharmaceutical composition in admixture with a pharmaceutical carrier or vehicle; and
(c) a pharmaceutical composition comprising a nsPAChA selected from the group consisting of anisotropine methylbromide, in an amount of from 60 mg to 300 mg, normally from 60 mg to 200 mg; butylscopolamine bromide in an amount of from 12 mg to 60 mg, normally from 12 mg to 40; cimetropium bromide, in an amount of from 55 mg to 200 mg; clidinium bromide in an amount of from 3 mg to 15 mg, normally from 3 mg to 10 mg; fesoterodine fumarate, in an amount of from 9.6 mg to 32 mg; glycopyrronium bromide in an amount of from 2.2 to 12 mg, normally from 2.2 to 8 mg; otilonium bromide in an amount of from 48 mg to 240 mg, normally from 48 mg to 160 mg; prifinium bromide in an amount of from 36 mg to 180 mg, normally from 36 mg to 120 mg; propiverine hydrochloride, in an amount of from 18 mg to 180 mg; solifenacin succinate, in an amount selected from the group consisting of from 5 mg to 60 mg, from 10 mg to 40 mg, from 12 mg to 30 mg, from 12 mg to 25 mg, and 21 mg; tolterodine tartrate, in an amount of from 4.8 mg to 16 mg; timepidium bromide in an amount of from 36 mg to 180 mg, normally from 36 mg to 120 mgr; trospium chloride, in an amount of from 24 mg to 240 mg; and valethamate bromide in an amount of from 12 mg to 60 mg and MK-76 22 in an amount consisting of from more than 5 mg to 15 mg, from more than 15 mg to 45 mg, from more than 45 mg to 270 mg, from more than 15 mg to 225 mg, from more than 45 mg to 225 mg, and from 54 mg to 180 mg;

in admixture with a pharmaceutical carrier or vehicle.

Another advantageous combination according to this fourth embodiment may be a combination comprising or consisting essentially of, as Components:

(a) a pharmaceutical composition comprising cevimeline, as free base or as its hydrochloride hemihydrate, in an amount of from 36 mg to 180 mg, in admixture with a pharmaceutical carrier or vehicle;

(b) a pharmaceutical composition comprising a naAEA selected from the group consisting of alosetron hydrochloride, in an amount (in alosetron) of from 0.25 mg to 6 mg; azasetron hydrochloride, in an amount (in azasetron) of from 5 mg to 60 mg; dolasetron mesylate, in an amount (in dolasetron) of from 25 mg to 600 mg; granisetron hydrochloride, in an amount (in granisetron) of from 0.5 mg to 6 mg; ondansetron hydrochloride dihydrate, in an amount (in ondansetron) of from 2 mg to 64 mg; palonosetron hydrochloride, in an amount (in palonosetron) of from 0.25 mg to 3 mg; ramosetron hydrochloride, in an amount (in ramosetron) of from 0.0125 mg to 0.3 mg, tropisetron hydrochloride, in an amount (in tropisetron) of from 2.5 mg to 30 mg; domperidone and pharmaceutically acceptable salts and solvates thereof, in an amount (in domperidone) of from 5 mg to 60 mg; haloperidol, in an amount of from 0.5 mg to 60 mg; chlorpromazine hydrochloride, in an amount (in chlorpromazine) of from 12.5 mg to 600 mg; prochlorperazine dimaleate, in an amount (in prochlorperazine) of from 2.5 mg to 30 mg;

metoclopramide monohydrochloride monohydrate, in an amount (in metoclopramide) of from 5 mg to 60 mg; bromopride monohydrochloride or dihydrochloride monohydrate, in an amount (in bromopride) of from 5 mg to 60 mg; clebopride hydrogen malate or hydrochloride monohydrate, in an amount (in clebopride) of from 0.25 mg to 3 mg; levosulpiride, in an amount of from 12.5 mg to 600 mg; alizapride hydrochloride, in an amount (in alizapride) of from 25 mg to 300 mg; trimethobenzamide monohydrochloride, in an amount (in trimethobenzamide) of from 50 mg to 600 mg; meclizine (also called meclozine) and pharmaceutically acceptable salts and solvates thereof, in an amount (in meclizine) of from 6.25 mg to 300 mg; promethazine hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant, in an amount of from 25 mg to 300 mg; in a pharmaceutical composition in admixture with a pharmaceutical carrier or vehicle; and (c) a pharmaceutical composition comprising a nsPAChA consisting of oxybutynin in a pharmaceutical composition in admixture with a pharmaceutical carrier or vehicle in a patch releasing from 3.9 mg/24 h to 7.8 mg/24 h oxybutynin.

Preferably, according to this fourth embodiment, the pharmaceutical composition Component (a) comprises cevimeline, hydrochloride hemihydrate, in an amount of from 36 mg to 180 mg, in an IR-formulated oral composition in admixture with a pharmaceutical carrier or vehicle.

According to a fifth embodiment, an advantageous MCRA/naAEA/nsPAChA combination according to the present invention may be a combination comprising or consisting essentially of (a) a pharmaceutical composition comprising xanomeline, as free base, as oxalate or as L-tartrate, in an amount of from 90 mg to 450 mg, normally from 90 mg to 300 mg, in admixture with a pharmaceutical carrier. in admixture with a pharmaceutical carrier or vehicle;

(b) a pharmaceutical composition comprising a naAEA selected from the group consisting of alosetron and pharmaceutically acceptable salts and solvates thereof, azasetron and pharmaceutically acceptable salts and solvates thereof; ondansetron and pharmaceutically acceptable salts and solvates thereof; granisetron and pharmaceutically acceptable salts and solvates thereof; dolasetron and pharmaceutically acceptable salts and solvates thereof, ramosetron and pharmaceutically acceptable salts and solvates thereof; tropisetron and pharmaceutically acceptable salts and solvates thereof; and palonosetron and pharmaceutically acceptable salts and solvates thereof, domperidone and pharmaceutically acceptable salts and solvates thereof such as the maleate; chlorpromazine and pharmaceutically acceptable salts and solvates thereof such as the hydrochloride; prochlorperazine and its salts and solvates, particularly the dimaleate and the dimesylate; promethazine and pharmaceutically acceptable salts and solvates thereof such as the hydrochloride; metoclopramide and pharmaceutically acceptable salts and solvates thereof such as the hydrochloride monohydrate, bromopride and pharmaceutically acceptable salts and solvates thereof such as the monohydrochloride or the dihydrochloride monohydrate, alizapride and pharmaceutically acceptable salts and solvates thereof such as the hydrochloride, and clebopride and pharmaceutically acceptable salts and solvates thereof such as the malate and the hydrochloride monohydrate, dronabinol, nabilone, aprepitant, netupitant, rolapitant, and casopitant, in admixture with a pharmaceutical carrier or vehicle; and (c) a pharmaceutical composition comprising a nsPAChA selected from the group consisting of anisotropine pharmaceutically acceptable quaternary salts, butylscopolamine pharmaceutically acceptable salts, cimetropium pharmaceutically acceptable salts, clidinium pharmaceutically acceptable salts, fesoterodine and pharmaceutically acceptable salts thereof, glycopyrronium pharmaceutically acceptable salts, otilonium pharmaceutically acceptable salts, oxyphencyclimine and pharmaceutically acceptable salts thereof, prifinium pharmaceutically acceptable salts, propiverine and pharmaceutically acceptable salts thereof, solifenacin and pharmaceutically acceptable salts thereof, tolterodine and pharmaceutically acceptable salts thereof, timepidium pharmaceutically acceptable salts, trospium pharmaceutically acceptable salts, TTS-oxybutynin; and valethamate pharmaceutically acceptable salts; and TTS-oxybutynin, in admixture with a pharmaceutical carrier or vehicle.

Another advantageous combination according to this fifth embodiment may be a combination comprising or consisting essentially of, as Components (a) a pharmaceutical composition comprising xanomeline, as free base, as oxalate or as L-tartrate, in an amount of from 90 mg to 450 mg, normally from 90 mg to 300 mg, in admixture with a pharmaceutical carrier. in admixture with a pharmaceutical carrieror vehicle;

(b) a pharmaceutical composition comprising a naAEA selected from the group consisting of alosetron and pharmaceutically acceptable salts and solvates thereof, azasetron and pharmaceutically acceptable salts and solvates thereof; ondansetron and pharmaceutically acceptable salts and solvates thereof; granisetron and pharmaceutically acceptable salts and solvates thereof; dolasetron and pharmaceutically acceptable salts and solvates thereof, ramosetron and pharmaceutically acceptable salts and solvates thereof; tropisetron and pharmaceutically acceptable salts and solvates thereof; and palonosetron and pharmaceutically acceptable salts and solvates thereof, domperidone and pharmaceutically acceptable salts and solvates thereof such as the maleate; chlorpromazine and pharmaceutically acceptable salts and solvates thereof such as the hydrochloride; prochlorperazine and its salts and solvates, particularly the dimaleate and the dimesylate; promethazine and pharmaceutically acceptable salts and solvates thereof such as the hydrochloride; metoclopramide and pharmaceutically acceptable salts and solvates thereof such as the hydrochloride monohydrate, bromopride and pharmaceutically acceptable salts and solvates thereof such as the monohydrochloride or the dihydrochloride monohydrate, alizapride and pharmaceutically acceptable salts and solvates thereof such as the hydrochloride, and clebopride and pharmaceutically acceptable salts and solvates thereof such as the malate and the hydrochloride monohydrate, dronabinol, nabilone, aprepitant, netupitant, rolapitant, and casopitant in admixture with a pharmaceutical carrier or vehicle; and (c) a pharmaceutical composition comprising a nsPAChA being preferably selected from the group consisting of anisotropine methylbromide, butylscopolamine bromide, cimetropium bromide, clidinium bromide, fesoterodine fumarate, glycopyrronium bromide, otilonium bromide, oxyphencyclimine hydrochloride, prifinium bromide, propiverine hydrochloride, solifenacin succinate, tolterodine tartrate, timepidium bromide, trospium chloride; TTS-oxybutynin and valethamate bromide; in admixture with a pharmaceutical carrier or vehicle.

An advantageous combination according to this fifth embodiment may be a combination comprising or consisting essentially of, as Components:

(a) a pharmaceutical composition comprising xanomeline, as free base, as oxalate or as L-tartrate, in an amount of from 90 mg to 450 mg, normally from 90 mg to 300 mg, in admixture with a pharmaceutical carrier or vehicle;

(b) a pharmaceutical composition comprising a naAEA selected from the group consisting of alosetron hydrochloride, in an amount (in alosetron) of from 0.25 mg to 6 mg; azasetron hydrochloride, in an amount (in azasetron) of from 5 mg to 60 mg; dolasetron mesylate, in an amount (in dolasetron) of from 25 mg to 600 mg; granisetron hydrochloride, in an amount (in granisetron) of from 0.5 mg to 6 mg; ondansetron hydrochloride dihydrate, in an amount (in ondansetron) of from 2 mg to 64 mg; palonosetron hydrochloride, in an amount (in palonosetron) of from 0.25 mg to 3 mg; ramosetron hydrochloride, in an amount (in ramosetron) of from 0.0125 mg to 0.3 mg, tropisetron hydrochloride, in an amount (in tropisetron) of from 2.5 mg to 30 mg; domperidone and pharmaceutically acceptable salts and solvates thereof, in an amount (in domperidone) of from 5 mg to 60 mg; haloperidol, in an amount of from 0.5 mg to 60 mg; chlorpromazine hydrochloride, in an amount (in chlorpromazine) of from 12.5 mg to 600 mg; prochlorperazine dimaleate, in an amount (in prochlorperazine) of from 2.5 mg to 30 mg; metoclopramide monohydrochloride monohydrate, in an amount (in metoclopramide) of from 5 mg to 60 mg; bromopride monohydrochloride or dihydrochloride monohydrate, in an amount (in bromopride) of from 5 mg to 60 mg; clebopride hydrogen malate or hydrochloride monohydrate, in an amount (in clebopride) of from 0.25 mg to 3 mg; levosulpiride, in an amount of from 12.5 mg to 600 mg; alizapride hydrochloride, in an amount (in alizapride) of from 25 mg to 300 mg; trimethobenzamide monohydrochloride, in an amount (in trimethobenzamide) of from 50 mg to 600 mg; meclizine (also called meclozine) and pharmaceutically acceptable salts and solvates thereof, in an amount (in meclizine) of from 6.25 mg to 300 mg; promethazine hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant, in an amount of from 25 mg to 300 mg; in a pharmaceutical composition in admixture with a pharmaceutical carrier or vehicle; and (c) a pharmaceutical composition comprising a nsPAChA selected from the group consisting of glycopyrronium pharmaceutically acceptable salts, in an amount that is equivalent to from 0.5 mg to 16 mg of glycopyrronium bromide; propiverine and pharmaceutically acceptable salts thereof, in an amount that is equivalent to from 7.5 mg to 240 mg of propiverine hydrobromide; solifenacin and pharmaceutically acceptable salts thereof, in an amount that is equivalent to from 5 mg to 60 mg, preferably from 5 mg to 40 mg, of solifenacin succinate; trospium pharmaceutically acceptable salts, in an amount that is equivalent to from 20 mg to 480 mg of trospium chloride; and TTS-oxybutynin, in a released amount of from 3.9 mg/24 h to 7.8 mg/24 h, in admixture with a pharmaceutical carrier or vehicle.

Another advantageous combination according to this fifth embodiment may be a combination comprising or consisting essentially of, as Components:

(a) a pharmaceutical composition comprising xanomeline, as free base, as oxalate or as L-tartrate, in an amount of from 90 mg to 450 mg, normally from 90 mg to 300 mg, in admixture with a pharmaceutical carrier or vehicle;

(b) a pharmaceutical composition comprising a naAEA selected from the group consisting of alosetron hydrochloride, in an amount (in alosetron) of from 0.25 mg to 6 mg; azasetron hydrochloride, in an amount (in azasetron) of from 5 mg to 60 mg; dolasetron mesylate, in an amount (in dolasetron) of from 25 mg to 600 mg; granisetron hydrochloride, in an amount (in granisetron) of from 0.5 mg to 6 mg; ondansetron hydrochloride dihydrate, in an amount (in ondansetron) of from 2 mg to 64 mg; palonosetron hydrochloride, in an amount (in palonosetron) of from 0.25 mg to 3 mg; ramosetron hydrochloride, in an amount (in ramosetron) of from 0.0125 mg to 0.3 mg, tropisetron hydrochloride, in an amount (in tropisetron) of from 2.5 mg to 30 mg; domperidone and pharmaceutically acceptable salts and solvates thereof, in an amount (in domperidone) of from 5 mg to 60 mg; haloperidol, in an amount of from 0.5 mg to 60 mg;

chlorpromazine hydrochloride, in an amount (in chlorpromazine) of from 12.5 mg to 600 mg; prochlorperazine dimaleate, in an amount (in prochlorperazine) of from 2.5 mg to 30 mg; metoclopramide monohydrochloride monohydrate, in an amount (in metoclopramide) of from 5 mg to 60 mg; bromopride monohydrochloride or dihydrochloride monohydrate, in an amount (in bromopride) of from 5 mg to 60 mg; clebopride hydrogen malate or hydrochloride monohydrate, in an amount (in clebopride) of from 0.25 mg to 3 mg; levosulpiride, in an amount of from 12.5 mg to 600 mg; alizapride hydrochloride, in an amount (in alizapride) of from 25 mg to 300 mg; trimethobenzamide monohydrochloride, in an amount (in trimethobenzamide) of from 50 mg to 600 mg; meclizine (also called meclozine) and pharmaceutically acceptable salts and solvates thereof, in an amount (in meclizine) of from 6.25 mg to 300 mg; promethazine hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant, in an amount of from 25 mg to 300 mg; in a pharmaceutical composition in admixture with a pharmaceutical carrier or vehicle; and (c) a pharmaceutical composition comprising a nsPAChA selected from the group consisting of anisotropine methylbromide, in an amount of from 60 mg to 300 mg, normally from 60 mg to 200 mg; butylscopolamine bromide in an amount of from 12 mg to 60 mg, normally from 12 mg to 40; cimetropium bromide, in an amount of from 25 mg to 300 mg, normally from 55 mg to 200 mg; clidinium bromide in an amount of from 3 mg to 15 mg, normally from 3 mg to 10 mg; fesoterodine fumarate, in an amount of from 9.6 mg to 32 mg; glycopyrronium bromide in an amount of from 2.2 to 12 mg, normally from 2.2 to 8 mg; otilonium bromide in an amount of from 48 mg to 240 mg, normally from 48 mg to 160 mg; prifinium bromide in an amount of from 36 mg to 180 mg, normally from 36 mg to 120 mg; propiverine hydrochloride, in an amount of from 18 mg to 180 mg; solifenacin succinate, in an amount selected from the group consisting of from 5 mg to 60 mg, from 10 mg to 40 mg, from 12 mg to 30 mg, from 12 mg to 25 mg, and 21 mg; tolterodine tartrate, in an amount of from 4.8 mg to 16 mg; timepidium bromide in an amount of from 36 mg to 180 mg, normally from 36 mg to 120 mgr; trospium chloride, in an amount of from 24 mg to 240 mg; and valethamate bromide in an amount of from 12 mg to 60 mg, in admixture with a pharmaceutical carrier.

Another advantageous combination according to this fifth embodiment may be a combination comprising or consisting essentially of, as Components:

(a) a pharmaceutical composition comprising xanomeline, as free base, as oxalate or as L-tartrate, in an amount of from 90 mg to 450 mg, normally from 90 mg to 300 mg, in admixture with a pharmaceutical carrier or vehicle;

(b) a pharmaceutical composition comprising a naAEA selected from the group consisting of alosetron hydrochloride, in an amount (in alosetron) of from 0.25 mg to 6 mg; azasetron hydrochloride, in an amount (in azasetron) of from 5 mg to 60 mg; dolasetron mesylate, in an amount (in dolasetron) of from 25 mg to 600 mg; granisetron hydrochloride, in an amount (in granisetron) of from 0.5 mg to 6 mg; ondansetron hydrochloride dihydrate, in an amount (in ondansetron) of from 2 mg to 64 mg; palonosetron hydrochloride, in an amount (in palonosetron) of from 0.25 mg to 3 mg; ramosetron hydrochloride, in an amount (in ramosetron) of from 0.0125 mg to 0.3 mg, tropisetron hydrochloride, in an amount (in tropisetron) of from 2.5 mg to 30 mg; domperidone and pharmaceutically acceptable salts and solvates thereof, in an amount (in domperidone) of from 5 mg to 60 mg; haloperidol, in an amount of from 0.5 mg to 60 mg; chlorpromazine hydrochloride, in an amount (in chlorpromazine) of from 12.5 mg to 600 mg; prochlorperazine dimaleate, in an amount (in prochlorperazine) of from 2.5 mg to 30 mg; metoclopramide monohydrochloride monohydrate, in an amount (in metoclopramide) of from 5 mg to 60 mg; bromopride monohydrochloride or dihydrochloride monohydrate, in an amount (in bromopride) of from 5 mg to 60 mg; clebopride hydrogen malate or hydrochloride monohydrate, in an amount (in clebopride) of from 0.25 mg to 3 mg; levosulpiride, in an amount of from 12.5 mg to 600 mg; alizapride hydrochloride, in an amount (in alizapride) of from 25 mg to 300 mg; trimethobenzamide monohydrochloride, in an amount (in trimethobenzamide) of from 50 mg to 600 mg; meclizine (also called meclozine) and pharmaceutically acceptable salts and solvates thereof, in an amount (in meclizine) of from 6.25 mg to 300 mg; promethazine hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant, in an amount of from 25 mg to 300 mg; in a pharmaceutical composition in admixture with a pharmaceutical carrier or vehicle; and (c) a pharmaceutical composition comprising a nsPAChA consisting of oxybutynin in admixture with a pharmaceutical carrier or vehicle, in a TTS consisting of a patch releasing from 3.9 mg/24 h to 7.8 mg/24 h oxybutynin.

Preferably, according to this fifth embodiment, the pharmaceutical composition Component (a) comprises xanomeline, as free base, as oxalate or as L-tartrate, in an amount of from 90 mg to 450 mg, normally from 90 mg to 300 mg, formulated with a pharmaceutical carrier for IR or ER administration. A particular pharmaceutical composition according to this fifth embodiment comprises xanomeline base in admixture with a pharmaceutical carrier or vehicle for ER administration, said composition being in a patch delivering a predetermined xanomeline dose over 24 hours. An advantageous predetermined xanomeline dose is released in an amount/24 h giving xanomeline plasma concentrations in human of from 16.572 ng/ml to 78.6 ng/ml. The same predetermined xanomeline dose releasing an amount/24 h giving xanomeline plasma concentrations in human of from 16.572 ng/ml to 78.6 ng/ml may also be in a xanomeline Component (a) and oxybutynin Component (c) combination in a single TTS containing the two active ingredients in admixture each other in the same TTS or separated in the same patch in two different TTSs each delivering the aforementioned xanomeline and oxybutynin daily doses.

According to a sixth embodiment, an advantageous MCRA/naAEA/nsPAChA/combination may be a combination comprising or consisting essentially of (a) milameline hydrochloride, in an amount of from 2.4 mg to 12 mg, normally from 2.4 to 10 mg, in admixture with a pharmaceutical carrier or vehicle.

(b) a pharmaceutical composition comprising a naAEA selected from the group consisting of alosetron and pharmaceutically acceptable salts and solvates thereof, azasetron and pharmaceutically acceptable salts and solvates thereof; ondansetron and pharmaceutically acceptable salts and solvates thereof; granisetron and pharmaceutically acceptable salts and solvates thereof; dolasetron and pharmaceutically acceptable salts and solvates thereof, ramosetron and pharmaceutically acceptable salts and solvates thereof; tropisetron and pharmaceutically acceptable salts and solvates thereof; and palonosetron and pharmaceutically acceptable salts and solvates thereof, domperidone and pharmaceutically acceptable salts and solvates thereof such as the maleate; chlorpromazine and pharmaceutically acceptable salts and solvates thereof such as the hydrochloride; prochlorperazine and its salts and solvates, particularly the dimaleate and the dimesylate; promethazine and pharmaceutically acceptable salts and solvates thereof such as the hydrochloride; metoclopramide and pharmaceutically acceptable salts and solvates thereof such as the hydrochloride monohydrate, bromopride and pharmaceutically acceptable salts and solvates thereof such as the monohydrochloride or the dihydrochloride monohydrate, alizapride and pharmaceutically acceptable salts and solvates thereof such as the hydrochloride, clebopride and pharmaceutically acceptable salts and solvates thereof such as the malate and the hydrochloride monohydrate, meclizine (meclozine) and pharmaceutically acceptable salts and solvates thereof, especially its hydrochloride monohydrate; hydroxyzine and pharmaceutically acceptable salts and solvates thereof such as the dihydrochloride or the 1,1'-methylene bis(2-hydroxy-3-naphthalenecarboxylic acid (pamoate) dronabinol, nabilone, aprepitant, netupitant, rolapitant, netupitant/palonosetron hydrochloride fixed-dose combination; and casopitant, in admixture with a pharmaceutical carrier or vehicle; and (c) a pharmaceutical composition comprising a nsPAChA selected from the group consisting of anisotropine pharmaceutically acceptable quaternary salts, butylscopolamine pharmaceutically acceptable salts, cimetropium pharmaceutically acceptable salts, clidinium pharmaceutically acceptable salts, fesoterodine and pharmaceutically acceptable salts thereof, glycopyrronium pharmaceutically acceptable salts, otilonium pharmaceutically acceptable salts, oxyphencyclimine and pharmaceutically acceptable salts thereof, prifinium pharmaceutically acceptable salts, propiverine and pharmaceutically acceptable salts thereof, solifenacin and pharmaceutically acceptable salts thereof, tolterodine and pharmaceutically acceptable salts thereof, timepidium pharmaceutically acceptable salts, trospium pharmaceutically acceptable salts, TTS-oxybutynin; and valethamate pharmaceutically acceptable salts; and TTS-oxybutynin, in admixture with a pharmaceutical carrier or vehicle.

Another advantageous MCRA/naAEA/nsPAChA/combination may be a combination comprising or consisting essentially of (a) milameline hydrochloride, in an amount of from 2.4 mg to 12 mg, normally from 2.4 to 10 mg, in admixture with a pharmaceutical carrier or vehicle;

(b) a pharmaceutical composition comprising a naAEA selected from the group consisting of alosetron and pharmaceutically acceptable salts and solvates thereof, in particular the hydrochloride, in an amount (in alosetron) of from 0.25 mg to 6 mg; azasetron and pharmaceutically acceptable salts and solvates thereof, in particular the hydrochloride, in an amount (in azasetron) of from 5 mg to 60 mg; dolasetron and pharmaceutically acceptable salts and solvates thereof, in particular themesylate, in an amount (in dolasetron) of from 25 mg to 600 mg; granisetron and pharmaceutically acceptable salts and solvates thereof, in particular the hydrochloride, in an amount (in granisetron) of from 0.5 mg to 6 mg; ondansetron and pharmaceutically acceptable salts and solvates thereof, in particular the hydrochloride dihydrate, in an amount (in ondansetron) of from 2 mg to 64 mg; palonosetron and pharmaceutically acceptable salts and solvates thereof, in particular the hydrochloride, in an amount (in palonosetron) of from 0.25 mg to 3 mg; ramosetron and pharmaceutically acceptable salts and solvates thereof, in particular the hydrochloride, in an amount (in ramosetron) of from 0.0125 mg to 0.3 mg, tropisetron and pharmaceutically acceptable salts and solvates thereof, in particular the hydrochloride, in an amount (in tropisetron) of from 2.5 mg to 30 mg; domperidone and pharmaceutically acceptable salts and solvates thereof, in an amount (in domperidone) of from 5 mg to 60 mg; haloperidol, in an amount of from 0.5 mg to 60 mg; chlorpromazine and pharmaceutically acceptable salts and solvates thereof, in particular the hydrochloride, in an amount (in chlorpromazine) of from 12.5 mg to 600 mg; prochlorperazine and pharmaceutically acceptable salts and solvates thereof, in particular the dimaleate, in an amount (in prochlorperazine) of from 2.5 mg to 30 mg; metoclopramide and pharmaceutically acceptable salts and solvates thereof, in particular the monohydrochloride monohydrate, in an amount (in metoclopramide) of from 5 mg to 60 mg; bromopride and pharmaceutically acceptable salts and solvates thereof, in particular the monohydrochloride or dihydrochloride monohydrate, in an amount (in bromopride) of from 5 mg to 60 mg; clebopride and pharmaceutically acceptable salts and solvates thereof, in particular the hydrogen malate or hydrochloride monohydrate, in an amount (in clebopride) of from 0.25 mg to 3 mg; levosulpiride, in an amount of from 12.5 mg to 600 mg; alizapride and pharmaceutically acceptable salts and solvates thereof, in particular the hydrochloride, in an amount (in alizapride) of from 25 mg to 300 mg; trimethobenzamide and pharmaceutically acceptable salts and solvates thereof, in particular the monohydrochloride, in an amount (in trimethobenzamide) of from 50 mg to 600 mg; meclizine (also called meclozine) and pharmaceutically acceptable salts and solvates thereof, in an amount (in meclizine) of from 6.25 mg to 300 mg; promethazine hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant, in an amount of from 25 mg to 300 mg, in admixture with a pharmaceutical carrier or vehicle; and (c) a pharmaceutical composition comprising a nsPAChA selected from the group consisting of glycopyrronium pharmaceutically acceptable salts, in an amount that is equivalent to from 0.5 mg to 16 mg of glycopyrronium bromide; propiverine and pharmaceutically acceptable salts thereof, in an amount that is equivalent to from 7.5 mg to 240 mg of propiverine hydrobromide; solifenacin and pharmaceutically acceptable salts thereof, in an amount that is equivalent to from 5 mg to 60 mg, preferably from 5 mg to 40 mg, of solifenacin succinate;

trospium pharmaceutically acceptable salts, in an amount that is equivalent to from 20 mg to 480 mg of trospium chloride; and TTS-oxybutynin, in a released amount of from 3.9 mg/24 h to 7.8 mg/24 h, in admixture with a pharmaceutical carrier or vehicle.

Another advantageous MCRA/naAEA/nsPAChA/combination according to this further aspect of this sixth embodiment may be a combination comprising or consisting essentially of (a) a pharmaceutical composition comprising milameline hydrochloride, in an amount of from 2.4 mg to 12 mg, normally from 2.4 to 10 mg, in admixture with a pharmaceutical carrier or vehicle;

(b) a pharmaceutical composition comprising a naAEA selected from the group consisting of alosetron and pharmaceutically acceptable salts and solvates thereof, in particular the hydrochloride, in an amount (in alosetron) of from 0.25 mg to 6 mg; azasetron and pharmaceutically acceptable salts and solvates thereof, in particular the hydrochloride, in an amount (in azasetron) of from 5 mg to 60 mg; dolasetron and pharmaceutically acceptable salts and solvates thereof, in particular the mesylate, in an amount (in dolasetron) of from 25 mg to 600 mg; granisetron and pharmaceutically acceptable salts and solvates thereof, in particular the hydrochloride, in an amount (in granisetron) of from 0.5 mg to 6 mg; ondansetron and pharmaceutically acceptable salts and solvates thereof, in particular the hydrochloride dihydrate, in an amount (in ondansetron) of from 2 mg to 64 mg; palonosetron and pharmaceutically acceptable salts and solvates thereof, in particular the hydrochloride, in an amount (in palonosetron) of from 0.25 mg to 3 mg; ramosetron and pharmaceutically acceptable salts and solvates thereof, in particular the hydrochloride, in an amount (in ramosetron) of from 0.0125 mg to 0.3 mg, tropisetron and pharmaceutically acceptable salts and solvates thereof, in particular the hydrochloride, in an amount (in tropisetron) of from 2.5 mg to 30 mg; domperidone and pharmaceutically acceptable salts and solvates thereof, in an amount (in domperidone) of from 5 mg to 60 mg; haloperidol, in an amount of from 0.5 mg to 60 mg; chlorpromazine and pharmaceutically acceptable salts and solvates thereof, in particular the hydrochloride, in an amount (in chlorpromazine) of from 12.5 mg to 600 mg; prochlorperazine and pharmaceutically acceptable salts and solvates thereof, in particular the dimaleate, in an amount (in prochlorperazine) of from 2.5 mg to 30 mg; metoclopramide and pharmaceutically acceptable salts and solvates thereof, in particular the monohydrochloride monohydrate, in an amount (in metoclopramide) of from 5 mg to 60 mg; bromopride and pharmaceutically acceptable salts and solvates thereof, in particular the monohydrochloride or dihydrochloride monohydrate, in an amount (in bromopride) of from 5 mg to 60 mg; clebopride and pharmaceutically acceptable salts and solvates thereof, in particular the hydrogen malate or hydrochloride monohydrate, in an amount (in clebopride) of from 0.25 mg to 3 mg; levosulpiride, in an amount of from 12.5 mg to 600 mg; alizapride and pharmaceutically acceptable salts and solvates thereof, in particular the hydrochloride, in an amount (in alizapride) of from 25 mg to 300 mg; trimethobenzamide and pharmaceutically acceptable salts and solvates thereof, in particular the monohydrochloride, in an amount (in trimethobenzamide) of from 50 mg to 600 mg; meclizine (also called meclozine) and pharmaceutically acceptable salts and solvates thereof, in an amount (in meclizine) of from 6.25 mg to 300 mg; promethazine hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant, in an amount of from 25 mg to 300 mg, in admixture with a pharmaceutical carrier or vehicle; and (c) a pharmaceutical composition comprising a nsPAChA selected from the group consisting of anisotropine methylbromide, in an amount of from 60 mg to 300 mg, normally from 60 mg to 200 mg; butylscopolamine bromide in an amount of from 12 mg to 60 mg, normally from 12 mg to 40; cimetropium bromide, in an amount of from 55 mg to 200 mg; clidinium bromide in an amount of from 3 mg to 15 mg, normally from 3 mg to 10 mg; fesoterodine fumarate, in an amount of from 9.6 mg to 32 mg; glycopyrronium bromide in an amount of from 2.2 to 12 mg, normally from 2.2 to 8 mg; otilonium bromide in an amount of from 48 mg to 240 mg, normally from 48 mg to 160 mg; prifinium bromide in an amount of from 36 mg to 180 mg, normally from 36 mg to 120 mg; propiverine hydrochloride, in an amount of from 18 mg to 180 mg; solifenacin succinate, in an amount selected from the group consisting of from 5 mg to 60 mg, from 5 mg to 40 mg, from 10 mg to 40 mg, from 12 mg to 30 mg, from 12 mg to 25 mg, and 21 mg; tolterodine tartrate, in an amount of from 4.8 mg to 16 mg; timepidium bromide in an amount of from 36 mg to 180 mg, normally from 36 mg to 120 mgr; trospium chloride, in an amount of from 24 mg to 240 mg; TTS-oxybutynin releasing from 3.9 mg/24 to 7.8 mg/24 h oxybutynin; and valethamate bromide in an amount of from 12 mg to 60 mg;

in admixture with a pharmaceutical carrier or vehicle.

Another advantageous MCRA/naAEA/nsPAChA/combination may be a combination comprising or consisting essentially of (a) a pharmaceutical composition comprising milameline hydrochloride, in an amount of from 2.4 mg to 12 mg, normally from 2.4 to 10 mg, in admixture with a pharmaceutical carrier or vehicle;

(b) a pharmaceutical composition comprising a naAEA selected from the group consisting of alosetron hydrochloride, in an amount (in alosetron) of from 0.25 mg to 6 mg; azasetron hydrochloride, in an amount (in azasetron) of from 5 mg to 60 mg; dolasetron mesylate, in an amount (in dolasetron) of from 25 mg to 600 mg; granisetron hydrochloride, in an amount (in granisetron) of from 0.5 mg to 6 mg; ondansetron hydrochloride dihydrate, in an amount (in ondansetron) of from 2 mg to 64 mg; palonosetron hydrochloride, in an amount (in palonosetron) of from 0.25 mg to 3 mg; ramosetron hydrochloride, in an amount (in ramosetron) of from 0.0125 mg to 0.3 mg, tropisetron hydrochloride, in an amount (in tropisetron) of from 2.5 mg to 30 mg; domperidone and pharmaceutically acceptable salts and solvates thereof, in an amount (in domperidone) of from 5 mg to 60 mg; haloperidol, in an amount of from 0.5 mg to 60 mg; chlorpromazine hydrochloride, in an amount (in chlorpromazine) of from 12.5 mg to 600 mg; prochlorperazinedimaleate, in an amount (in prochlorperazine) of from 2.5 mg to 30 mg; metoclopramide monohydrochloride monohydrate, in an amount (in metoclopramide) of from 5 mg to 60 mg; bromopride monohydrochloride or dihydrochloride monohydrate, in an amount (in bromopride) of from 5 mg to 60 mg; clebopride hydrogen malate or hydrochloride monohydrate, in an amount (in clebopride) of from 0.25 mg to 3 mg; levosulpiride, in an amount of from 12.5 mg to 600 mg; alizapride hydrochloride, in an amount (in alizapride) of from 25 mg to 300 mg; trimethobenzamide monohydrochloride, in an amount (in trimethobenzamide) of from 50 mg to 600 mg; meclizine (also called meclozine) and pharmaceutically acceptable salts and solvates thereof, in an amount (in meclizine) of from 6.25 mg to 300 mg; promethazine hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant, in an amount of from 25 mg to 300 mg; in a pharmaceutical composition in admixture with a pharmaceutical carrier or vehicle; and (c) a pharmaceutical composition comprising a nsPAChA selected from the group consisting of oxybutynin in admixture with a pharmaceutical carrier in a TTS consisting of a patch releasing from 3.9 mg/24 h to 7.8 mg/24 h oxybutynin.

Preferably, according to this sixth embodiment, the pharmaceutical composition Component (a) comprises a pharmaceutical composition comprising milameline. as free base or as hydrochloride, in an amount of from 2.4 mg to 12 mg, normally from 2.4 to 10 mg, formulated with a pharmaceutical carrier for IR or ER administration.

According to a seventh embodiment, an advantageous MCRA/naAEA/nsPAChA combination according to the present invention is a combination comprising or consisting essentially of (a) MK-7622, as free base, as hydrochloride, as monomethanesulfonate or as fumarate, in an amount consisting of from 5 mg to 270 mg, in particular of from more than 5 mg to 15 mg, from more than 15 mg to 45 mg, from more than 45 mg to 270 mg, from more than 15 mg to 225 mg, from more than 45 mg to 225 mg, and from 54 mg to 180 mg, in an IR-formulated oral composition in admixture with a pharmaceutical carrier or vehicle;

(b) a pharmaceutical composition comprising a naAEA selected from the group consisting of alosetron and pharmaceutically acceptable salts and solvates thereof, especially its hydrochloride; azasetron and pharmaceutically acceptable salts and solvates thereof, especially its hydrochloride; ondansetron and pharmaceutically acceptable salts and solvates thereof, especially its monohydrochloride dihydrate; granisetron and pharmaceutically acceptable salts and solvates thereof, especially its hydrochloride; dolasetron and pharmaceutically acceptable salts and solvates thereof, especially its monomethanesulfonate monohydrate; ramosetron and pharmaceutically acceptable salts and solvates thereof; tropisetron and pharmaceutically acceptable salts and solvates thereof, especially its hydrochloride; and palonosetron and pharmaceutically acceptable salts and solvates thereof, especially its hydrochloride; domperidone and pharmaceutically acceptable salts and solvates thereof such as the maleate; chlorpromazine and pharmaceutically acceptable salts and solvates thereof such as the hydrochloride; prochlorperazine and its salts and solvates, particularly the dimaleate and the dimesylate; promethazine and pharmaceutically acceptable salts and solvates thereof such as the hydrochloride; metoclopramide and pharmaceutically acceptable salts and solvates thereof such as the hydrochloride monohydrate bromopride and pharmaceutically acceptable salts and solvates thereof such as the monohydrochloride or the dihydrochloride monohydrate, alizapride and pharmaceutically acceptable salts and solvates thereof such as the hydrochloride; clebopride and pharmaceutically acceptable salts and solvates thereof such as the malate and the hydrochloride monohydrate; meclizine (meclozine) and pharmaceutically acceptable salts and solvates thereof, especially its hydrochloride monohydrate; dronabinol; nabilone; aprepitant; netupitant; rolapitant; netupitant/palonosetron hydrochloride fixed-dose combination; and casopitant, in admixture with a pharmaceutical carrier or vehicle; and (c) a pharmaceutical composition comprising a nsPAChA selected from the group consisting of anisotropine pharmaceutically acceptable quaternary salts, butylscopolamine pharmaceutically acceptable salts, cimetropium pharmaceutically acceptable salts, clidinium pharmaceutically acceptable salts, fesoterodine and pharmaceutically acceptable salts thereof, glycopyrronium pharmaceutically acceptable salts, otilonium pharmaceutically acceptable salts, oxyphencyclimine and pharmaceutically acceptable salts thereof, prifinium pharmaceutically acceptable salts, propiverine and pharmaceutically acceptable salts thereof, solifenacin and pharmaceutically acceptable salts thereof, tolterodine and pharmaceutically acceptable salts thereof, timepidium pharmaceutically acceptable salts, trospium pharmaceutically acceptable salts, TTS-oxybutynin; and valethamate pharmaceutically acceptable salts; and TTS-oxybutynin, in admixture with a pharmaceutical carrier or vehicle.

Another advantageous MCRA/naAEA/nsPAChA/combination according to this may be a combination comprising or consisting essentially of (a) MK-7622, as free base, as hydrochloride, as monomethanesulfonate or as fumarate, in an amount consisting of from 5 mg to 270 mg, in particular of from more than 5 mg to 15 mg, from more than 15 mg to 45 mg, from more than 45 mg to 270 mg, from more than 15 mg to 225 mg, from more than 45 mg to 225 mg, and from 54 mg to 180 mg, in an IR-formulated oral composition in admixture with a pharmaceutical carrier or vehicle;

(b) a pharmaceutical composition comprising a naAEA selected from the group consisting of alosetron and pharmaceutically acceptable salts and solvates thereof, especially its hydrochloride; azasetron and pharmaceutically acceptable salts and solvates thereof, especially its hydrochloride; ondansetron and pharmaceutically acceptable salts and solvates thereof, especially its monohydrochloride dihydrate; granisetron and pharmaceutically acceptable salts and solvates thereof, especially its hydrochloride; dolasetron and pharmaceutically acceptable salts and solvates thereof, especially its monomethanesulfonate monohydrate; ramosetron and pharmaceutically acceptable salts and solvates thereof; tropisetron and pharmaceutically acceptable salts and solvates thereof, especially its hydrochloride; and palonosetron and pharmaceutically acceptable salts and solvates thereof, especially its hydrochloride; domperidone and pharmaceutically acceptable salts and solvates thereof such as the maleate; chlorpromazine and pharmaceutically acceptable salts and solvates thereof such as the hydrochloride; prochlorperazine and its salts and solvates, particularly the dimaleate and the dimesylate; promethazine and pharmaceutically acceptable salts and solvates thereof such as the hydrochloride; metoclopramide and pharmaceutically acceptable salts and solvates thereof such as the hydrochloride monohydrate, bromopride and pharmaceutically acceptable salts and solvates thereof such as the monohydrochloride or the dihydrochloride monohydrate, alizapride and pharmaceutically acceptable salts and solvates thereof such as the hydrochloride; clebopride and pharmaceutically acceptable salts and solvates thereof such as the malate and the hydrochloride monohydrate; meclizine (meclozine) and pharmaceutically acceptable salts and solvates thereof, especially its hydrochloride monohydrate; dronabinol; nabilone; aprepitant; netupitant; rolapitant; netupitant/palonosetron hydrochloride fixed-dose combination; and casopitant, in admixture with a pharmaceutical carrier or vehicle; and (c) a pharmaceutical composition comprising a nsPAChA being preferably selected from the group consisting of anisotropine methylbromide, butylscopolamine bromide, cimetropium bromide, clidinium bromide, fesoterodine fumarate, glycopyrronium bromide, otilonium bromide, oxyphencyclimine hydrochloride, prifinium bromide, propiverine hydrochloride, solifenacin succinate, tolterodine tartrate, timepidium bromide, trospium chloride, TTS-oxybutynin and valethamate bromide; in admixture with a pharmaceutical carrier.

According to a further aspect of this seventh embodiment, an advantageous MCRA/naAEA/nsPAChA/combination may be a combination comprising or consisting essentially of (a) a pharmaceutical composition comprising MK-7622, as free base, as hydrochloride, as monomethanesulfonate or as fumarate, in an amount of from 5 mg to 270 mg, in particular in an amount range selected from the group consisting of from more than 5 mg to 15 mg, from more than 15 mg to 45 mg, from more than 45 mg to 270 mg, from more than 15 mg to 225 mg, from more than 45 mg to 225 mg, and from 54 mg to 180 mg, in admixture with a pharmaceutical carrier or vehicle;

(b) a pharmaceutical composition comprising a naAEA selected from the group consisting of alosetron and pharmaceutically acceptable salts and solvates thereof, in particular the hydrochloride, in an amount (in alosetron) of from 0.25 mg to 6 mg; azasetron and pharmaceutically acceptable salts and solvates thereof, in particular the hydrochloride, in an amount (in azasetron) of from 5 mg to 60 mg; dolasetron and pharmaceutically acceptable salts and solvates thereof, in particular the mesylate, in an amount (in dolasetron) of from 25 mg to 600 mg; granisetron and pharmaceutically acceptable salts and solvates thereof, in particular the hydrochloride, in an amount (in granisetron) of from 0.5 mg to 6 mg; ondansetron and pharmaceutically acceptable salts and solvates thereof, in particular the hydrochloride dihydrate, in an amount (in ondansetron) of from 2 mg to 64 mg; palonosetron and pharmaceutically acceptable salts and solvates thereof, in particular the hydrochloride, in an amount (in palonosetron) of from 0.25 mg to 3 mg; ramosetron and pharmaceutically acceptable salts and solvates thereof, in particular the hydrochloride, in an amount (in ramosetron) of from 0.0125 mg to 0.3 mg, tropisetron and pharmaceutically acceptable salts and solvates thereof, in particular the hydrochloride, in an amount (in tropisetron) of from 2.5 mg to 30 mg; domperidone and pharmaceutically acceptable salts and solvates thereof, in an amount (in domperidone) of from 5 mg to 60 mg; haloperidol, in an amount of from 0.5 mg to 60 mg; chlorpromazine and pharmaceutically acceptable salts and solvates thereof, in particular the hydrochloride, in an amount (in chlorpromazine) of from 12.5 mg to 600 mg; prochlorperazine and pharmaceutically acceptable salts and solvates thereof, in particular the dimaleate, in an amount (in prochlorperazine) of from 2.5 mg to 30 mg; metoclopramide and pharmaceutically acceptable salts and solvates thereof, in particular the monohydrochloride monohydrate, in an amount (in metoclopramide) of from 5 mg to 60 mg; bromopride and pharmaceutically acceptable salts and solvates thereof, in particular the monohydrochloride or dihydrochloride monohydrate, in an amount (in bromopride) of from 5 mg to 60 mg; clebopride and pharmaceutically acceptable salts and solvates thereof, in particular the hydrogen malate or hydrochloride monohydrate, in an amount (in clebopride) of from 0.25 mg to 3 mg; levosulpiride, in an amount of from 12.5 mg to 600 mg; alizapride and pharmaceutically acceptable salts and solvates thereof, in particular the hydrochloride, in an amount (in alizapride) of from 25 mg to 300 mg; trimethobenzamide and pharmaceutically acceptable salts and solvates thereof, in particular the monohydrochloride, in an amount (in trimethobenzamide) of from 50 mg to 600 mg; meclizine (also called meclozine) and pharmaceutically acceptable salts and solvates thereof, in an amount (in meclizine) of from 6.25 mg to 300 mg; promethazine and pharmaceutically acceptable salts and solvates thereof, in particular the hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant, in an amount of from 25 mg to 300 mg; in a pharmaceutical composition in admixture with a pharmaceutical carrier or vehicle; and (c) a pharmaceutical composition comprising a nsPAChA selected from the group consisting of glycopyrronium pharmaceutically acceptable salts, in an amount that is equivalent to from 0.5 mg to 16 mg of glycopyrronium bromide; propiverine and pharmaceutically acceptable salts thereof, in an amount that is equivalent to from 7.5 mg to 240 mg of propiverine hydrobromide; solifenacin and pharmaceutically acceptable salts thereof, in an amount that is equivalent to from 5 mg to 60 mg, preferably from 5 mg to 40 mg, of solifenacin succinate; trospium pharmaceutically acceptable salts, in an amount that is equivalent to from 20 mg to 480 mg of trospium chloride; and TTS-oxybutynin, in a released amount of from 3.9 mg/24 h to 7.8 mg/24 h, in admixture with a pharmaceutical carrier or vehicle.

Another advantageous MCRA/naAEA/nsPAChA/combination according to this aspect of this seventh embodiment may be a combination comprising or consisting essentially of (a) a pharmaceutical composition comprising MK-7622, as free base, as hydrochloride, as monomethanesulfonate or as fumarate, in an amount of from 5 mg to 270 mg, in particular in an amount range selected from the group consisting of from more than 5 mg to 15 mg, from more than 15 mg to 45 mg, from more than 45 mg to 270 mg, from more than 15 mg to 225 mg, from more than 45 mg to 225 mg, and from 54 mg to 180 mg, in admixture with a pharmaceutical carrier;

(b) a pharmaceutical composition comprising a naAEA selected from the group consisting of alosetron and pharmaceutically acceptable salts and solvates thereof, in particular the hydrochloride, in an amount (in alosetron) of from 0.25 mg to 6 mg; azasetron and pharmaceutically acceptable salts and solvates thereof, in particular the hydrochloride, in an amount (in azasetron) of from 5 mg to 60 mg; dolasetron and pharmaceutically acceptable salts and solvates thereof, in particular the mesylate, in an amount (in dolasetron) of from 25 mg to 600 mg; granisetron and pharmaceutically acceptable salts and solvates thereof, in particular the hydrochloride, in an amount (in granisetron) of from 0.5 mg to 6 mg; ondansetron and pharmaceutically acceptable salts and solvates thereof, in particular the hydrochloride dihydrate, in an amount (in ondansetron) of from 2 mg to 64 mg; palonosetron and pharmaceutically acceptable salts and solvates thereof, in particular the hydrochloride, in an amount (in palonosetron) of from 0.25 mg to 3 mg; ramosetron and pharmaceutically acceptable salts and solvates thereof, in particular the hydrochloride, in an amount (in ramosetron) of from 0.0125 mg to 0.3 mg, tropisetron and pharmaceutically acceptable salts and solvates thereof, in particular the hydrochloride, in an amount (in tropisetron) of from 2.5 mg to 30 mg; domperidone and pharmaceutically acceptable salts and solvates thereof, in an amount (in domperidone) of from 5 mg to 60 mg; haloperidol, in an amount of from 0.5 mg to 60 mg; chlorpromazine and pharmaceutically acceptable salts and solvates thereof, in particular the hydrochloride, in an amount (in chlorpromazine) of from 12.5 mg to 600 mg; prochlorperazine and pharmaceutically acceptable salts and solvates thereof, in particular the dimaleate, in an amount (in prochlorperazine) of from 2.5 mg to 30 mg; metoclopramide and pharmaceutically acceptable salts and solvates thereof, in particular the monohydrochloride monohydrate, in an amount (in metoclopramide) of from 5 mg to 60 mg; bromopride and pharmaceutically acceptable salts and solvates thereof, in particular the monohydrochloride or dihydrochloride monohydrate, in an amount (in bromopride) of from 5 mg to 60 mg; clebopride and pharmaceutically acceptable salts and solvates thereof, in particular the hydrogen malate or hydrochloride monohydrate, in an amount (in clebopride) of from 0.25 mg to 3 mg; levosulpiride, in an amount of from 12.5 mg to 600 mg; alizapride and pharmaceutically acceptable salts and solvates thereof, in particular the hydrochloride, in an amount (in alizapride) of from 25 mg to 300 mg; trimethobenzamide and pharmaceutically acceptable salts and solvates thereof, in particular the monohydrochloride, in an amount (in trimethobenzamide) of from 50 mg to 600 mg; meclizine (also called meclozine) and pharmaceutically acceptable salts and solvates thereof, in an amount (in meclizine) of from 6.25 mg to 300 mg; promethazine and pharmaceutically acceptable salts and solvates thereof, in particular the hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant, in an amount of from 25 mg to 300 mg; in a pharmaceutical composition in admixture with a pharmaceutical carrier or vehicle; and (c) a pharmaceutical composition comprising a nsPAChA selected from the group consisting of anisotropine methylbromide, in an amount of from 60 mg to 300 mg, normally from 60 mg to 200 mg; butylscopolamine bromide in an amount of from 12 mg to 60 mg, normally from 12 mg to 40; cimetropium bromide, in an amount of from 55 mg to 200 mg; clidinium bromide in an amount of from 3 mg to 15 mg, normally from 3 mg to 10 mg; fesoterodine fumarate, in an amount of from 9.6 mg to 32 mg; glycopyrronium bromide in an amount of from 2.2 to 12 mg, normally from 2.2 to 8 mg; otilonium bromide in an amount of from 48 mg to 240 mg, normally from 48 mg to 160 mg; prifinium bromide in an amount of from 36 mg to 180 mg, normally from 36 mg to 120 mg; propiverine hydrochloride, in an amount of from 18 mg to 180 mg; solifenacin succinate, in an amount selected from the group consisting of from 5 mg to 60 mg, from 10 mg to 40 mg, from 12 mg to 30 mg, from 12 mg to 25 mg, and 21 mg; tolterodine tartrate, in an amount of from 4.8 mg to 16 mg; timepidium bromide in an amount of from 7.5 mg to 180 mg, normally from 36 mg to 120 mg; trospium chloride, in an amount of from 24 mg to 240 mg; TTS-oxybutynin releasing from 3.9 mg/24 to 7.8 mg/24 h oxybutynin; and valethamate bromide in an amount of from 12 mg to 60 mg;

in admixture with a pharmaceutical carrier or vehicle.

Another advantageous MCRA/naAEA/nsPAChA/combination may be a combination comprising or consisting essentially of (a) a pharmaceutical composition comprising MK-7622, as free base, as hydrochloride or as fumarate, in an amount of from 5 mg to 270 mg, in particular in an amount selected from the group consisting of from more than 5 mg to 15 mg, from more than 15 mg to 45 mg, from more than 45 mg to 270 mg, from more than 15 mg to 225 mg, from more than 45 mg to 225 mg, and from 54 mg to 180 mg, in admixture with a pharmaceutical carrier or vehicle;

(b) a pharmaceutical composition comprising a naAEA selected from the group consisting of alosetron hydrochloride, in an amount (in alosetron) of from 0.25 mg to 6 mg; azasetron hydrochloride, in an amount (in azasetron) of from 5 mg to 60 mg; dolasetron mesylate, in an amount (in dolasetron) of from 25 mg to 600 mg; granisetron hydrochloride, in an amount (in granisetron) of from 0.5 mg to 6 mg; ondansetron hydrochloride dihydrate, in an amount (in ondansetron) of from 2 mg to 64 mg; palonosetron hydrochloride, in an amount (in palonosetron) of from 0.25 mg to 3 mg; ramosetron hydrochloride, in an amount (in ramosetron) of from 0.0125 mg to 0.3 mg, tropisetron hydrochloride, in an amount (in tropisetron) of from 2.5 mg to 30 mg; domperidone and pharmaceutically acceptable salts and solvates thereof, in an amount (in domperidone) of from 5 mg to 60 mg; haloperidol, in an amount of from 0.5 mg to 60 mg; chlorpromazine hydrochloride, in an amount (in chlorpromazine) of from 12.5 mg to 600 mg; prochlorperazinedimaleate, in an amount (in prochlorperazine) of from 2.5 mg to 30 mg; metoclopramide monohydrochloride monohydrate, in an amount (in metoclopramide) of from 5 mg to 60 mg; bromopride monohydrochloride or dihydrochloride monohydrate, in an amount (in bromopride) of from 5 mg to 60 mg; clebopride hydrogen malate or hydrochloride monohydrate, in an amount (in clebopride) of from 0.25 mg to 3 mg; levosulpiride, in an amount of from 12.5 mg to 600 mg; alizapride hydrochloride, in an amount (in alizapride) of from 25 mg to 300 mg; trimethobenzamide monohydrochloride, in an amount (in trimethobenzamide) of from 50 mg to 600 mg; meclizine (also called meclozine) and pharmaceutically acceptable salts and solvates thereof, in an amount (in meclizine) of from 6.25 mg to 300 mg; promethazine hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant, in an amount of from 25 mg to 300 mg; in a pharmaceutical composition in admixture with a pharmaceutical carrier or vehicle; and (c) a pharmaceutical composition comprising a nsPAChA selected from the group consisting of oxybutynin in admixture with a pharmaceutical carrier or vehicle in a TTS consisting of a patch releasing from 3.9 mg/24 h to 7.8 mg/24 h, normally 3.9 mg/24 h, oxybutynin.

Advantageously, according to this seventh embodiment, the pharmaceutical composition comprises the MK-7622 Component (a) in an amount of from 5 mg to 270 mg, in particular in an amount range selected from the group consisting of from more than 5 mg to 15 mg, from more than 15 mg to 45 mg, from more than 45 mg to 270 mg, from more than 15 mg to 225 mg, from more than 45 mg to 225 mg, and from 54 mg to 180 mg, in admixture with a pharmaceutical carrier or vehicle in an oral IR or ER formulation. Preferably, Component (a) comprises MK-7622, as free base, as hydrochloride or as fumarate, in an amount from 6 mg to 270 mg, normally from more than 45 mg to 180 mg, in admixture with a pharmaceutical carrier or vehicle in an oral IR or ER formulation.

According to an eighth embodiment, an advantageous MCRA/naAEA/nsPAChA combination may be a combination comprising or consisting essentially of (a) a MCRA, in a pharmaceutical composition in admixture with a pharmaceutical carrier or vehicle; and (b/c) a fixed-dose combination comprising (b) a naAEA; and (c) a nsPAChA, in admixture with a pharmaceutical carrier or vehicle.

In the fixed dose combination (b/c), the naAEA and the nsPAChA may be any one of the above "The naAEA Component (b)" and "The nsPAChA Component (c)" sections. Advantageous Component (b/c) may be fixed-dose combination consisting of any one of the pharmaceutical compositions described in WO 2014/039627.

Component (a) may be any one of the above illustrated MCRAs, in particular cevimeline hydrochloride hemihydrate, in an amount of from 34.5 mg to 180 mg, xanomeline, as free base, as oxalate or as L-tartrate, in an amount of from 90 mg to 450 mg, milameline hydrochloride, in an amount of from 2.4 mg to 12 mg and MK 7622, as free base, as hydrochloride, as fumarate or as methanesulfonate, in an amount consisting of from more than 5 mg to 15 mg, from more than 15 mg to 45 mg, from more than 45 mg to 270 mg, from more than 15 mg to 225 mg, from more than 45 mg to 225 mg, and from 54 mg to 180 mg, in a pharmaceutical composition in admixture with a pharmaceutical carrier or vehicle.

A particular advantageous MCRA/naAEA/nsPAChA/ combination according to this embodiment may be a combination comprising or consisting essentially of (a) a MCRA, in a pharmaceutical composition in admixture with a pharmaceutical carrier or vehicle; and (b/c) a fixed-dose combination comprising (b) a naAEA; and (c) a nsPAChA selected from the group consisting of propiverine and pharmaceutically acceptable salts thereof, in an amount corresponding to from 15 mg to 240 mg of propiverine hydrochloride, trospium pharmaceutically acceptable salts, in an amount corresponding to from 20 mg to 480 mg of trospium chloride; and glycopyrronium pharmaceutically acceptable salts corresponding to from 2 mg to 16 mg og glycopyrronium bromide, in admixture with a pharmaceutical carrier or vehicle.

In said particularly advantageous combination, said MCRA Component (a) is preferably selected from the group consisting of cevimeline and pharmaceutically acceptable salts and solvates thereof, in an amount, in cevimeline, of from 34.5 mg to 180 mg, xanomeline, and pharmaceutically acceptable salts and solvates thereof, in an amount, in xanomeline, of from 90 mg to 450 mg, milameline and pharmaceutically acceptable salts and solvates thereof, in an amount, in milameline of from 2.4 mg to 12 mg; and MK-2276 and pharmaceutically acceptable salts and solvates thereof, in an amount, in MK-7622, of from 6 mg to 270 mg, Another advantageous MCRA/naAEA/nsPAChA combination according to this embodiment is a combination comprising or consisting essentially of (a) a MCRA, in a pharmaceutical composition in admixture with a pharmaceutical carrier; and (b/c) a fixed-dose combination comprising (b) a naAEA; and (c) a nsPAChA selected from the group consisting of solifenacin and pharmaceutically acceptable salts thereof, in an amount corresponding to from 5 mg to 60 mg; from 5 mg to 40 mg, from 12 mg to 30 mg, from 12 mg to 25 mg; and 21 mg of solifenacin succinate, in admixture with a pharmaceutical carrier or vehicle.

In said particularly advantageous combination, said MCRA Component (a) is preferably selected from the group consisting of cevimeline and pharmaceutically acceptable salts and solvates thereof, in an amount (in cevimeline, of from 34.5 mg to 180 mg, xanomeline, and pharmaceutically acceptable salts and solvates thereof, in an amount, in xanomeline, of from 90 mg to 450 mg, milameline and pharmaceutically acceptable salts and solvates thereof, in an amount, in milameline of from 2.4 mg to 12 mg; and MK-2276 and pharmaceutically acceptable salts and solvates thereof, in an amount, in MK-7622, of from 6 mg to 270 mg, According to a ninth embodiment, an advantageous MCRA/naAEA/nsPAChA combination may be a combination comprising or consisting essentially of a nsPAChA Component (c), in a pharmaceutical composition in admixture with a pharmaceutical carrier or vehicle; and a fixed-dose combination essentially consisting of a pharmaceutical composition in dosage unit form comprising a MCRA Component (a); and a naAEA Component (b), in admixture with a pharmaceutical carrier or vehicle.

In the fixed-dose combination, the MCRA Component (a) and the naAEA Component (b) may be any one of the corresponding compounds illustrated in the above "The MCRA Component (a)" and "The naAEA Component (b)".

An advantageous MCRA/naAEA composition in dosage unit form comprises or essentially consists of (i) a MCRA selected from the group consisting of AF267 and pharmaceutically acceptable salts and solvates thereof; cevimeline and pharmaceutically acceptable salts and solvates thereof; 3-[3-(3-(3-fluorophenyl)-2-propyn-1-ylthio)-1,2,5-thiadiazol-4-yl]-1,2,5,6-tetrahydro-1-methylpyridine and pharmaceutically acceptable salts and solvates thereof; milameline and pharmaceutically acceptable salts and solvates thereof; RS-86 and pharmaceutically acceptable salts and solvates thereof; sabcomeline and pharmaceutically acceptable salts and solvates thereof; talsaclidine and pharmaceutically acceptable salts and solvates thereof; 5-[4-(hexylsulfanyl)-1,2,5-thiadiazol-3-yl]-1-methyl-1,2,3,6-tetrahydropyridine and pharmaceutically acceptable salts and solvates thereof; xanomeline and pharmaceutically acceptable salts and solvates thereof; MCD-386 and pharmaceutically acceptable salts and solvates thereof; 3-Methyl-5-(piperidin-3-yl)-1,2,4-oxadiazole, its enantiomers and pharmaceutically acceptable salts and solvates thereof; MK-7622 and pharmaceutically acceptable salts and solvates thereof; and (ii) a naAEA selected from the group consisting of (b1) 5HT3-antagonists, (b2) DA-antagonists, (b3) H1-antagonists, (b4) cannabinoids, (b5) NK1-antagonists, in admixture with a pharmaceutical carrier or vehicle.

A particularly advantageous MCRA/naAEA composition in dosage unit form comprises or essentially consists of (i) a MCRA selected from the group consisting of cevimeline hydrochloride hemihydrate, in an amount of from 34.5 mg to 180 mg, xanomeline, as free base, as oxalate or as L-tartrate, in an amount of from 90 mg to 450 mg, milameline hydrochloride, in an amount of from 2.4 mg to 12 mg and MK 7622, as free base, as hydrochloride, as fumarate or as methanesulfonate, in an amount selected from the group consisting of from more than 5 mg to 15 mg, from more than 15 mg to 45 mg, from more than 45 mg to 270 mg, from more than 15 mg to 225 mg, from more than 45 mg to 225 mg, and from 54 mg to 180 mg; and (ii) a naAEA selected from the group consisting of alosetron hydrochloride, in an amount (in alosetron) of from 0.25 mg to 6 mg; azasetron hydrochloride, in an amount (in azasetron) of from 5 mg to 60 mg; dolasetron mesylate, in an amount (in dolasetron) of from 25 mg to 600 mg; granisetron hydrochloride, in an amount (in granisetron) of from 0.5 mg to 6 mg; ondansetron hydrochloride dihydrate, in an amount (in ondansetron) of from 2 mg to 64 mg; palonosetron hydrochloride, in an amount (in palonosetron) of from 0.25 mg to 3 mg; ramosetron hydrochloride, in an amount (in ramosetron) of from 0.0125 mg to 0.3 mg, tropisetron hydrochloride, in an amount (in tropisetron) of from 2.5 mg to 30 mg; domperidone and pharmaceutically acceptable salts and solvates thereof, in an amount (in domperidone) of from 5 mg to 60 mg; haloperidol, in an amount of from 0.5 mg to 60 mg; chlorpromazine hydrochloride, in an amount (in chlorpromazine) of from 12.5 mg to 600 mg; prochlorperazine dimaleate, in an amount (in prochlorperazine) of from 2.5 mg to 30 mg; metoclopramide monohydrochloride monohydrate, in an amount (in metoclopramide) of from 5 mg to 60 mg; bromopride monohydrochloride or dihydrochloride monohydrate, in an amount (in bromopride) of from 5 mg to 60 mg; clebopride hydrogen malate or hydrochloride monohydrate, in an amount (in clebopride) of from 0.25 mg to 3 mg; levosulpiride, in an amount of from 12.5 mg to 600 mg; alizapride hydrochloride, in an amount (in alizapride) of from 25 mg to 300 mg; trimethobenzamide monohydrochloride, in an amount (in trimethobenzamide) of from 50 mg to 600 mg; meclizine (also called meclozine) and pharmaceutically acceptable salts and solvates thereof, in an amount (in meclizine) of from 6.25 mg to 300 mg; promethazine hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant, in an amount of from 25 mg to 300 mg, in admixture with a pharmaceutical carrier or vehicle.

A particularly advantageous MCRA/naAEA fixed-dose combination according to this aspect of this ninth embodiment consists of a transdermal patch comprising xanomeline and granisetron.

The nsPAChA Component (c) may be any one of the corresponding compounds illustrated in "The nsPAChA Component (c)" section, formulated in a pharmaceutical composition in a unit form or device, in admixture with a pharmaceutical carrier or vehicle.

A preferred composition in a unit form or device comprises a nsPAChA Component (c) selected from the group consisting of glycopyrronium pharmaceutically acceptable salts, in an amount that is equivalent to from 0.5 mg to 16 mg of glycopyrronium bromide; propiverine and pharmaceutically acceptable salts thereof, in an amount that is equivalent to from 7.5 mg to 240 mg of propiverine hydrobromide; solifenacin and pharmaceutically acceptable salts thereof, in an amount that is equivalent to from 5 mg to 60 mg, preferably from 5 mg to 40 mg, of solifenacin succinate; trospium pharmaceutically acceptable salts, in an amount that is equivalent to from 20 mg to 480 mg of trospium chloride; and TTS-oxybutynin, in a released amount of from 3.9 mg/24 h to 7.8 mg/24 h, in admixture with a pharmaceutical carrier or vehicle.

A specific composition in a unit form or device comprises a nsPAChA Component (c) selected from the group consisting of anisotropine methylbromide, in an amount of from 60 mg to 300 mg, normally from 60 mg to 200 mg; butylscopolamine bromide in an amount of from 12 mg to 60 mg, normally from 12 mg to 40; cimetropium bromide; in an amount of from 55 mg to 200 mg; clidinium bromide in an amount of from 3 mg to 15 mg, normally from 3 mg to 10 mg; fesoterodine fumarate in an amount of from 9.6 mg to 32 mg; glycopyrronium bromide in an amount of from 2.2 to 12 mg, normally from 2.2 to 8 mg; otilonium bromide in an amount of from 48 mg to 240 mg, normally from 48 mg to 160 mg; prifinium bromide in an amount of from 36 mg to 180 mg, normally from 36 mg to 120 mg; propiverine hydrochloride in an amount of from 18 mg to 180 mg; solifenacin succinate in an amount selected from the group consisting of from 5 mg to 60 mg, from 10 mg to 40 mg, from 12 mg to 30 mg, from 12 mg to 25 mg, and 21 mg; tolterodine tartrate in an amount of from 4.8 mg to 16 mg; timepidium bromide in an amount of from 36 mg to 180 mg, normally from 36 mg to 120 mg; trospium chloride, in an amount of from 24 mg to 240 mg; TTS-oxybutynin, in a released amount (from patch) of from 3.9 mg/24 h to 7.8 mg/24 h; and valethamate bromide in an amount of from 12 mg to 60 mg, in admixture with a pharmaceutical carrier or vehicle.

In all of these combinations, solifenacin succinate is preferably present as Component (c) in an amount selected from the group consisting of from 5 mg to 60 mg; from 10 mg to 40 mg, from 12 mg to 30 mg, from 12 mg to 25 mg; and 21 mg.

Any of the above MCRA/naAEA/nsPAChA combinations may contain, as a further component, Component (d), an AChEI also formulated in a pharmaceutical composition, said AChEI may include, but is not limited to, 1,2,3,4-tetrahydro-9-acridinamine (tacrine) and pharmaceutically acceptable salts and solvates thereof, (±)-2,3-dihydro-5,6-dimethoxy-2-[[1-(phenylmethyl)-4-piperidinyl]methyl]-1H-inden-1-one (donepezil) and pharmaceutically acceptable salt and solvates thereof, (S)—N-Ethyl-N-methyl-3-[1-(dimethylamino)ethyl]-phenyl carbamate (rivastigmine) and pharmaceutically acceptable salts and solvates thereof, or 4aS,6R,8aS-3-methoxy-11-methyl-4a,5,9,10,11,12-hexahydroxy-6H-benzofuro[3a,3,2-e,f]benzazepin-6-ol (galantamine) and pharmaceutically acceptable salts and solvates thereof.

Donepezil hydrochloride, available in 5-mg, 10-mg and 23-mg tablets; rivastigmine, preferably as free base or as hydrogen tartrate, available in 1.5-mg, 3-mg and 6-mg, capsules, as a 2-mg/dose oral solution, and in form of a transdermal patch releasing rivastigmine at 4.6 mg/24 hours, 9.5 mg/24 hour or 13.3 mg/24 h; and galantamine, preferably as hydrobromide, available as a 4-mg/ml oral solution, in 4-mg, 8-mg and 12-mg IR-tablets and in 8-mg, 16-mg and 24-mg ER-capsules; are particularly preferred AChEIs.

In said combination, said AChEI Component (d) may be formulated, in admixture with a pharmaceutical carrier or vehicle, in a pharmaceutical composition or device in dosage unit form or also used as a brand preparation.

For example, rivastigmine may be also used by orally administering EXELON® immediate-release 6 mg-capsules or by applying one or more EXELON® patches releasing 4.6 mg/24 hours, 9.5 mg/24 hours, or 13.3 mg/24 hours on the subject's skin, to daily release rivastigmine at a dose/24 h of from 4.6 mg to 53.2 mg or from 19.95 to 53.2 mg, normally from 14.1 mg to 46 m, in combination with the above-illustrated MCRA/naAEA combination.

Donepezil hydrochloride may be also used by orally administering one or more ARICEPT® immediate-release 5 mg- or 10 mg-tablets or the 23-mg tablets. In particular, donepezil hydrochloride may be orally administered, in combination with the above-illustrated MCRA/naAEA combination, at a daily dose of from 5 mg to 100 mg or from 15 mg to 70 mg.

Similarly, galantamine (as hydrobromide) may be also administered as a brand preparation, for example by orally administering RAZADYNE® immediate-release 8 mg- or 12 mg-tablets or RAZADYNE® ER 8 mg-, 16 mg- or 24 mg-capsules. In particular, galantamine hydrobromide may be orally administered, in combination with the above-illustrated MCRA/naAEA combination, at a daily dose (in galantamine) of from 36 mg to 96 mg, normally at a daily dose or from 36 mg to 72 mg, preferably in an ER-form.

The AChEI Component (d) when included with Component (a), Component (b) and/or Component (c) as described herein, may be present in an amount of from about 100% to about 1000% of a recommended dose of Component (d) contained in a unit form used for the treatment of Alzheimer type dementia.

Among the particularly preferred AChEIs, in the combinations of the present invention donepezil hydrochloride is generally present at a dose of from 5 mg to 98 mg, advantageously from 10 mg to 98 mg, advantageously from 15 mg to 69 mg, normally from 15 mg to 60 mg; rivastigmine, as hydrogen tartrate, is present, in a composition for oral administration, at a dose of from 6 mg to 30 mg, advantageously from 9 mg to 24 mg, normally 9 mg to 18 mg; as the free base, rivastigmine is present in patch releasing from 4.6 mg/24 h to 52 mg/24 h rivastigmine, advantageously from 9.6 mg/24 h to 39.9 mg/24 h, normally from 13.3 mg/24 h to 39.9 mg/24 h; and galantamine, as hydrobromide, is present in an amount of from 4 mg to 96 mg, advantageously from 12 mg to 96 mg, normally from 18 mg to 48 mg. The AChEI Component (d) is generally present in a pharmaceutical composition in admixture with a pharmaceutical carrier or vehicle.

Thus, according to another of its aspects, the present invention also provides a pharmaceutical combination comprising or essentially consisting of, as Components, (a) a pharmaceutical composition in dosage unit form essentially consisting of a MCRA, in admixture with a pharmaceutical carrier; and (b) a pharmaceutical composition in dosage unit form essentially consisting of a naAEA, in admixture with a pharmaceutical carrier or vehicle;

(c) a pharmaceutical composition in dosage unit form essentially consisting of a nsPAChA, in admixture with a pharmaceutical carrier or vehicle; and (d) a pharmaceutical composition in dosage unit form essentially consisting of an AChEI selected from the group consisting of donepezil hydrochloride in an amount of from 5 mg to 98 mg, advantageously from 15 mg to 69 mg, normally from 15 mg to 60 mg; rivastigmine, as hydrogen tartrate, in an amount, in rivastigmine, of from 1.5 mg to 30 mg, advantageously from 6 mg to 24 mg, normally from 9 mg to 18 mg; rivastigmine, as the free base, in patch releasing from 4.6 mg/24 h to 52 mg/24 h, advantageously from 9.6 mg/24 h to 39.9 mg/24 h, normally from 13.3 mg/24 h to 39.9 mg/24 h rivastigmine; and galantamine, as hydrobromide, in an amount (in galantamine) of from 4 mg to 96 mg, advantageously from 12 mg to 96 mg, normally from 18 mg to 48 mg, in admixture with a pharmaceutical carrier or vehicle.

According to this aspect, in the above combination the AChEI Component (d) may be combined with any MCRA Component (a), with any naAEA Component (b) and with any nsPAChA Component (c) illustrated in this section, in a quadruple combination useful for combating hypocholinergic disorders of the CNS.

The Combinations in Kits

The present invention also provides a kit or package containing a combination as described herein, accompanied by instructions for use. In particular, a kit of the present invention is a kit comprising a combination of medicaments for the treatment of hypocholinergic disorders of the CNS.

According to the present invention, the kit allows for the maximal functional capacity and safety during the treatment of a patient with a triple combination wherein the three components may be administered concurrently or sequentially.

Component (a), Component (b) and Component (c) may be present in the kit all in IR or in ER form or one of the Components is in IR form and at least one of the others are in ER form, each in admixture with a pharmaceutical carrier in a composition formulated as illustrated in "The Formulations" section, according to known technologies.

The kit according to the present invention may also comprise an AChEI Component (d), also in an IR or ER form, in admixture with a pharmaceutical carrier in a composition formulated as illustrated in "The Formulations" section below, according to known technologies.

When the AChEI Component (d) is present in the kit, it may be in a separate unit form wherein said AChEI is mixed with a pharmaceutical carrier in a pharmaceutical composition formulated in an IR or ER unit form.

More particularly, the kit of the present invention comprises (a) a pharmaceutical composition in IR or ER dosage unit form comprising or consisting essentially of a therapeutically effective amount of a MCRA in admixture with a pharmaceutical carrier or vehicle;

(b) a pharmaceutical composition in IR or ER dosage unit form comprising or consisting essentially of a therapeutically effective amount of a naAEA in admixture with a pharmaceutical carrier or vehicle; and (c) a pharmaceutical composition in IR or ER dosage unit form comprising or consisting essentially of a therapeutically effective amount of a nsPAChA in admixture with a pharmaceutical carrier or vehicle;

for concurrent, sequential or separate administration.

The pharmaceutical compositions may be packaged in any manner suitable for administration to a patient suffering from a hypocholinergic disorder of the CNS dementia and the packaging is manufactured according to known technologies and completed with instructions for use clearly showing to the patient or to the caregiver how to take each of the units forms to be administered.

Said kit comprises a Component (a) selected among the MCRAs illustrated in the above section "The MCRAs", a Component (b) selected among the naAEAs illustrated in the above section "The naAEAs" and a Component (c) selected among the nsPAChAs illustrated in the above section "The nsPAChAs" According to a first embodiment, the kit of the present invention comprises (a) a MCRA selected from the group consisting of AF267 and pharmaceutically acceptable salts and solvates thereof; cevimeline and pharmaceutically acceptable salts and solvates thereof; EUK 1001 and pharmaceutically acceptable salts and solvates thereof; milameline and pharmaceutically acceptable salts and solvates thereof; RS-86 and pharmaceutically acceptable salts and solvates thereof; sabcomeline and pharmaceutically acceptable salts and solvates thereof; talsaclidine and pharmaceutically acceptable salts and solvates thereof; tazomeline and pharmaceutically acceptable salts and solvates thereof; xanomeline and pharmaceutically acceptable salts and solvates thereof; AC-42 and pharmaceutically acceptable salts and solvates thereof; TBPB and pharmaceutically acceptable salts and solvates thereof; 4-Fluoro-6-methyl-1-[1-(tetrahydro-2H-pyran-4-yl)-4-piperidinyl]-1,3-dihydro-2H-benzimidazol-2-one and pharmaceutically acceptable salts and solvates thereof; 5-Fluoro-6-methyl-1-[1-(tetrahydro-2H-pyran-4-yl)-4-piperidinyl]-1,3-dihydro-2H-benzimidazol-2-one and pharmaceutically acceptable salts and solvates thereof; 4-(R)-ethyl-3-(2-methylbenzamido)-1,4'-bipiperidine-1'-carboxylate and pharmaceutically acceptable salts and solvates thereof; ethyl 3-[(3-exo)-(2-benzamidoethyl)amino]-8-azabicyclo[3.2.1]octane-8-carboxylate and pharmaceutically acceptable salts and solvates thereof; and MK-7622;

(b) a naAEA selected from the group consisting of a naAEA selected from the group consisting of (b1) 5HT3-antagonists, (b2) DA-antagonists, (b3) H1-antagonists, (b4) cannabinoids, (b5) NK1-antagonists and (c) a nsPAChA selected from the group consisting of anisotropine pharmaceutically acceptable quaternary salts, butylscopolamine pharmaceutically acceptable salts, cimetropium pharmaceutically acceptable salts, clidinium pharmaceutically acceptable salts, fesoterodine and pharmaceutically acceptable salts thereof, glycopyrronium pharmaceutically acceptable salts, otilonium pharmaceutically acceptable salts, oxyphencyclimine and pharmaceutically acceptable salts thereof, prifinium pharmaceutically acceptable salts, propiverine and pharmaceutically acceptable salts thereof, solifenacin and pharmaceutically acceptable salts thereof, tolterodine and pharmaceutically acceptable salts thereof, timepidium pharmaceutically acceptable salts, trospium pharmaceutically acceptable salts, TTS-oxybutynin; and valethamate pharmaceutically acceptable salts; and TTS-oxybutynin, in admixture with a pharmaceutical carrier or vehicle;

said combination being in a fixed-dose combination formulated in admixture with a pharmaceutical carrier or vehicle for IR or ER administration.

Alternatively, Component (c) is preferably, a nsPAChA selected from the group consisting of quaternary ammonium nsPAChAs, sulfonium nsPAChAs, solifenacin and its pharmaceutically acceptable salts, propiverine and its pharmaceutically acceptable salts, oxyphencyclimine and its pharmaceutically acceptable salts, tolterodine and its pharmaceutically acceptable salts, fesoterodine and its pharmaceutically acceptable salts.

According to this first embodiment, the fixed-dose (a/b/c) combination, illustrated in the "The Fixed Combinations" section, is administered to a patient in need of the treatment as a single unite form at the doses illustrated in said section.

A preferred kit according to this first embodiment, the kit of the present invention comprises (a) a MCRA selected from the group consisting of cevimeline hydrochloride hemihydrate, in an amount of from 34.5 mg to 180 mg, xanomeline, as free base, as oxalate or as L-tartrate, in an amount of from 90 mg to 450 mg, milameline hydrochloride, in an amount of from 2.4 mg to 12 mg and MK 7622, as free base, as hydrochloride, as fumarate or as methanesulfonate, in an amount of from 5 mg to 270 mg;

(b) a naAEA selected from the group consisting of alosetron and pharmaceutically acceptable salts and solvates thereof, in particular the hydrochloride, in an amount (in alosetron) of from 0.25 mg to 6 mg; azasetron and pharmaceutically acceptable salts and solvates thereof, in particular the hydrochloride, in an amount (in azasetron) of from 5 mg to 60 mg; dolasetron and pharmaceutically acceptable salts and solvates thereof, in particular the mesylate, in an amount (in dolasetron) of from 25 mg to 600 mg; granisetron and pharmaceutically acceptable salts and solvates thereof, in particular the hydrochloride, in an amount (in granisetron) of from 0.5 mg to 6 mg; ondansetron and pharmaceutically acceptable salts and solvates thereof, in particular the hydrochloride dihydrate, in an amount (in ondansetron) of from 2 mg to 64 mg; palonosetron and pharmaceutically acceptable salts and solvated thereof, in particular its hydrochloride, in an amount (in palonosetron) of from 0.25 mg to 3 mg; ramosetron and pharmaceutically acceptable salts and solvates thereof, in particular its hydrochloride, in an amount (in ramosetron) of from 0.0125 mg to 0.3 mg; tropisetron and pharmaceutically acceptable salts and solvates thereof, in particular the hydrochloride, in an amount of from 2.5 mg to 30 mg; domperidone and pharmaceutically acceptable salts and solvates thereof, in an amount (in domperidone) of from 5 mg to 60 mg; haloperidol, in an amount of from 0.5 mg to 60 mg; chlorpromazine and pharmaceutically acceptable salts and solvates thereof, in particular the hydrochloride, in an amount (in chlorpromazine) of from 12.5 mg to 600 mg; prochlorperazine and pharmaceutically acceptable salts and solvates thereof, in particular the dimaleate, in an amount (in prochlorperazine) of from 2.5 mg to 30 mg; metoclopramide and pharmaceutically acceptable salts and solvates thereof, in particular the monohydrochloride monohydrate, in an amount (in metoclopramide) of from 5 mg to 60 mg; bromopride and pharmaceutically acceptable salts and solvates, in particular the monohydrochloride and the dihydrochloride monohydrate, in an amount (in bromopride) of from 5 mg to 60 mg; clebopride and pharmaceutically acceptable salts and solvates thereof, in particular the hydrogen malate and the hydrochloride monohydrate, in an amount (in clebopride) of from 0.25 mg to 3 mg; levosulpiride, in an amount of from 12.5 mg to 600 mg; alizapride and pharmaceutically acceptable salts thereof, in particular the hydrochloride, in an amount (in alizapride) of from 25 mg to 300 mg; trimethobenzamide and pharmaceutically acceptable salts thereof such as the monohydrochloride, in an amount (in trimethobenzamide) of from 50 mg to 600 mg; meclizine (also called meclozine) and pharmaceutically acceptable salts and solvates thereof, in an amount (in meclizine) of from 6.25 mg to 300 mg; promethazine and pharmaceutically acceptable salts and solvates thereof, in particular the hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant, in an amount of from 25 mg to 300 mg; and (c) a nsPAChA selected from the group consisting of propiverine and pharmaceutically acceptable salts thereof, in an amount corresponding to from 15 mg to 240 mg of propiverine hydrochloride, trospium pharmaceutically acceptable salts, in an amount corresponding to from 20 mg to 480 mg of trospium chloride; and glycopyrronium pharmaceutically acceptable salts corresponding to from 2 mg to 16 mg of glycopyrronium bromide, in admixture with a pharmaceutical carrier or vehicle.

According to this first embodiment, the fixed-dose (a/b/c) combination illustrated in the "The Fixed Combinations" section, is administered to a patient in need of the treatment as a single unit form at the doses illustrated in said section.

According to a second embodiment, the invention provides a kit comprising (a) a pharmaceutical composition in dosage unit form comprising or consisting essentially of a MCRA in admixture with a pharmaceutical carrier or vehicle; and (b/c) a fixed-dose combination that is a pharmaceutical composition comprising or consisting essentially of (b) a naAEA; and (c) a nsPAChA in admixture with a pharmaceutical carrier or vehicle.

According to an advantageous embodiment, in all the (b/c) fixed dose combination in the kits of this section, the nsPAChA is selected from the group consisting of anisotropine pharmaceutically acceptable quaternary salts, butylscopolamine pharmaceutically acceptable salts, cimetropium pharmaceutically acceptable salts, clidinium pharmaceutically acceptable salts, fesoterodine and pharmaceutically acceptable salts thereof, glycopyrronium pharmaceutically acceptable salts, otilonium pharmaceutically acceptable salts, oxyphencyclimine and pharmaceutically acceptable salts thereof, prifinium pharmaceutically acceptable salts, propiverine and pharmaceutically acceptable salts thereof, solifenacin and pharmaceutically acceptable salts thereof, tolterodine and pharmaceutically acceptable salts thereof, timepidium pharmaceutically acceptable salts, trospium pharmaceutically acceptable salts, TTS-oxybutynin; and valethamate pharmaceutically acceptable salts, in admixture with a pharmaceutical carrier or vehicle.

Preferably said nsPAChA in said (b/c) fixed-dose combination of said kit is selected from the group consisting of glycopyrronium pharmaceutically acceptable salts, at a dose that is equivalent to from 1 mg to 24 mg of glycopyrronium bromide; propiverine and pharmaceutically acceptable salts thereof, at a dose that is equivalent to from 15 mg to 240 mg of propiverine hydrobromide; solifenacin and pharmaceutically acceptable salts thereof, at a dose that is equivalent to from 5 mg to 40 mg of solifenacin succinate; trospium pharmaceutically acceptable salts, at a dose that is equivalent to from 20 mg to 480 mg of trospium chloride; and TTS-oxybutynin, at a dose of from 3.9 mg to 7.8 mg. Said doses are referred to daily administered doses.

This kit has the advantage of allowing an improvement in the treatment of a patient suffering from a hypocholinergic disorder. In fact, in the case of the prescription of a MCRA that must be taken three or four times/day the kit of the present invention allows the administration of a composition (b/c) comprising a naAEA and a nsPAChA that may be administered once a day, thus rendering the treatment easier for the patient or for the caregiver. In addition, the naAEA and the nsPAChA present in said composition act synergistically thus allowing for an increase of the $M_2$-antagonist dose.

For example, a kit according to this second embodiment may comprise:

(a) a pharmaceutical composition in dosage unit form comprising or consisting essentially of a MCRA selected from the group consisting of 1-methylpiperidine-4-spiro-5'(2'-ethyl-1',4'-thiazoline-3'-one) (AF267) and pharmaceutically acceptable salts and solvates thereof; cis-2'-methylspiro {1-azabicyclo[2.2.2]octane-3,5'-[1,3]oxathiolane} (cevimeline) and pharmaceutically acceptable salts and solvates thereof; 3-[3-(3-(3-fluorophenyl)-2-propyn-1-yl-thio)-1,2,5-thiadiazol-4-yl]-1,2,5,6-tetrahydro-1-methyl-pyridine and pharmaceutically acceptable salts and solvates thereof; (E)-N-methoxy-1-(1-methyl-1,2,5,6-tetrahydropyridin-3-yl)methanimine (milameline) and pharmaceutically acceptable salts and solvates thereof; 2-ethyl-8-methyl-2,8-diazaspiro[4.5]decane-1,3-dione (RS-86) and pharmaceutically acceptable salts and solvates thereof; (3R)—N-methoxyquinuclidine-3-carboximidoyl cyanide (sabcomeline) and pharmaceutically acceptable salts and solvates thereof; (3R)-3-(prop-2-yn-1-yloxy)-1-azabicyclo[2.2.2]octane (talsaclidine) and pharmaceutically acceptable salts and solvates thereof; 5-[4-(hexylsulfanyl)-1,2,5-thiadiazol-3-yl]-1-methyl-1,2,3,6-tetrahydropyridine (tazomeline) and pharmaceutically acceptable salts and solvates thereof; 3-(4-hexyloxy-1,2,5-thiadiazol-3-yl)-1-methyl-5,6-dihydro-2H-pyridine (xanomeline), and pharmaceutically acceptable salts and solvates thereof; 5-(3-ethyl-1,2,4-oxadiazol-5-yl)-1,4,5,6-tetrahydropyrimidine (MCD-386) and pharmaceutically acceptable salts and solvates thereof; 3-Methyl-5-(piperidin-3-yl)-1,2,4-oxadiazole, its enantiomers and pharmaceutically acceptable salts and solvates thereof; 3-[(1S,2S)-2-hydroxycyclohexyl]-6-[(6-methylpyridin-3-yl)methyl]benzo[h]quinazolin-4(3H)-one (MK-7622) and pharmaceutically acceptable salts and solvates thereof, in admixture with a pharmaceutical carrier or vehicle; and (b/c) a fixed-dose combination that is a pharmaceutical composition comprising or consisting essentially of (b) a naAEA selected from the group consisting of alosetron and pharmaceutically acceptable salts and solvates thereof, especially its hydrochloride; azasetron and pharmaceutically acceptable salts and solvates thereof, especially its hydrochloride; ondansetron and pharmaceutically acceptable salts and solvates thereof, especially its monohydrochloridedihydrate; granisetron and pharmaceutically acceptable salts and solvates thereof, especially its hydrochloride; dolasetron and pharmaceutically acceptable salts and solvates thereof, especially its monomethanesulfonate monohydrate, ramosetron and pharmaceutically acceptable salts and solvates thereof, especially its hydrochloride; tropisetron and pharmaceutically acceptable salts and solvates thereof, especially its hydrochloride; palonosetron and pharmaceutically acceptable salts and solvates thereof, especially its hydrochloride; domperidone and pharmaceutically acceptable salts and solvates thereof, especially its maleate; metoclopramide and pharmaceutically acceptable salts and solvates thereof, especially its hydrochloride monohydrate; bromopride and pharmaceutically acceptable salts and solvates thereof, especially its monohydrochloride or the dihydrochloride monohydrate; alizapride and pharmaceutically acceptable salts and solvates thereof, especially its hydrochloride; clebopride and pharmaceutically acceptable salts and solvates thereof, especially its malate and the hydrochloride monohydrate; meclizine (meclozine) and pharmaceutically acceptable salts and solvates thereof, especially its hydrochloride monohydrate; promethazine and pharmaceutically acceptable salts and solvates thereof, especially its hydrochloride; chlorpromazine and pharmaceutically acceptable salts and solvates thereof, especially its hydrochloride; prochlorperazine and pharmaceutically acceptable salts and solvates thereof, especially its dimaleate, its dimesylate and its the 1,2-ethanedisulfonate (1:1) (edisilate); hydroxyzine and pharmaceutically acceptable salts and solvates thereof such as the dihydrochloride or the 1,1'-methylene bis(2-hydroxy-3-naphthalenecarboxylic acid (pamoate) dronabinol; nabilone; aprepitant, netupitant, rolapitant, and casopitant; and (c) a nsPAChA selected from the group consisting of quaternary ammonium nsPAChAs, sulfonium nsPAChAs, (1S)-(3R)-1-azabicyclo[2.2.2]oct-3-yl 3,4-dihydro-1-phenyl-2(1H)-iso-quinolinecarboxylate (solifenacin) and its pharmaceutically acceptable salts, 1-methylpiperidin-4-yl) 2,2-di(phenyl)-2-propoxyacetate (propiverine) and its pharmaceutically acceptable salts, 1,4,5,6-tetrahydro-1-methylpyrimidin-2-ylmethyl α-cyclohexyl-α-hydroxy-α-phenylacetate (oxyphencyclimine) and its pharmaceutically acceptable salts, (R)—N,N-diisopropyl-3-(2-hydroxy-5-methylphenyl)-3-phenylpropanamine (tolterodine) and its pharmaceutically acceptable salts, [2-[(1R)-3-(Di(propan-2-yl)amino)-1-phenylpropyl]-4-(hydroxymethyl)phenyl]2-methylpropanoate (fesoterodine) and its pharmaceutically acceptable salts in admixture with a pharmaceutical carrier or vehicle.

Another kit of this second embodiment may comprise:
(a) a pharmaceutical composition in dosage unit form comprising or consisting essentially of a MCRA selected from the group consisting of cevimeline hydrochloride hemihydrate, in an amount of from 34.5 mg to 180 mg, xanomeline, as free base, as oxalate or as L-tartrate, in an amount of from 90 mg to 450 mg, milameline hydrochloride, in an amount of from 2.4 mg to 12 mg and MK 7622, as free base, as hydrochloride, as fumarate or as methanesulfonate, in an amount selected from the group consisting of from more than 5 mg to 15 mg, from more than 15 mg to 45 mg, from more than 45 mg to 270 mg, from more than 15 mg to 225 mg, from more than 45 mg to 225 mg, and from 54 mg to 180 mg,
in admixture with a pharmaceutical carrier or vehicle; and
(b/c) a fixed-dose combination that is a pharmaceutical composition comprising or consisting essentially of
(b) a naAEA selected from the group consisting of alosetron hydrochloride, in an amount (in alosetron) of from 0.25 mg to 6 mg; azasetron hydrochloride, in an amount (in azasetron) of from 5 mg to 60 mg; dolasetron mesylate, in an amount (in dolasetron) of from 25 mg to 600 mg; granisetron hydrochloride, in an amount (in granisetron) of from 0.5 mg to 6 mg; ondansetron hydrochloride dihydrate, in an amount (in ondansetron) of from 2 mg to 64 mg; palonosetron hydrochloride, in an amount (in palonosetron) of from 0.25 mg to 3 mg; ramosetron hydrochloride, in an amount (in ramosetron) of from 0.0125 mg to 0.3 mg, tropisetron hydrochloride, in an amount (in tropisetron) of from 2.5 mg to 30 mg; domperidone and pharmaceutically acceptable salts and solvates thereof, in an amount (in domperidone) of from 5 mg to 60 mg; haloperidol, in an amount of from 0.5 mg to 60 mg; chlorpromazine hydrochloride, in an amount (in chlorpromazine) of from 12.5 mg to 600 mg; prochlorperazinedimaleate, in an amount (in prochlorperazine) of from 2.5 mg to 30 mg; metoclopramide monohydrochloride monohydrate, in an amount (in metoclopramide) of from 5 mg to 60 mg; bromopride monohydrochloride or dihydrochloride monohydrate, in an amount (in bromopride) of from 5 mg to 60 mg; clebopride hydrogen malate or hydrochloride monohydrate, in an amount (in clebopride) of from 0.25 mg to 3 mg; levosulpiride, in an amount of from 12.5 mg to 600 mg; alizapride hydrochloride, in an amount (in alizapride) of from 25 mg to 300 mg; trimethobenzamide monohydrochloride, in an amount (in trimethobenzamide) of from 50 mg to 600 mg; meclizine (also called meclozine) and pharmaceutically acceptable salts and solvates thereof, in an amount (in meclizine) of from 6.25 mg to 300 mg; promethazine hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant, in an amount of from 25 mg to 300 mg; in a pharmaceutical composition in admixture with a pharmaceutical carrier or vehicle; and (c) a nsPAChA selected from the group consisting of glycopyrronium pharmaceutically acceptable salts, in an amount that is equivalent to from 0.5 mg to 16 mg of glycopyrronium bromide; propiverine and pharmaceutically acceptable salts thereof, in an amount that is equivalent to from 7.5 mg to 240 mg of propiverine hydrobromide; solifenacin and pharmaceutically acceptable salts thereof, in an amount that is equivalent to from 5 mg to 60 mg, preferably from 5 mg to 40 mg, of solifenacin succinate; trospium pharmaceutically acceptable salts, in an amount that is equivalent to from 20 mg to 480 mg of trospium chloride; and TTS-oxybutynin, in a released amount of from 3.9 mg/24 h to 7.8 mg/24 h,
in admixture with a pharmaceutical carrier or vehicle.

A further kit of this second embodiment may comprise:
(a) a pharmaceutical composition in dosage unit form comprising or consisting essentially of a MCRA selected from the group consisting of cevimeline hydrochloride hemihydrate, in an amount of from 34.5 mg to 180 mg, xanomeline, as free base, as oxalate or as L-tartrate, in an amount of from 90 mg to 450 mg, milameline hydrochloride, in an amount of from 2.4 mg to 12 mg and MK 7622, as free base, as hydrochloride, as fumarate or as methanesulfonate, in an amount selected from the group consisting of from more than 5 mg to 15 mg, from more than 15 mg to 45 mg, from more than 45 mg to 270 mg, from more than 15 mg to 225 mg, from more than 45 mg to 225 mg, and from 54 mg to 180 mg, in admixture with a pharmaceutical carrier or vehicle; and (b/c) a fixed-dose combination that is a pharmaceutical composition comprising or consisting essentially of (b) a naAEA selected from the group consisting of alosetron hydrochloride, in an amount (in alosetron) of from 0.25 mg to 6 mg; azasetron hydrochloride, in an amount (in azasetron) of from 5 mg to 60 mg; dolasetron mesylate, in an amount (in dolasetron) of from 25 mg to 600 mg; granisetron hydrochloride, in an amount (in granisetron) of from 0.5 mg to 6 mg; ondansetron hydrochloride dihydrate, in an amount (in ondansetron) of from 2 mg to 64 mg; palonosetron hydrochloride, in an amount (in palonosetron) of from 0.25 mg to 3 mg; ramosetron hydrochloride, in an amount (in ramosetron) of from 0.0125 mg to 0.3 mg, tropisetron hydrochloride, in an amount (in tropisetron) of from 2.5 mg to 30 mg; domperidone and pharmaceutically acceptable salts and solvates thereof, in an amount (in domperidone) of from 5 mg to 60 mg; haloperidol, in an amount of from 0.5 mg to 60 mg; chlorpromazine hydrochloride, in an amount (in chlorpromazine) of from 12.5 mg to 600 mg; prochlorperazinedimaleate, in an amount (in prochlorperazine) of from 2.5 mg to 30 mg; metoclopramide monohydrochloride monohydrate, in an amount (in metoclopramide) of from 5 mg to 60 mg; bromopride monohydrochloride or dihydrochloride monohydrate, in an amount (in bromopride) of from 5 mg to 60 mg; clebopride hydrogen malate or hydrochloride monohydrate, in an amount (in clebopride) of from 0.25 mg to 3 mg; levosulpiride, in an amount of from 12.5 mg to 600 mg; alizapride hydrochloride, in an amount (in alizapride) of from 25 mg to 300 mg; trimethobenzamide monohydrochloride, in an amount (in trimethobenzamide) of from 50 mg to 600 mg; meclizine (also called meclozine) and pharmaceutically acceptable salts and solvates thereof, in an amount (in meclizine) of from 6.25 mg to 300 mg; promethazine hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant, in an amount of from 25 mg to 300 mg; in a pharmaceutical composition in admixture with a pharmaceutical carrier or vehicle; and (c) a nsPAChA selected from the group consisting of anisotropine methylbromide, in an amount of from 120 mg to 400 mg; butylscopolamine bromide, in an amount of from 12 mg to 40 mg; cimetropium bromide, in an amount of from 55 mg to 200 mg; clidinium bromide, in an amount of from 3 mg to 10 mg; fesoterodine fumarate, in an amount of from 9.6 mg to 32 mg; glycopyrronium bromide, in an amount of from 2.4 mg to 8 mg; otilonium bromide, in an amount of from 48 mg to 160 mg; oxyphencyclimine, in an amount of from 18 mg to 60 mg; prifinium bromide, in an amount of from 36 mg to 120 mg; propiverine hydrochloride IR, in an amount of from 18 mg to 90 mg; solifenacin succinate, in an amount selected from the group consisting of from 5 mg to 60 mg, from 10 mg to 40 mg, from 12 mg to 30 mg, from 12 mg to 25 mg, and 21 mg; tolterodine tartrate, in an amount of from 4.8 mg to 16 mg; timepidium bromide, in an amount of from 36 mg to 120 mg; trospium chloride, in an amount of from 24 mg to 240 mg; and valethamate bromide, in an amount of from 12 mg to 40 mg in admixture with a pharmaceutical carrier or vehicle.

Preferred pharmaceutical compositions that may be used in a kit of this second embodiment may be compositions comprising or consisting essentially of, as Component (b/c), a naAEA (b) and a nsPAChA (c) selected from the group consisting of glycopyrronium pharmaceutically acceptable salts, especially the bromide, trospium pharmaceutically acceptable salts, especially the chloride, propiverine and its pharmaceutically acceptable addition salts, especially the hydrochloride; and solifenacin its pharmaceutically acceptable addition salts, especially the succinate. These pharmaceutically composition in dosage unit form are disclosed in US 2015/0231122, the contents of which are incorporated herein by reference in their entirety.

One of these preferred compositions is a composition comprising or consisting essentially of, for example:

(a) a pharmaceutical composition in dosage unit form comprising or consisting essentially of a MCRA consisting of MK 7622 free base, as MK 7622 hydrochloride, MK 7622 fumarate and MK 7622 methanesulfonate, in an amount selected from the group consisting of from more than 5 mg to 15 mg, from more than 15 mg to 45 mg, from more than 45 mg to 270 mg, from more than 15 mg to 225 mg, from more than 45 mg to 225 mg, and from 54 mg to 180 mg, in admixture with a pharmaceutical carrier or vehicle; and (b/c) a fixed-dose combination that is a pharmaceutical composition comprising or consisting essentially of (b) a naAEA consisting of ondansetron hydrochloride dihydrate, in an amount (in ondansetron of from 4 mg to 24 mg, preferably from 8 mg to 24 mg; and (c) a nsPAChA consisting of solifenacin succinate, in an amount selected from the group consisting of from 5 mg to 60 mg, from 10 mg to 40 mg, from 12 mg to 30 mg, from 12 mg to 25 mg, and 21 mg, in admixture with a pharmaceutical carrier or vehicle.

According to a third embodiment, the invention provides a kit comprising (a/c) a fixed-dose combination that is a pharmaceutical composition comprising or consisting essentially of (a) a MCRA; and (c) a nsPAChA in admixture with a pharmaceutical carrier or vehicle; and (b) a pharmaceutical composition in dosage unit form comprising or consisting essentially of a naAEA in admixture with a pharmaceutical carrier or vehicle.

An advantageous kit according to this third embodiment provides a kit comprising:

(a/c) a fixed-dose combination that is a pharmaceutical composition comprising or consisting essentially of (a) a MCRA selected from the group consisting of 1-methylpiperidine-4-spiro-5'(2'-ethyl-1',4'-thiazoline-3'-one) (AF267) and pharmaceutically acceptable salts and solvates thereof; cis-2'-methylspiro {1-azabicyclo [2.2.2]octane-3,5'-[1,3]oxathiolane} (cevimeline) and pharmaceutically acceptable salts and solvates thereof; 3-[3-(3-(3-fluorophenyl)-2-propyn-1-ylthio)-1,2,5-thiadiazol-4-yl]-1,2,5,6-tetrahydro-1-methylpyridine and pharmaceutically acceptable salts and solvates thereof; (E)-N-methoxy-1-(1-methyl-1,2,5,6-tetrahydropyridin-3-yl)methanimine (milameline) and pharmaceutically acceptable salts and solvates thereof; 2-ethyl-8-methyl-2,8-diazaspiro[4.5]decane-1,3-dione (RS-86) and pharmaceutically acceptable salts and solvates thereof; (3R)—N-methoxyquinuclidine-3-carboximidoyl cyanide (sabcomeline) and pharmaceutically acceptable salts and solvates thereof; (3R)-3-

(prop-2-yn-1-yloxy)-1-azabicyclo[2.2.2]octane (talsaclidine) and pharmaceutically acceptable salts and solvates thereof; 5-[4-(hexylsulfanyl)-1,2,5-thiadiazol-3-yl]-1-methyl-1,2,3,6-tetrahydropyridine (tazomeline) and pharmaceutically acceptable salts and solvates thereof; 3-(4-hexyloxy-1,2,5-thiadiazol-3-yl)-1-methyl-5,6-dihydro-2H-pyridine (xanomeline), and pharmaceutically acceptable salts and solvates thereof; 5-(3-ethyl-1,2,4-oxadiazol-5-yl)-1,4,5,6-tetrahydropyrimidine (MCD-386) and pharmaceutically acceptable salts and solvates thereof; 3-Methyl-5-(piperidin-3-yl)-1,2,4-oxadiazole, its enantiomers and pharmaceutically acceptable salts and solvates thereof; 3-[(1S,2S)-2-hydroxycyclohexyl]-6-[(6-methylpyridin-3-yl)methyl]benzo[h]quinazolin-4(3H)-one (MK-7622) and pharmaceutically acceptable salts and solvates thereof, and (c) a nsPAChA selected from the group consisting of anisotropine pharmaceutically acceptable salts, butylscopolamine pharmaceutically acceptable salts, cimetropium pharmaceutically acceptable salts, clidinium pharmaceutically acceptable salts, fesoterodine and pharmaceutically acceptable salts thereof, glycopyrronium pharmaceutically acceptable salts, otilonium pharmaceutically acceptable salts, oxyphencyclimine and pharmaceutically acceptable salts thereof, prifinium pharmaceutically acceptable salts, propiverine and pharmaceutically acceptable salts thereof, solifenacin and pharmaceutically acceptable salts thereof, tolterodine and pharmaceutically acceptable salts thereof, timepidium pharmaceutically acceptable salts, trospium pharmaceutically acceptable salts and valethamate pharmaceutically acceptable salts, in admixture with a pharmaceutical carrier or vehicle; and (b) a pharmaceutical composition in dosage unit form comprising or consisting essentially of a naAEA selected from the group consisting of alosetron and pharmaceutically acceptable salts and solvates thereof, especially its hydrochloride; azasetron and pharmaceutically acceptable salts and solvates thereof, especially its hydrochloride; ondansetron and pharmaceutically acceptable salts and solvates thereof, especially its monohydrochloride dihydrate; granisetron and pharmaceutically acceptable salts and solvates thereof, especially its hydrochloride; dolasetron and pharmaceutically acceptable salts and solvates thereof, especially its monomethanesulfonate monohydrate, ramosetron and pharmaceutically acceptable salts and solvates thereof, especially its hydrochloride; tropisetron and pharmaceutically acceptable salts and solvates thereof, especially its hydrochloride; palonosetron and pharmaceutically acceptable salts and solvates thereof, especially its hydrochloride; domperidone and pharmaceutically acceptable salts and solvates thereof, especially its maleate; metoclopramide and pharmaceutically acceptable salts and solvates thereof, especially its hydrochloride monohydrate; bromopride and pharmaceutically acceptable salts and solvates thereof, especially its monohydrochloride or the dihydrochloride monohydrate; alizapride and pharmaceutically acceptable salts and solvates thereof, especially its hydrochloride; clebopride and pharmaceutically acceptable salts and solvates thereof, especially its malate and the hydrochloride monohydrate; meclizine (meclozine) and pharmaceutically acceptable salts and solvates thereof, especially its hydrochloride monohydrate; promethazine and pharmaceutically acceptable salts and solvates thereof, especially its hydrochloride; chlorpromazine and pharmaceutically acceptable salts and solvates thereof, especially its hydrochloride; prochlorperazine and pharmaceutically acceptable salts and solvates thereof, especially its dimaleate, its dimesylate and its the 1,2-ethanedisulfonate (1:1) (edisilate); hydroxyzine and pharmaceutically acceptable salts and solvates thereof such as the dihydrochloride or the 1,1'-methylene bis(2-hydroxy-3-naphthalenecarboxylic acid (pamoate) dronabinol; nabilone; aprepitant; netupitant; rolapitant; and casopitant; in admixture with a pharmaceutical carrier or vehicle.

Another advantageous kit according to this third embodiment provides a kit comprising:

(a/c) a novel fixed-dose combination that is a pharmaceutical composition comprising or consisting essentially of (a) a MCRA selected from the group consisting of cevimeline hydrochloride hemihydrate, in an amount of from 34.5 mg to 180 mg, xanomeline, as free base, as oxalate or as L-tartrate, in an amount of from 90 mg to 450 mg, milameline hydrochloride, in an amount of from 2.4 mg to 12 mg and MK 7622, as free base, as hydrochloride, as fumarate or as methanesulfonate, in an amount selected from the group consisting of from more than 5 mg to 15 mg, from more than 15 mg to 45 mg, from more than 45 mg to 270 mg, from more than 15 mg to 225 mg, from more than 45 mg to 225 mg, and from 54 mg to 180 mg, and (c) a nsPAChA selected from the group consisting of glycopyrronium pharmaceutically acceptable salts, in an amount that is equivalent to from 0.5 mg to 16 mg of glycopyrronium bromide; propiverine and pharmaceutically acceptable salts thereof, in an amount that is equivalent to from 7.5 mg to 240 mg of propiverine hydrobromide; solifenacin and pharmaceutically acceptable salts thereof, in an amount that is equivalent to from 5 mg to 60 mg, preferably from 5 mg to 40 mg, of solifenacin succinate; trospium pharmaceutically acceptable salts, in an amount that is equivalent to from 20 mg to 480 mg of trospium chloride; and TTS-oxybutynin, in a released amount of from 3.9 mg/24 h to 7.8 mg/24 h, in admixture with a pharmaceutical carrier, and (b) a pharmaceutical composition in dosage unit form comprising or consisting essentially of a naAEA selected from the group consisting of alosetron hydrochloride, in an amount (in alosetron) of from 0.25 mg to 6 mg; azasetron hydrochloride, in an amount (in azasetron) of from 5 mg to 60 mg; dolasetron mesylate, in an amount (in dolasetron) of from 25 mg to 600 mg; granisetron hydrochloride, in an amount (in granisetron) of from 0.5 mg to 6 mg; ondansetron hydrochloride dihydrate, in an amount (in ondansetron) of from 2 mg to 64 mg; palonosetron hydrochloride, in an amount (in palonosetron) of from 0.25 mg to 3 mg; ramosetron hydrochloride, in an amount (in ramosetron) of from 0.0125 mg to 0.3 mg, tropisetron hydrochloride, in an amount (in tropisetron) of from 2.5 mg to 30 mg; domperidone and pharmaceutically acceptable salts and solvates thereof, in an amount (in domperidone) of from 5 mg to 60 mg; haloperidol, in an amount of from 0.5 mg to 60 mg; chlorpromazine hydrochloride, in an amount (in chlorpromazine) of from 12.5 mg to 600 mg; prochlorperazine dimaleate, in an amount (in prochlorperazine) of from 2.5 mg to 30 mg; metoclopramide monohydrochloride monohydrate, in an amount (in metoclopramide) of from 5 mg to 60 mg; bromopride monohydrochloride or dihydrochloride monohydrate, in an amount (in bromopride) of from 5 mg to 60 mg; clebopride hydrogen malate or hydrochloride monohydrate, in an amount (in clebopride) of from 0.25 mg to 3 mg; levosulpiride, in an amount of from 12.5 mg to 600 mg; alizapride hydrochloride, in an amount (in alizapride) of from 25 mg to 300 mg; trimethobenzamide monohydrochloride, in an amount (in trimethobenzamide) of from 50 mg to 600 mg; meclizine (also called meclozine) and pharmaceutically acceptable salts and solvates thereof, in an amount (in meclizine) of from 6.25 mg to 300 mg; promethazine hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant, in an amount of from 25 mg to 300 mg, in admixture with a pharmaceutical carrier or vehicle.

A specific kit according to this third embodiment comprises (a/c) a novel fixed-dose combination that is a pharmaceutical composition comprising or consisting essentially of
  (a) a MCRA selected from the group consisting of cevimeline hydrochloride hemihydrate, in an amount of from 34.5 mg to 180 mg, xanomeline, as free base, as oxalate or as L-tartrate, in an amount of from 90 mg to 450 mg, milameline hydrochloride, in an amount of from 2.4 mg to 12 mg and MK 7622, as free base, as hydrochloride, as fumarate or as methanesulfonate, in an amount selected from the group consisting of from more than 5 mg to 15 mg, from more than 15 mg to 45 mg, from more than 45 mg to 270 mg, from more than 15 mg to 225 mg, from more than 45 mg to 225 mg, and from 54 mg to 180 mg, and
  (c) a nsPAChA selected from the group consisting of anisotropine methylbromide, in an amount of from 120 mg to 400 mg; butylscopolamine bromide, in an amount of from 12 mg to 40 mg; cimetropium bromide, in an amount of from 55 mg to 200 mg; clidinium bromide, in an amount of from 3 mg to 10 mg; fesoterodine fumarate, in an amount of from 9.6 mg to 32 mg; glycopyrronium bromide, in an amount of from 2.4 mg to 8 mg; otilonium bromide, in an amount of from 48 mg to 160 mg; oxyphencyclimine, in an amount of from 18 mg to 60 mg; prifinium bromide, in an amount of from 36 mg to 120 mg; propiverine hydrochloride IR, in an amount of from 18 mg to 90 mg; solifenacin succinate, in an amount selected from the group consisting of from 5 mg to 60 mg, from 10 mg to 40 mg, from 12 mg to 30 mg, from 12 mg to 25 mg, and 21 mg; tolterodine tartrate, in an amount of from 4.8 mg to 16 mg; timepidium bromide, in an amount of from 36 mg to 120 mg; trospium chloride, in an amount of from 24 mg to 240 mg; and valethamate bromide, in an amount of from 12 mg to 40 mg,
in admixture with a pharmaceutical carrier or vehicle; and
  (b) a pharmaceutical composition in dosage unit form comprising or consisting essentially of a naAEA selected from the group consisting of alosetron hydrochloride, in an amount (in alosetron) of from 0.25 mg to 6 mg; azasetron hydrochloride, in an amount (in azasetron) of from 5 mg to 60 mg; dolasetron mesylate, in an amount (in dolasetron) of from 25 mg to 600 mg; granisetron hydrochloride, in an amount (in granisetron) of from 0.5 mg to 6 mg; ondansetron hydrochloride dihydrate, in an amount (in ondansetron) of from 2 mg to 64 mg; palonosetron hydrochloride, in an amount (in palonosetron) of from 0.25 mg to 3 mg; ramosetron hydrochloride, in an amount (in ramosetron) of from 0.0125 mg to 0.3 mg, tropisetron hydrochloride, in an amount (in tropisetron) of from 2.5 mg to 30 mg; domperidone and pharmaceutically acceptable salts and solvates thereof, in an amount (in domperidone) of from 5 mg to 60 mg; haloperidol, in an amount of from 0.5 mg to 60 mg; chlorpromazine hydrochloride, in an amount (in chlorpromazine) of from 12.5 mg to 600 mg; prochlorperazine dimaleate, in an amount (in prochlorperazine) of from 2.5 mg to 30 mg; metoclopramide monohydrochloride monohydrate, in an amount (in metoclopramide) of from 5 mg to 60 mg; bromopride monohydrochloride or dihydrochloride monohydrate, in an amount (in bromopride) of from 5 mg to 60 mg; clebopride hydrogen malate or hydrochloride monohydrate, in an amount (in clebopride) of from 0.25 mg to 3 mg; levosulpiride, in an amount of from 12.5 mg to 600 mg; alizapride hydrochloride, in an amount (in alizapride) of from 25 mg to 300 mg; trimethobenzamide monohydrochloride, in an amount (in trimethobenzamide) of from 50 mg to 600 mg; meclizine (also called meclozine) and pharmaceutically acceptable salts and solvates thereof, in an amount (in meclizine) of from 6.25 mg to 300 mg; promethazine hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant, in an amount of from 25 mg to 300 mg, in admixture with a pharmaceutical carrier or vehicle.

A further advantageous kit according to this third embodiment provides a kit comprising:

(a/c) a fixed-dose combination that is a pharmaceutical composition comprising or consisting essentially of
  (a) a MCRA selected from the group consisting of xanomeline and pharmaceutically acceptable salts and solvates thereof, and
  (c) a nsPAChA selected from the group consisting of oxybutynin and pharmaceutically acceptable salts and solvates thereof,
in admixture with a pharmaceutical carrier or vehicle in a TTS; and
(b) a pharmaceutical composition in dosage unit form comprising or consisting essentially of a naAEA selected from the group consisting of alosetron and pharmaceutically acceptable salts and solvates thereof, especially its hydrochloride; azasetron and pharmaceutically acceptable salts and solvates thereof, especially its hydrochloride; ondansetron and pharmaceutically acceptable salts and solvates thereof, especially its monohydrochloridedihydrate; granisetron and pharmaceutically acceptable salts and solvates thereof, especially its hydrochloride; dolasetron and pharmaceutically acceptable salts and solvates thereof, especially its monomethanesulfonate monohydrate, ramosetron and pharmaceutically acceptable salts and solvates thereof, especially its hydrochloride; tropisetron and pharmaceutically acceptable salts and solvates thereof, especially its hydrochloride; palonosetron and pharmaceutically acceptable salts and solvates thereof, especially its hydrochloride; domperidone and pharmaceutically acceptable salts and solvates thereof, especially its maleate; metoclopramide and pharmaceutically acceptable salts and solvates thereof, especially its hydrochloride monohydrate; bromopride and pharmaceutically acceptable salts and solvates thereof, especially its monohydrochloride or the dihydrochloride monohydrate; alizapride and pharmaceutically acceptable salts and solvates thereof, especially its hydrochloride; clebopride and pharmaceutically acceptable salts and solvates thereof, especially its malate and the hydrochloride monohydrate; meclizine (meclozine) and pharmaceutically acceptable salts and solvates thereof, especially its hydrochloride monohydrate; promethazine and pharmaceutically acceptable salts and solvates thereof, especially its hydrochloride; chlorpromazine and pharmaceutically acceptable salts and solvates thereof, especially its hydrochloride; prochlorperazine and pharmaceutically acceptable salts and solvates thereof, especially its dimaleate, its dimesylate and its the 1,2-ethanedisulfonate (1:1) (edisilate); hydroxyzine and pharmaceutically acceptable salts and solvates thereof such as the dihydrochloride or the 4-[(3-Carboxy-2-hydroxynaphthalen-1-yl)methyl]-3-hydroxynaphthalene-2-carboxylate (pamoate); dronabinol; nabilone; aprepitant; netupitant; olapitant; and casopitant; in admixture with a pharmaceutical carrier or vehicle.

A particularly advantageous kit according to this third embodiment provides a kit comprising:

(a/c) a fixed-dose combination that is a pharmaceutical composition comprising or consisting essentially of
  (a) a MCRA selected from the group consisting of xanomeline and pharmaceutically acceptable salts and solvates thereof, and
  (c) a nsPAChA selected from the group consisting of oxybutynin and pharmaceutically acceptable salts and solvates thereof, in admixture with a pharmaceutical carrier or vehicle in an oxybutynin and xanomeline TTS, preferably a transdermal patch, wherein said oxybutynin is released in an amount of from 3.9 mg/24 h to 5.85 mg/24 h; and said xanomeline is released in an amount/24 h giving xanomeline plasma concentrations in human of from 16.572 ng/ml to 78.6 ng/ml; and (b) a pharmaceutical composition in dosage unit form comprising or essentially consisting of a naAEA selected from the group consisting of alosetron hydrochloride, in an amount (in alosetron) of from 0.25 mg to 6 mg; azasetron hydrochloride, in an amount (in azasetron) of from 5 mg to 60 mg; dolasetron mesylate, in an amount (in dolasetron) of from 25 mg to 600 mg; granisetron hydrochloride, in an amount (in granisetron) of from 0.5 mg to 6 mg; ondansetron hydrochloride dihydrate, in an amount (in ondansetron) of from 2 mg to 64 mg; palonosetron hydrochloride, in an amount (in palonosetron) of from 0.25 mg to 3 mg; ramosetron hydrochloride, in an amount (in ramosetron) of from 0.0125 mg to 0.3 mg, tropisetron hydrochloride, in an amount (in tropisetron) of from 2.5 mg to 30 mg; domperidone and pharmaceutically acceptable salts and solvates thereof, in an amount (in domperidone) of from 5 mg to 60 mg; haloperidol, in an amount of from 0.5 mg to 60 mg; chlorpromazine hydrochloride, in an amount (in chlorpromazine) of from 12.5 mg to 600 mg; prochlorperazine dimaleate, in an amount (in prochlorperazine) of from 2.5 mg to 30 mg; metoclopramide monohydrochloride monohydrate, in an amount (in metoclopramide) of from 5 mg to 60 mg; bromopride monohydrochloride or dihydrochloride monohydrate, in an amount (in bromopride) of from 5 mg to 60 mg; clebopride hydrogen malate or hydrochloride monohydrate, in an amount (in clebopride) of from 0.25 mg to 3 mg; levosulpiride, in an amount of from 12.5 mg to 600 mg; alizapride hydrochloride, in an amount (in alizapride) of from 25 mg to 300 mg; trimethobenzamide monohydrochloride, in an amount (in trimethobenzamide) of from 50 mg to 600 mg; meclizine (also called meclozine) and pharmaceutically acceptable salts and solvates thereof, in an amount (in meclizine) of from 6.25 mg to 300 mg; promethazine hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant, in an amount of from 25 mg to 300 mg, in admixture with a pharmaceutical carrier or vehicle.

Component (a/c) of kits of this third embodiment, may be a pharmaceutical composition in dosage unit form comprising or consisting essentially of, as active ingredient, a combination of a MCRA and of a nsPAChA at specific doses.

According to a particular aspect, the present invention provides a pharmaceutical composition in dosage unit form comprising or consisting essentially of
(i) a MCRA; and
(ii) a nsPAChA selected from the group consisting of glycopyrronium pharmaceutically acceptable salts, in an amount that is equivalent to from 0.5 mg to 16 mg of glycopyrronium bromide; propiverine and pharmaceutically acceptable salts thereof, in an amount that is equivalent to from 7.5 mg to 240 mg of propiverine hydrobromide; solifenacin and pharmaceutically acceptable salts thereof, in an amount that is equivalent to from 5 mg to 60 mg, preferably from 5 mg to 40 mg, of solifenacin succinate; trospium pharmaceutically acceptable salts, in an amount that is equivalent to from 20 mg to 480 mg of trospium chloride; and TTS-oxybutynin, in a released amount of from 3.9 mg/24 h to 7.8 mg/24 h,
in admixture with a pharmaceutical carrier or vehicle.

According to a specific embodiment of this particular aspect, the present invention provides a pharmaceutical composition in dosage unit form according to the present invention comprises or consists essentially of
(i) a MCRA; and
(ii) a nsPAChA selected from the group consisting of
  anisotropine methylbromide, in an amount of from 120 mg to 400 mg;
  butylscopolamine bromide, in an amount of from 12 mg to 40 mg;
  cimetropium bromide, in an amount of from 55 mg to 200 mg;
  clidinium bromide, in an amount of from 3 mg to 10 mg;
  fesoterodine fumarate, in an amount of from 9.6 mg to 32 mg;
  glycopyrronium bromide, in an amount of from 2.4 mg to 8 mg;
  otilonium bromide, in an amount of from 48 mg to 160 mg;
  oxyphencyclimine, in an amount of from 18 mg to 60 mg;
  prifinium bromide, in an amount of from 36 mg to 120 mg;
  propiverine hydrochloride, in an amount of from 18 mg to 120 mg;
  solifenacin succinate, in an amount selected from the group consisting of from 5 mg to 60 mg, from 10 mg to 40 mg, from 12 mg to 30 mg, from 12 mg to 25 mg, and 21 mg;
  tolterodine hydrogen tartrate, in an amount of from 4.8 mg to 16 mg;

timepidium bromide, in an amount of from 36 mg to 120 mg;

trospium chloride, in an amount of from 24 mg to 240 mg;

valethamate bromide, in an amount of from 12 mg to 40 mg;

in admixture with a pharmaceutical carrier or vehicle.

Preferably, according to the above particular aspect and its specific embodiment, the above component (i) of the pharmaceutical composition in dosage unit form comprises or consists essentially of a MCRA selected from the group consisting of cevimeline hydrochloride hemihydrate, in an amount of from 34.5 mg to 180 mg, xanomeline, as free base, as oxalate or as L-tartrate, in an amount of from 90 mg to 450 mg, milameline hydrochloride, in an amount of from 2.4 mg to 12 mg and MK 7622, as free base, as hydrochloride, as fumarate or as methanesulfonate, in an amount selected from the group consisting of from more than 5 mg to 15 mg, from more than 15 mg to 45 mg, from more than 45 mg to 270 mg, from more than 15 mg to 225 mg, from more than 45 mg to 225 mg, and from 54 mg to 180 mg.

Moreover, according to this third embodiment the present invention provides a pharmaceutical composition in dosage unit form comprising or consisting essentially of (a) a MCRA selected from the group consisting of xanomeline and pharmaceutically acceptable salts and solvates thereof, and (c) a nsPAChA selected from the group consisting of oxybutynin and pharmaceutically acceptable salts and solvates thereof, in admixture with a pharmaceutical carrier or vehicle in a patch from which said oxybutynin is released in an amount of from 3.9 mg/24 h to 5.85 mg/24 h; and said xanomeline is released in an amount/24 h giving xanomeline plasma concentrations in human of from 16.572 ng/ml to 78.6 ng/ml.

According to a fourth embodiment, the invention provides a kit comprising (a/b) a novel fixed-dose combination that is a pharmaceutical composition in dosage unit form comprising or consisting essentially of
  (a) a MCRA; and
  (b) a naAEA in admixture with a pharmaceutical carrier or vehicle; and (c) a pharmaceutical composition in dosage unit form comprising or consisting essentially of a nsPAChA in admixture with a pharmaceutical carrier.

An advantageous kit according to this fourth embodiment provides a kit comprising:

(a/b) a fixed-dose combination that is a pharmaceutical composition comprising or consisting essentially of
  (a) a MCRA selected from the group consisting of 1-methylpiperidine-4-spiro-5'(2'-ethyl-1',4'-thiazoline-3'-one) (AF267) and pharmaceutically acceptable salts and solvates thereof; cis-2'-methylspiro{1-azabicyclo[2.2.2]octane-3,5'-[1,3]oxathiolane}(cevimeline) and pharmaceutically acceptable salts and solvates thereof; 3-[3-(3-(3-fluorophenyl)-2-propyn-1-ylthio)-1,2,5-thiadiazol-4-yl]-1,2,5,6-tetrahydro-1-methylpyridine and pharmaceutically acceptable salts and solvates thereof; (E)-N-methoxy-1-(1-methyl-1,2,5,6-tetrahydropyridin-3-yl)methanimine (milameline) and pharmaceutically acceptable salts and solvates thereof; 2-ethyl-8-methyl-2,8-diazaspiro[4.5]decane-1,3-dione (RS-86) and pharmaceutically acceptable salts and solvates thereof; (3R)—N-methoxyquinuclidine-3-carboximidoyl cyanide (sabcomeline) and pharmaceutically acceptable salts and solvates thereof; (3R)-3-(prop-2-yn-1-yloxy)-1-azabicyclo[2.2.2]octane (talsaclidine) and pharmaceutically acceptable salts and solvates thereof; 5-[4-(hexylsulfanyl)-1,2,5-thiadiazol-3-yl]-1-methyl-1,2,3,6-tetrahydropyridine and pharmaceutically acceptable salts and solvates thereof; 3-(4-hexyloxy-1,2,5-thiadiazol-3-yl)-1-methyl-5,6-dihydro-2H-pyridine (xanomeline), and pharmaceutically acceptable salts and solvates thereof; 5-(3-ethyl-1,2,4-oxadiazol-5-yl)-1,4,5,6-tetrahydropyrimidine (MCD-386) and pharmaceutically acceptable salts and solvates thereof; 3-Methyl-5-(piperidin-3-yl)-1,2,4-oxadiazole, its enantiomers and pharmaceutically acceptable salts and solvates thereof; 3-[(1S,2S)-2-hydroxycyclohexyl]-6-[(6-methylpyridin-3-yl)methyl]benzo[h]quinazolin-4(3H)-one (MK-7622) and pharmaceutically acceptable salts and solvates thereof, and (b) a naAEA selected from the group consisting of alosetron and pharmaceutically acceptable salts and solvates thereof, especially its hydrochloride; azasetron and pharmaceutically acceptable salts and solvates thereof, especially its hydrochloride; ondansetron and pharmaceutically acceptable salts and solvates thereof, especially its monohydrochloride dihydrate; granisetron and pharmaceutically acceptable salts and solvates thereof, especially its hydrochloride; dolasetron and pharmaceutically acceptable salts and solvates thereof, especially its monomethanesulfonate monohydrate, ramosetron and pharmaceutically acceptable salts and solvates thereof, especially its hydrochloride; tropisetron and pharmaceutically acceptable salts and solvates thereof, especially its hydrochloride; palonosetron and pharmaceutically acceptable salts and solvates thereof, especially its hydrochloride; domperidone and pharmaceutically acceptable salts and solvates thereof, especially its maleate; metoclopramide and pharmaceutically acceptable salts and solvates thereof, especially its hydrochloride monohydrate; bromopride and pharmaceutically acceptable salts and solvates thereof, especially its monohydrochloride or the dihydrochloride monohydrate; alizapride and pharmaceutically acceptable salts and solvates thereof, especially its hydrochloride; clebopride and pharmaceutically acceptable salts and solvates thereof, especially its malate and the hydrochloride monohydrate; meclizine (meclozine) and pharmaceutically acceptable salts and solvates thereof, especially its hydrochloride monohydrate; promethazine and pharmaceutically acceptable salts and solvates thereof, especially its hydrochloride; chlorpromazine and pharmaceutically acceptable salts and solvates thereof, especially its hydrochloride; prochlorperazine and pharmaceutically acceptable salts and solvates thereof, especially its dimaleate, its dimesylate and its the 1,2-ethanedisulfonate (1:1) (edisilate); hydroxyzine and pharmaceutically acceptable salts and solvates thereof such as the dihydrochloride or the 4-[(3-carboxy-2-hydroxynaphthalen-1-yl)methyl]-3-hydroxynaphthalene-2-carboxylate (pamoate) dronabinol; nabilone; aprepitant, netupitant, rolapitant; and casopitant in admixture with a pharmaceutical carrier or vehicle; and (c) a pharmaceutical composition in dosage unit form comprising or consisting essentially of a nsPAChA selected from the group consisting of anisotropine pharmaceutically acceptable quaternary salts, butylscopolamine pharmaceutically acceptable salts, cimetropium pharmaceutically acceptable salts, clidinium pharmaceutically acceptable salts, fesoterodine and pharmaceutically acceptable salts thereof, glycopyrronium pharmaceutically acceptable salts, otilonium pharmaceutically acceptable salts, oxyphencyclimine and pharmaceutically acceptable salts thereof, prifinium pharmaceutically acceptable salts, propiverine and pharmaceutically acceptable salts thereof, solifenacin and pharmaceutically acceptable salts thereof, tolterodine and pharmaceutically acceptable salts thereof, timepidium pharmaceutically acceptable salts, trospium pharmaceutically acceptable salts and valethamate pharmaceutically acceptable salts, in admixture with a pharmaceutical carrier or vehicle.

Another advantageous kit according to this fourth embodiment provides a kit comprising:
(a/b) a fixed-dose combination that is a pharmaceutical composition comprising or consisting essentially of
  (a) a MCRA selected from the group consisting of cevimeline hydrochloride hemihydrate, in an amount of from 34.5 mg to 180 mg, xanomeline, as free base, as oxalate or as L-tartrate, in an amount of from 90 mg to 450 mg, milameline hydrochloride, in an amount of from 2.4 mg to 12 mg and MK 7622, as free base, as hydrochloride, as fumarate or as methanesulfonate, in an amount selected from the group consisting of from more than 5 mg to 15 mg, from more than 15 mg to 45 mg, from more than 45 mg to 270 mg, from more than 15 mg to 225 mg, from more than 45 mg to 225 mg, and from 54 mg to 180 mg; and
  (b) a naAEA selected from the group consisting of alosetron hydrochloride, in an amount (in alosetron) of from 0.25 mg to 6 mg; azasetron hydrochloride, in an amount (in azasetron) of from 5 mg to 60 mg; dolasetron mesylate, in an amount (in dolasetron) of from 25 mg to 600 mg; granisetron hydrochloride, in an amount (in granisetron) of from 0.5 mg to 6 mg; ondansetron hydrochloride dihydrate, in an amount (in ondansetron) of from 2 mg to 64 mg; palonosetron hydrochloride, in an amount (in palonosetron) of from 0.25 mg to 3 mg; ramosetron hydrochloride, in an amount (in ramosetron) of from 0.0125 mg to 0.3 mg, tropisetron hydrochloride, in an amount (in tropisetron) of from 2.5 mg to 30 mg; domperidone and pharmaceutically acceptable salts and solvates thereof, in an amount (in domperidone) of from 5 mg to 60 mg; haloperidol, in an amount of from 0.5 mg to 60 mg; chlorpromazine hydrochloride, in an amount (in chlorpromazine) of from 12.5 mg to 600 mg; prochlorperazine dimaleate, in an amount (in prochlorperazine) of from 2.5 mg to 30 mg; metoclopramide monohydrochloride monohydrate, in an amount (in metoclopramide) of from 5 mg to 60 mg; bromopride monohydrochloride or dihydrochloride monohydrate, in an amount (in bromopride) of from 5 mg to 60 mg; clebopride hydrogen malate or hydrochloride monohydrate, in an amount (in clebopride) of from 0.25 mg to 3 mg; levosulpiride, in an amount of from 12.5 mg to 600 mg; alizapride hydrochloride, in an amount (in alizapride) of from 25 mg to 300 mg; trimethobenzamide monohydrochloride, in an amount (in trimethobenzamide) of from 50 mg to 600 mg; meclizine (also called meclozine) and pharmaceutically acceptable salts and solvates thereof, in an amount (in meclizine) of from 6.25 mg to 300 mg; promethazine hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant, in an amount of from 25 mg to 300 mg,
in admixture with a pharmaceutical carrier or vehicle; and
(c) a pharmaceutical composition in dosage unit form comprising or consisting essentially of a nsPAChA selected from the group consisting of glycopyrronium pharmaceutically acceptable salts, in an amount that is equivalent to from 0.5 mg to 16 mg of glycopyrronium bromide; propiverine and pharmaceutically acceptable salts thereof, in an amount that is equivalent to from 7.5 mg to 240 mg of propiverine hydrobromide; solifenacin and pharmaceutically acceptable salts thereof, in an amount that is equivalent to from 5 mg to 60 mg, preferably from 5 mg to 40 mg, of solifenacin succinate; trospium pharmaceutically acceptable salts, in an amount that is equivalent to from 20 mg to 480 mg of trospium chloride; and TTS-oxybutynin, in a released amount of from 3.9 mg/24 h to 7.8 mg/24 h, in admixture with a pharmaceutical carrier or vehicle.

A specific kit according to this fourth embodiment provides a kit comprising:
(a/b) a fixed-dose combination that is a pharmaceutical composition comprising or consisting essentially of
  (a) a MCRA selected from the group consisting of cevimeline hydrochloride hemihydrate, in an amount of from 34.5 mg to 180 mg, xanomeline, as free base, as oxalate or as L-tartrate, in an amount of from 90 mg to 450 mg, milameline hydrochloride, in an amount of from 2.4 mg to 12 mg and MK 7622, as free base, as hydrochloride, as fumarate or as methanesulfonate, in an amount selected from the group consisting of from more than 5 mg to 15 mg, from more than 15 mg to 45 mg, from more than 45 mg to 270 mg, from more than 15 mg to 225 mg, from more than 45 mg to 225 mg, and from 54 mg to 180 mg; and
  (b) a naAEA selected from the group consisting of alosetron hydrochloride, in an amount (in alosetron) of from 0.25 mg to 6 mg; azasetron hydrochloride, in an amount (in azasetron) of from 5 mg to 60 mg; dolasetron mesylate, in an amount (in dolasetron) of from 25 mg to 600 mg; granisetron hydrochloride, in an amount (in granisetron) of from 0.5 mg to 6 mg; ondansetron hydrochloride dihydrate, in an amount (in ondansetron) of from 2 mg to 64 mg; palonosetron hydrochloride, in an amount (in palonosetron) of from 0.25 mg to 3 mg; ramosetron hydrochloride, in an amount (in ramosetron) of from 0.0125 mg to 0.3 mg, tropisetron hydrochloride, in an amount (in tropisetron) of from 2.5 mg to 30 mg; domperidone and pharmaceutically acceptable salts and solvates thereof, in an amount (in domperidone) of from 5 mg to 60 mg; haloperidol, in an amount of from 0.5 mg to 60 mg; chlorpromazine hydrochloride, in an amount (in chlorpromazine) of from 12.5 mg to 600 mg; prochlorperazine dimaleate, in an amount (in prochlorperazine) of from 2.5 mg to 30 mg; metoclopramide monohydrochloride monohydrate, in an amount (in metoclopramide) of from 5 mg to 60 mg; bromopride monohydrochloride or dihydrochloride monohydrate, in an amount (in bromopride) of from 5 mg to 60 mg; clebopride hydrogen malate or hydrochloride monohydrate, in an amount (in clebopride) of from 0.25 mg to 3 mg; levosulpiride, in an amount of from 12.5 mg to 600 mg; alizapride hydrochloride, in an amount (in alizapride) of from 25 mg to 300 mg; trimethobenzamide monohydrochloride, in an amount (in trimethobenzamide) of from 50 mg to 600 mg; meclizine (also called meclozine) and pharmaceutically acceptable salts and solvates thereof, in an amount (in meclizine) of from 6.25 mg to 300 mg; promethazine hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant, in an amount of from 25 mg to 300 mg, in admixture with a pharmaceutical carrier or vehicle; and (c) a pharmaceutical composition in dosage unit form comprising or consisting essentially of a nsPAChA selected from the group consisting of anisotropine methylbromide in an amount of from 25 mg to 400 mg, normally from 25 mg to 300 mg; butylscopolamine bromide, in an amount of from 5 mg to 60 mg, normally from 12 mg to 40 mg; cimetropium bromide, in an amount of from 25 mg to 200 mg, normally from 55 mg to 200 mg; clidinium bromide, in an amount of from 1.25 mg to 15 mg, normally from 3 mg to 10 mg; fesoterodine fumarate, in an amount of from 4 mg to 48 mg, normally from 9.6 mg to 32 mg; glycopyrronium bromide, in an amount of from 1 mg to 12 mg, normally from 2.4 mg to 8 mg; otilonium bromide, in an amount of from 20 mg to 240 mg, normally from 48 mg to 160 mg; oxyphencyclimine, in an amount of from 10 mg to 60 mg. normally from 18 mg to 60 mg; prifinium bromide, in an amount of from 15 mg to 180 mg, normally from 36 mg to 120 mg; propiverine hydrochloride, in an amount of from 7.5 to 180 mg, normally from 18 mg to 90 mg; solifenacin succinate, in an amount selected from the group consisting of from 5 mg to 60 mg, from 10 mg to 40 mg, from 12 mg to 30 mg, from 12 mg to 25 mg, and 21 mg; tolterodine tartrate, in an amount of from 1 mg to 16 mg, normally from 4.8 mg to 16 mg; timepidium bromide, in an amount of from 7.5 mg to 180 mg, normally from 36 mg to 120 mg; trospium chloride, in an amount of from 24 mg to 480 mg, normally from 24 mg to 240 mg; TTS-oxybutynin, as a patch releasing from 3.9 mg/24 to 7.8 mg/24 h, advantageously from 3.9 mg/24 h to 5.85 mg/24 h, normally 3.9 mg/24 h oxybutynin; and valethamate bromide, in an amount of from 5 mg to 60 mg, normally from 12 mg to 40 mg, in admixture with a pharmaceutical carrier, in admixture with a pharmaceutical carrier or vehicle.

For example, in instances in which each of the drugs themselves are administered as individual or separate dosage forms (e.g., capsules or tablets), the kit of the present invention comprises each of the drugs making up the composition of the invention, along with instructions for use. Alternatively, each of the drug components of the combination may be combined into a single administrable dosage form such as a capsule.

Said kit may include one or more tablets, hard or soft capsules containing the Component (a) and Component (b), in the dosage amounts within the ranges described above.

Component (a/b) of the kits of this fourth embodiment, consisting of pharmaceutical composition in dosage unit form comprising, as active ingredient, a combination with a MCRA and of a naAEA is novel and a further object of the present invention.

Thus, the present invention further provides a pharmaceutical composition in dosage unit form comprising or consisting essentially of (a) a MCRA; and
(b) a naAEA, in admixture with a pharmaceutical carrier or vehicle.

The characteristics, the doses and the use of this pharmaceutical composition are exhaustively illustrated hereinabove.

An advantageous MCRA/naAEA composition in dosage unit form comprises or essentially consists of (a) a MCRA selected from the group consisting of AF267 and pharmaceutically acceptable salts and solvates thereof; cevimeline and pharmaceutically acceptable salts and solvates thereof; 3-[3-(3-(3-fluorophenyl)-2-propyn-1-ylthio)-1,2,5-thiadiazol-4-yl]-1,2,5,6-tetrahydro-1-methylpyridine and pharmaceutically acceptable salts and solvates thereof; milameline and pharmaceutically acceptable salts and solvates thereof; RS-86 and pharmaceutically acceptable salts and solvates thereof; sabcomeline and pharmaceutically acceptable salts and solvates thereof; talsaclidine and pharmaceutically acceptable salts and solvates thereof; 5-[4-(hexylsulfanyl)-1,2,5-thiadiazol-3-yl]-1-methyl-1,2,3,6-tetrahydropyridine and pharmaceutically acceptable salts and solvates thereof; xanomeline and pharmaceutically acceptable salts and solvates thereof; MCD-386 and pharmaceutically acceptable salts and solvates thereof; 3-Methyl-5-(piperidin-3-yl)-1,2,4-oxadiazole, its enantiomers and pharmaceutically acceptable salts and solvates thereof; MK-7622 and pharmaceutically acceptable salts and solvates thereof; and (b) a naAEA selected from the group consisting of (b1) 5HT3-antagonists, (b2) DA-antagonists, (b3) H1-antagonists, (b4) cannabinoids, and (b5) NK1-antagonists, in admixture with a pharmaceutical carrier or vehicle.

A particularly advantageous MCRA/naAEA composition in dosage unit form comprises or essentially consists of (a) a MCRA selected from the group consisting of cevimeline hydrochloride hemihydrate, in an amount of from 34.5 mg to 180 mg, xanomeline, as free base, as oxalate or as L-tartrate, in an amount of from 90 mg to 450 mg, milameline hydrochloride, in an amount of from 2.4 mg to 12 mg and MK 7622, as free base, as hydrochloride, as fumarate or as methanesulfonate, in an amount selected from the group consisting of from more than 5 mg to 15 mg, from more than 15 mg to 45 mg, from more than 45 mg to 270 mg, from more than 15 mg to 225 mg, from more than 45 mg to 225 mg, and from 54 mg to 180 mg; and (b) a naAEA selected from the group consisting of alosetron hydrochloride, in an amount (in alosetron) of from 0.25 mg to 6 mg; azasetron hydrochloride, in an amount (in azasetron) of from 5 mg to 60 mg; dolasetron mesylate, in an amount (in dolasetron) of from 25 mg to 600 mg; granisetron hydrochloride, in an amount (in granisetron) of from 0.5 mg to 6 mg; ondansetron hydrochloride dihydrate, in an amount (in ondansetron) of from 2 mg to 64 mg; palonosetron hydrochloride, in an amount (in palonosetron) of from 0.25 mg to 3 mg; ramosetron hydrochloride, in an amount (in ramosetron) of from 0.0125 mg to 0.3 mg, tropisetron hydrochloride, in an amount (in tropisetron) of from 2.5 mg to 30 mg; domperidone and pharmaceutically acceptable salts and solvates thereof, in an amount (in domperidone) of from 5 mg to 60 mg; haloperidol, in an amount of from 0.5 mg to 60 mg; chlorpromazine hydrochloride, in an amount (in chlorpromazine) of from 12.5 mg to 600 mg; prochlorperazine dimaleate, in an amount (in prochlorperazine) of from 2.5 mg to 30 mg; metoclopramide monohydrochloride monohydrate, in an amount (in metoclopramide) of from 5 mg to 60 mg; bromopride monohydrochloride or dihydrochloride monohydrate, in an amount (in bromopride) of from 5 mg to 60 mg; clebopride hydrogen malate or hydrochloride monohydrate, in an amount (in clebopride) of from 0.25 mg to 3 mg; levosulpiride, in an amount of from 12.5 mg to 600 mg; alizapride hydrochloride, in an amount (in alizapride) of from 25 mg to 300 mg; trimethobenzamide monohydrochloride, in an amount (in trimethobenzamide) of from 50 mg to 600 mg; meclizine (also called meclozine) and pharmaceutically acceptable salts and solvates thereof, in an amount (in meclizine) of from 6.25 mg to 300 mg; promethazine hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant, in an amount of from 25 mg to 300 mg, in admixture with a pharmaceutical carrier or vehicle.

In the kits of the present invention, and in the compositions contained therein, solifenacin succinate, when present as Component (c), preferably is in an amount selected from the group consisting of from 5 mg to 60 mg, from 10 mg to 40 mg, from 12 mg to 30 mg, from 12 mg to 25 mg, and 21 mg.

According to a fifth embodiment, each of the above kits may comprise, as a further component of the combinations contained therein, Component (d), an AChEI also formulated in a pharmaceutical composition, said AChEI being selected from the group consisting of 1,2,3,4-tetrahydro-9-acridinamine (tacrine) and pharmaceutically acceptable salts and solvates thereof, (±)-2,3-dihydro-5,6-dimethoxy-2-[[1-(phenylmethyl)-4-piperidinyl]methyl]-1H-inden-1-one (donepezil) and pharmaceutically acceptable salt and solvates thereof, (S)—N-Ethyl-N-methyl-3-[1-(dimethylamino)ethyl]-phenyl carbamate (rivastigmine) and pharmaceutically acceptable salts and solvates thereof, 4aS,6R,8aS-3-methoxy-11-methyl-4a,5,9,10,11,12-hexahydroxy-6H-benzofuro[3a,3,2-e,f]benzazepin-6-ol (galantamine) and pharmaceutically acceptable salts and solvates thereof.

Among the above preferred AChEIs, in the kits of the present invention, as Component (d), donepezil hydrochloride is generally present at a dose of from 5 mg to 98 mg, advantageously from 15 mg to 69 mg, normally from 15 mg to 60 mg; rivastigmine, as hydrogen tartrate, is present, in a composition for oral administration, at a dose in rivastigmine, of from 1.5 mg to 30 mg, advantageously from 6 mg to 24 mg, normally from 9 mg to 18 mg; rivastigmine, as the free base, is present in patch releasing from 4.6 mg/24 h to 52 mg/24 h, advantageously from 9.6 mg/24 h to 39.9 mg/24 h, normally from 13.3 mg/24 h to 39.9 mg/24 h rivastigmine; and galantamine, as hydrobromide, is present in an amount of from 4 mg to 96 mg, advantageously from 12 mg to 96 mg, normally from 18 mg to 48 mg.

Thus, according to one aspect of this fifth embodiment, the present invention also provides a kit comprising or essentially consisting of (a) a pharmaceutical composition in dosage unit form essentially consisting of a MCRA, in admixture with a pharmaceutical carrier or vehicle; and (b) a pharmaceutical composition in dosage unit form essentially consisting of a naAEA, in admixture with a pharmaceutical carrier or vehicle; and (c) a pharmaceutical composition in dosage unit form essentially consisting of a nsPAChA, in admixture with a pharmaceutical carrier or vehicle; and (d) a pharmaceutical composition dosage unit form essentially consisting of an AChEI selected from the group consisting of donepezil hydrochloride in an amount of from 5 mg to 98 mg, advantageously from 15 mg to 69 mg, normally from 15 mg to 60 mg; rivastigmine, as hydrogen tartrate, in an amount, in rivastigmine, of from 1.5 mg to 30 mg, advantageously from 6 mg to 24 mg, normally from 9 mg to 18 mg; rivastigmine, as the free base, in patch releasing from 4.6 mg/24 h to 52 mg/24 h, advantageously from 9.6 mg/24 h to 39.9 mg/24 h, normally from 13.3 mg/24 h to 39.9 mg/24 h rivastigmine; and galantamine, as hydrobromide, in an amount (in galantamine, of from 4 mg to 96 mg, advantageously from 12 mg to 96 mg, normally from 18 mg to 48 mg, in admixture with a pharmaceutical carrier or vehicle.

According to this first aspect, in the above combination in the kit, the AChEI Component (d) may be combined with any MCRA Component (a) and with any naAEA Component (b) and with any nsPAChA Component (c) illustrated in this section, in a quadruple combination useful as a cocktail for combating hypocholinergic disorders of the CNS as herein above defined.

A second aspect of this fifth embodiment provides a kit comprising:

(a/b) a fixed-dose combination that is a pharmaceutical composition comprising or consisting essentially of (a) a MCRA selected from the group consisting of cevimeline hydrochloride hemihydrate, in an amount of from 34.5 mg to 180 mg, xanomeline, as free base, as oxalate or as L-tartrate, in an amount of from 90 mg to 450 mg, milameline hydrochloride, in an amount of from 2.4 mg to 12 mg and MK 7622, as free base, as hydrochloride, as fumarate or as methanesulfonate, in an amount selected from the group consisting of from more than 5 mg to 15 mg, from more than 15 mg to 45 mg, from more than 45 mg to 270 mg, from more than 15 mg to 225 mg, from more than 45 mg to 225 mg, and from 54 mg to 180 mg; and (b) a nAEA selected from the group consisting of alosetron and pharmaceutically acceptable salts and solvates thereof, in particular the hydrochloride, in an amount (in alosetron) of from 0.25 mg to 6 mg; azasetron and pharmaceutically acceptable salts and solvates thereof, in particular the hydrochloride, in an amount (in azasetron) of from 5 mg to 60 mg; dolasetron and pharmaceutically acceptable salts and solvates thereof, in particular the mesylate, in an amount (in dolasetron) of from 25 mg to 600 mg; granisetron and pharmaceutically acceptable salts and solvates thereof, in particular the hydrochloride, in an amount (in granisetron) of from 0.5 mg to 6 mg; ondansetron and pharmaceutically acceptable salts and solvates thereof, in particular the hydrochloride dihydrate, in an amount (in ondansetron) of from 2 mg to 64 mg; palonosetron and pharmaceutically acceptable salts and solvated thereof, in particular its hydrochloride, in an amount (in palonosetron) of from 0.25 mg to 3 mg; ramosetron and pharmaceutically acceptable salts and solvates thereof, in particular its hydrochloride, in an amount (in ramosetron) of from 0.0125 mg to 0.3 mg; tropisetron and pharmaceutically acceptable salts and solvates thereof, in particular the hydrochloride, in an amount of from 2.5 mg to 30 mg; domperidone and pharmaceutically acceptable salts and solvates thereof, in an amount (in domperidone) of from 5 mg to 60 mg; haloperidol, in an amount of from 0.5 mg to 60 mg; chlorpromazine and pharmaceutically acceptable salts and solvates thereof, in particular the hydrochloride, in an amount (in chlorpromazine) of from 12.5 mg to 600 mg; prochlorperazine and pharmaceutically acceptable salts and solvates thereof, in particular the dimaleate, in an amount (in prochlorperazine) of from 2.5 mg to 30 mg; metoclopramide and pharmaceutically acceptable salts and solvates thereof, in particular the monohydrochloride monohydrate, in an amount (in metoclopramide) of from 5 mg to 60 mg; bromopride and pharmaceutically acceptable salts and solvates, in particular the monohydrochloride and the dihydrochloride monohydrate, in an amount (in bromopride) of from 5 mg to 60 mg; clebopride and pharmaceutically acceptable salts and solvates thereof, in particular the hydrogen malate and the hydrochloride monohydrate, in an amount (in clebopride) of from 0.25 mg to 3 mg; levosulpiride, in an amount of from 12.5 mg to 600 mg; alizapride and pharmaceutically acceptable salts thereof, in particular the hydrochloride, in an amount (in alizapride) of from 25 mg to 300 mg; trimethobenzamide and pharmaceutically acceptable salts thereof such as the monohydrochloride, in an amount (in trimethobenzamide) of from 50 mg to 600 mg; meclizine (also called meclozine) and pharmaceutically acceptable salts and solvates thereof, in an amount (in meclizine) of from 6.25 mg to 300 mg; promethazine and pharmaceutically acceptable salts and solvates thereof, in particular the hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant, in an amount of from 25 mg to 300 mg, in admixture with a pharmaceutical carrier or vehicle; and (c) a pharmaceutical composition in dosage unit form essentially consisting of a nsPAChA selected from the group consisting of glycopyrronium pharmaceutically acceptable salts, in an amount that is equivalent to from 0.5 mg to 16 mg of glycopyrronium bromide; propiverine and pharmaceutically acceptable salts thereof, in an amount that is equivalent to from 7.5 mg to 240 mg of propiverine hydrobromide; solifenacin and pharmaceutically acceptable salts thereof, in an amount that is equivalent to from 5 mg to 60 mg, preferably from 5 mg to 40 mg, of solifenacin succinate; trospium pharmaceutically acceptable salts, in an amount that is equivalent to from 20 mg to 480 mg of trospium chloride; and TTS-oxybutynin, in a released amount of from 3.9 mg/24 h to 7.8 mg/24 h, in admixture with a pharmaceutical carrier or vehicle; and (d) a pharmaceutical composition comprising an AChEI selected from the group consisting of donepezil hydrochloride, in an amount of from 5 mg to 98 mg, advantageously from 15 mg to 69 mg, normally from 15 mg to 60 mg; rivastigmine, as hydrogen tartrate, is present, in an amount, in rivastigmine, of from 1.5 mg to 30 mg, advantageously from 6 mg to 24 mg, normally from 9 mg to 18 mg; rivastigmine, as the free base, in patch releasing from 4.6 mg/24 h to 52 mg/24 h, advantageously from 9.6 mg/24 h to 39.9 mg/24 h, normally from 13.3 mg/24 h to 39.9 mg/24 h or from 4.6 mg/24 h to 13.3 mg/24 h rivastigmine; and galantamine, as hydrobromide, in an amount (in galantamine of from 4 mg to 96 mg, advantageously from 12 mg to 96 mg, normally from 18 mg to 48 mg, in admixture with a pharmaceutical carrier or vehicle.

A specific kit according this fifth embodiment comprises (a/b) the above MCRA/naAEA fixed-dose combination in said composition in admixture with a pharmaceutical carrier or vehicle; and (c) a pharmaceutical composition in dosage unit form essentially consisting of a nsPAChA selected from the group consisting of anisotropine methylbromide, in an amount of from 25 mg to 300 mg, normally from 60 mg to 200 mg; butylscopolamine bromide in an amount of from 5 mg to 60 mg, normally from 12 mg to 40 mg; cimetropium bromide, in an amount of from 25 mg to 200 mg; clidinium bromide in an amount of from 1.25 mg to 15 mg, normally from 3 mg to 10 mg; fesoterodine fumarate, in an amount of from 4 mg to 48 mg, normally from 9.6 mg to 32 mg; glycopyrronium bromide in an amount of from 1 mg to 12 mg, normally from 2.2 to 8 mg; otilonium bromide in an amount of from 20 mg to 240 mg, normally from 48 mg to 160 mg; prifinium bromide in an amount of from 15 mg to 180 mg, normally from 36 mg to 120 mg; propiverine hydrochloride, in an amount of from 7.5 mg to 180 mg, normally from 18 mg to 120 mg; solifenacin succinate, in an amount of from 5 mg to 60 mg, normally from 12 mg to 25 mg or 21 mg; tolterodine tartrate, in an amount of from 1 mg to 16 mg, normally from 4.8 mg to 16 mg; timepidium bromide in an amount of from 7.5 mg to 180 mg, normally from 36 mg to 120 mgr; trospium chloride, in an amount of from 24 mg to 480 mg; TTS-oxybutynin, as a patch releasing from 3.9 mg/24 to 7.8 mg/24 h, advantageously from 3.9 mg/24 h to 5.85 mg/24 h, normally 3.9 mg/24 h oxybutynin; and valethamate bromide in an amount of from 5 mg to 60 mg, normally from 12 mg to 40 mg; in admixture with a pharmaceutical carrier or vehicle; and (d) the above pharmaceutical composition comprising said AChEI, in admixture with a pharmaceutical carrier or vehicle.

A kit according to a preferred form of this second aspect of this fifth embodiment essentially consists of a combination of the above Components (a) and (b) with (c) a pharmaceutical composition in dosage unit form comprising or essentially consisting of the nsPAChA TTS-oxybutynin, as a patch releasing from 3.9 mg/24 to 7.8 mg/24 h, advantageously from 3.9 mg/24 h, normally 3.9 mg/24 h oxybutynin, in admixture with a pharmaceutical carrier or vehicle; and (d) a pharmaceutical composition in dosage unit form comprising or essentially consisting of the AChEI rivastigmine in a patch releasing from 4.6 mg/24 h to 39.9/mg24 h, normally from 4.6 mg/24 h to 13.3 mg/24 h rivastigmine, in admixture with a pharmaceutical carrier or vehicle.

A particularly preferred form of this second aspect of this fifth embodiment essentially consists of a combination of the above Component (a/b) fixed-dose combination with a Component (c/d) fixed-dose combination that is a pharmaceutical composition in dosage unit form comprising or consisting essentially of (c/d) a pharmaceutical composition essentially consisting of
(a) a nsPAChA that is oxybutynin base; and (b) an AChEI that is rivastigmine, as the free base, in admixture with a pharmaceutical carrier or vehicle, in a transdermal patch.

Said patch advantageously releases from 3.9 mg/24 h to 7.85 mg/24 h, normally 3.9 mg/24 h oxybutynin; and from 4.6 mg/24 h to 39.9 mg/24 h, normally from 4.6 mg/24 h to 13.3 mg/24 h rivastigmine.

Compositions (a/b) of the kits of the present invention described above, are each novel and a further object of the present invention.

The characteristics, the doses and the use of this pharmaceutical composition are exhaustively illustrated herein above.

According to a third aspect of this fifth embodiment, the invention also provides a kit comprising
(a) a pharmaceutical composition in dosage unit form comprising or consisting essentially of a MCRA in admixture with a pharmaceutical carrier or vehicle; and
(b/c) a fixed-dose combination that is a pharmaceutical composition comprising or consisting essentially of
  (b) a naAEA; and
  (c) a nsPAChA selected from the group consisting of glycopyrronium pharmaceutically acceptable salts, in an amount that is equivalent to from 0.5 mg to 16 mg of glycopyrronium bromide; propiverine and pharmaceutically acceptable salts thereof, in an amount that is equivalent to from 7.5 mg to 240 mg of propiverine hydrobromide; solifenacin and pharmaceutically acceptable salts thereof, in an amount that is equivalent to from 5 mg to 60 mg, preferably from 5 mg to 40 mg, of solifenacin succinate; trospium pharmaceutically acceptable salts, in an amount that is equivalent to from 20 mg to 480 mg of trospium chloride; and TTS-oxybutynin, in a released amount of from 3.9 mg/24 h to 7.8 mg/24 h, in admixture with a pharmaceutical carrier or vehicle; and
(d) a pharmaceutical composition in dosage unit form comprising or consisting essentially of anAChEI, essentially consisting of donepezil hydrochloride, in an amount of from 5 mg to 60 mg, in admixture with a pharmaceutical carrier or vehicle A specific kit according to this third aspect of this fifth embodiment, the invention also provides a kit comprises, as Component (c), a nsPAChA selected from the group consisting of solifenacin succinate, in an amount of from 5 mg to 60 mg, normally from 10 mg to 25 mg or of 21 mg, propiverine hydrochloride, in an amount of from 7.5 mg to 240 mg, normally from 30 mg to 120 mg, glycopyrronium bromide, in an amount of from 1 mg to 12 mg, normally form 2 mg to 8 mg; and trospium chloride, in an amount of from 10 mg to 480 mg, normally from 20 mg to 240 mg.

According to this fifth embodiment, the (b/c) fixed-dose combination is administered to a patient in need of the treatment as a single unit form at the doses illustrated in "The Combinations" section.

This kit has the advantage of allowing an improvement in the treatment of a patient suffering from a hypocholinergic disorder due to synergistic action of the antiemetic/anticholinergic combination.

The Fixed-Dose Combinations

As indicated above, the pharmaceutical compositions prepared by using the nsPAChAs according to the present invention are present in unit forms also containing a $M_2$-antagonist that acts by presynaptically releasing acetylcholine in the CNS to improve the symptoms of Alzheimer type dementia and the other aforementioned hypocholinergic disorders.

Thus, it is another object of the present invention to provide a fixed-dose combination that is a pharmaceutical composition in dosage unit form that is comprising or consisting essentially of, as Components:
(a) a muscarinic cholinergic receptor agonists (MCRA);
(b) a non-anticholinergic antiemetic agent (naAEA); and
(c) a non-selective peripheral anticholinergic agent (nsPAChA),
in admixture with at least one pharmaceutical carrier.

Herein below, the expression "unit form" will also be used to designate a "pharmaceutical composition in dosage unit form".

According to the present invention, a pharmaceutical composition of the present invention may be a composition comprising or consisting essentially of a mixture of a MCRA [Component (a)], a naAEA [Component (b)] and of a nsPAChA [Component (c)] wherein Component (a) is present in a quantity sufficient or effective to maximally alleviate disease-associated neurobehavioral symptoms for the treatment of hypocholinergic disorders, and wherein Component (b) and Component (c), the latter not appreciably penetrating the blood brain barrier, surprisingly act synergistically to attenuate the dose-limiting side effects of the MCRAs, thus enabling a greater increase in the MTD of said MCRAs with attending increase in the therapeutic efficacy of MCRAs. Such a composition allows high doses of MCRA Component (a) to be safely used, that would have otherwise been dangerous in the absence of Components (b) and (c).

The pharmaceutical composition of the present invention improves the treatment of human hypocholinergic disorders of the CNS as described above, such as dementias of the Alzheimer type and schizophrenia.

Any MCRA, any naAEA and any nsPAChA as described herein, and exemplified in the above "The Combinations" section may be formulated in a pharmaceutical composition in a single unit form, in admixture with at least one pharmaceutical carrier according to conventional methods in the art, and as exemplified in the "The Formulations" section below.

In unit form for immediate release or extended release, the $M_2$-antagonist Component (a) is present in an amount of from 0.5 mg to 1500 mg. Normally, the $M_2$-antagonist Component (a) is present, in an IR-form, in an amount of from 0.5 mg to 1000 mg and in an ER-form in an amount of from 1.5 mg to 1500 mg.

Any one of the MCRAs illustrated in the above "The MCRAs" section may be a suitable Component (a), a MCRA selected from the group consisting of AF267 and pharmaceutically acceptable salts and solvates thereof, especially its hydrochloride (AF 267B), cevimeline and pharmaceutically acceptable salts and solvates thereof, 3-[3-(3-(3-fluorophenyl)-2-propyn-1-ylthio)-1,2,5-thiadiazol-4-yl]-1,2,5,6-tetrahydro-1-methylpyridine (EUK 1001) and pharmaceutically acceptable salts and solvates thereof especially its oxalate, milameline and pharmaceutically acceptable salts and solvates thereof especially its hydrochloride, RS-86 and pharmaceutically acceptable salts and solvates thereof, especially its hydrobromide; sabcomeline and pharmaceutically acceptable salts and solvates thereof; talsaclidine and pharmaceutically acceptable salts and solvates thereof, especially its fumarate; tazomeline and pharmaceutically acceptable salts and solvates thereof, especially its hydrochloride; xanomeline and pharmaceutically acceptable salts and solvates thereof, especially its oxalate and its L-tartrate; racemic 3-Methyl-5-(piperidin-3-yl)-1,2,4-oxadiazole and pharmaceutically acceptable salts and solvates thereof, S-(+)-3-methyl-5-(piperidin-3-yl)-1,2,4-oxadiazole D-tartrate; R-(−)-3-Methyl-5-(piperidin-3-yl)-1,2,4-oxadiazole L-tartrate; and MK-7622 and pharmaceutically acceptable salts and solvates thereof, especially its hydrochloride and its fumarate, as illustrated in the above "The MCRAs" section, being advantageous.

According to a preferred embodiment, Component (a) is a MCRA selected from the group consisting of cevimeline and pharmaceutically acceptable salts thereof, milameline and pharmaceutically acceptable salts and solvates thereof, xanomeline and pharmaceutically acceptable salt and solvates thereof; racemic 3-Methyl-5-(piperidin-3-yl)-1,2,4-oxadiazole and pharmaceutically acceptable salts and solvates thereof, S-(+)-3-methyl-5-(piperidin-3-yl)-1,2,4-oxadiazole D-tartrate; R-(−)-3-Methyl-5-(piperidin-3-yl)-1,2,4-oxadiazole L-tartrate; MK-7622 and pharmaceutically acceptable salts and solvates thereof. Cevimeline, its hydrochloride hemihydrate, xanomeline, its oxalate or L-tartrate and MK-7622, its hydrochloride or fumarate or methanesulfonate are the preferred Components (a) of the fixed-dose combination.

According to a particularly preferred embodiment, in the pharmaceutical composition the Component (a) is a MCRA selected from the group consisting of
  cevimeline that is present, as hydrochloride hemihydrate, in an amount of from 30 mg to 120 mg, preferably from 36 mg to 120 mg in an oral IR or, as free base or as hydrochloride hemihydrate, from 36 mg to 180 mg, preferably from 45 mg to 180 mg in an oral or transdermal ER form, in particular in a TTS.
  milameline that is present, as hydrochloride, in an amount of from 2 mg to 8 mg, preferably from 2.4 mg to 8 mg in an oral IR or, as free base or as hydrochloride, from 2.4 mg to 12 mg, preferably from 3 mg to 12 mg in an oral or transdermal ER form, in particular in a TTS; and
  xanomeline that is present, as oxalate or L-tartrate, in an amount of from 75 mg to 300 mg preferably from 90 mg to 300 mg in an oral IR form or, as free base, as oxalate or as L-tartrate, from 90 mg to 450 mg, preferably from 112.5 mg to 450 mg in an oral or transdermal ER form, in particular in a TTS
  MK-7622 that is present, as free base, as hydrochloride or as fumarate, in an amount of from 5 mg to 270 mg, in particular in an amount selected from the group consisting of more than 5 mg to 15 mg, from more than 15 mg to 45 mg, from more than 45 mg to 270 mg, from more than 15 mg to 225 mg, from more than 45 mg to 225 mg, and from 54 mg to 180 mg.

The Component (b) of the fixed-dose combination may be a non-anticholinergic antiemetic agent selected from the group consisting of (b1) 5HT3-antagonists, (b2) DA-antagonists, (b3) H1-antagonists, (b4) cannabinoids, (b5) NK1-antagonists.

In a preferred embodiment, Component (b) of the fixed-dose combination is selected from the group consisting of alosetron and pharmaceutically acceptable salts and solvates thereof, especially its hydrochloride; azasetron and pharmaceutically acceptable salts and solvates thereof, especially its hydrochloride; ondansetron and pharmaceutically acceptable salts and solvates thereof, especially its monohydrochloride dihydrate; granisetron and pharmaceutically acceptable salts and solvates thereof, especially its hydrochloride; dolasetron and pharmaceutically acceptable salts and solvates thereof, especially its monomethanesulfonate monohydrate, ramosetron and pharmaceutically acceptable salts and solvates thereof, especially its hydrochloride; tropisetron and pharmaceutically acceptable salts and solvates thereof, especially its hydrochloride; palonosetron and pharmaceutically acceptable salts and solvates thereof, especially its hydrochloride; domperidone and pharmaceutically acceptable salts and solvates thereof, especially its maleate; metoclopramide and pharmaceutically acceptable salts and solvates thereof, especially its hydrochloride monohydrate; bromopride and pharmaceutically acceptable salts and solvates thereof, especially its monohydrochloride or the dihydrochloride monohydrate; alizapride and pharmaceutically acceptable salts and solvates thereof, especially its hydrochloride; clebopride and pharmaceutically acceptable salts and solvates thereof, especially its malate and the hydrochloride monohydrate; meclizine (meclozine) and pharmaceutically acceptable salts and solvates thereof, especially its hydrochloride monohydrate; promethazine and pharmaceutically acceptable salts and solvates thereof, especially its hydrochloride; chlorpromazine and pharmaceutically acceptable salts and solvates thereof, especially its hydrochloride; prochlorperazine and pharmaceutically acceptable salts and solvates thereof, especially its dimaleate, its dimesylate and its the 1,2-ethanedisulfonate (1:1) (edisilate); hydroxyzine and pharmaceutically acceptable salts and solvates thereof such as the dihydrochloride or the 4-[(3-carboxy-2-hydroxynaphthalen-1-yl)methyl]-3-hydroxynaphthalene-2-carboxylate (pamoate) dronabinol; nabilone; aprepitant; netupitant; rolapitant; and casopitant.

According to a particularly preferred embodiment, in the pharmaceutical composition the Component (b) is a naAEA selected from the group consisting of alosetron and pharmaceutically acceptable salts and solvates thereof, in particular the hydrochloride, in an amount (in alosetron) of from 0.25 mg to 6 mg; azasetron and pharmaceutically acceptable salts and solvates thereof, in particular the hydrochloride, in an amount (in azasetron) of from 5 mg to 60 mg; dolasetron and pharmaceutically acceptable salts and solvates thereof, in particular the mesylate, in an amount (in dolasetron) of from 25 mg to 600 mg; granisetron and pharmaceutically acceptable salts and solvates thereof, in particular the hydrochloride, in an amount (in granisetron) of from 0.5 mg to 6 mg; ondansetron and pharmaceutically acceptable salts and solvates thereof, in particular the hydrochloride dihydrate, in an amount (in ondansetron) of from 2 mg to 64 mg; palonosetron and pharmaceutically acceptable salts and solvated thereof, in particular its hydrochloride, in an amount (in palonosetron) of from 0.25 mg to 3 mg; ramosetron and pharmaceutically acceptable salts and solvates thereof, in particular its hydrochloride, in an amount (in ramosetron) of from 0.0125 mg to 0.3 mg; tropisetron and pharmaceutically acceptable salts and solvates thereof, in particular the hydrochloride, in an amount of from 2.5 mg to 30 mg; domperidone and pharmaceutically acceptable salts and solvates thereof, in an amount (in domperidone) of from 5 mg to 60 mg; haloperidol, in an amount of from 0.5 mg to 60 mg; chlorpromazine and pharmaceutically acceptable salts and solvates thereof, in particular the hydrochloride, in an amount (in chlorpromazine) of from 12.5 mg to 600 mg; prochlorperazine and pharmaceutically acceptable salts and solvates thereof, in particular the dimaleate, in an amount (in prochlorperazine) of from 2.5 mg to 30 mg; metoclopramide and pharmaceutically acceptable salts and solvates thereof, in particular the monohydrochloride monohydrate, in an amount (in metoclopramide) of from 5 mg to 60 mg; bromopride and pharmaceutically acceptable salts and solvates, in particular the monohydrochloride and the dihydrochloride monohydrate, in an amount (in bromopride) of from 5 mg to 60 mg; clebopride and pharmaceutically acceptable salts and solvates thereof, in particular the hydrogen malate and the hydrochloride monohydrate, in an amount (in clebopride) of from 0.25 mg to 3 mg; levosulpiride, in an amount of from 12.5 mg to 600 mg; alizapride and pharmaceutically acceptable salts thereof, in particular the hydrochloride, in an amount (in alizapride) of from 25 mg to 300 mg; trimethobenzamide and pharmaceutically acceptable salts thereof such as the monohydrochloride, in an amount (in trimethobenzamide) of from 50 mg to 600 mg; meclizine (also called meclozine) and pharmaceutically acceptable salts and solvates thereof, in an amount (in meclizine) of from 6.25 mg to 300 mg; promethazine and pharmaceutically acceptable salts and solvates thereof, in particular the hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant, in an amount of from 25 mg to 300 mg.

The Component (c) of the fixed-dose combination normally is a nsPAChA selected form the group consisting of quaternary ammonium nsPAChAs, sulfonium nsPAChAs, solifenacin and pharmaceutically acceptable salts and solvates thereof, propiverine and pharmaceutically acceptable salts and solvates thereof, oxyphencyclimine and pharmaceutically acceptable salts and solvates thereof, tolterodine and pharmaceutically acceptable salts and solvates thereof, fesoterodine and pharmaceutically acceptable salts and solvates thereof and TTS-oxybutynin and pharmaceutically acceptable salts thereof.

Said nsPAChA is advantageously selected from the group consisting of nsPAChA selected from the group consisting of anisotropine pharmaceutically acceptable quaternary salts, butylscopolamine pharmaceutically acceptable salts, cimetropium pharmaceutically acceptable salts, clidinium pharmaceutically acceptable salts, fesoterodine and pharmaceutically acceptable salts thereof, glycopyrronium pharmaceutically acceptable salts, otilonium pharmaceutically acceptable salts, oxyphencyclimine and pharmaceutically acceptable salts thereof, prifinium pharmaceutically acceptable salts, propiverine and pharmaceutically acceptable salts thereof, solifenacin and pharmaceutically acceptable salts thereof, tolterodine and pharmaceutically acceptable salts thereof, timepidium pharmaceutically acceptable salts, trospium pharmaceutically acceptable salts, TTS oxybutynin; and valethamate pharmaceutically acceptable salts.

Preferably, said nsPAChA is selected from the group consisting of glycopyrronium pharmaceutically acceptable salts, in an amount that is equivalent to from 0.5 mg to 16 mg of glycopyrronium bromide; propiverine and pharmaceutically acceptable salts thereof, in an amount that is equivalent to from 7.5 mg to 240 mg of propiverine hydrobromide; solifenacin and pharmaceutically acceptable salts thereof, in an amount that is equivalent to from 5 mg to 60 mg, preferably from 5 mg to 40 mg, of solifenacin succinate; trospium pharmaceutically acceptable salts, in an amount that is equivalent to from 20 mg to 480 mg of trospium chloride; and TTS-oxybutynin, in a released amount of from 3.9 mg/24 h to 7.8 mg/24 h.

Scopolamine methobromide, scopolamine butylbromide, scopolamine methonitrate, isopropamide iodide, valethamate bromide, atropine methobromide, atropine methonitrate, diponium bromide, pipenzolate bromide, penthienate bromide, benactizine methobromide, diphemanil bromide, emeprioum bromide, dibutolinesulfate, cimetropium bromide, prifinium bromide, timepidium bromide, otilonium bromide and the compounds of formula I above such as homatropine quaternary salts, anisotropine quaternary salts, trospium quaternary salts, clidinium quaternary salts, benzilonium quaternary salts and glycopyrronium quaternary salts, especially, trospium chloride, cimetropium bromide and glycopyrronium bromide are other advantageous quaternary ammonium nsPAChAs used as Component (c) of the fixed-dose combination.

In a preferred embodiment, anisotropine methylbromide; butylscopolamine bromide; cimetropium bromide; clidinium bromide; glycopyrronium bromide; methylpropiverinium iodide; methylpropiverinium bromide; otilonium bromide; prifinium bromide; timepidium bromide; trospium chloride, succinate, maleate, fumarate or tartrate; valethamate bromide; fesoterodine and its fumarate; oxyphencyclimine and its hydrochloride; propiverine and its hydrochloride; solifenacin and its succinate; tolterodine and its L-hydrogen tartrate are soecific nsPAChAs used as Component (c).

The dose/unit form of the Component (c) may vary according to the intrinsic muscarinic cholinergic potency and to the administration route of said component. Advantageously, said dose is from 1.2-fold to 4 times, or 1.2-fold to 6-times higher than the mean maximal tolerated dose determined in the clinical trials.

The compositions of the present invention may be in unit forms, for immediate release or extended release. In such case, the MCRA Component (a) is present in an amount of from 100% to 600, preferably from 120% to 600%, the maximum amount of said MCRA contained in the IR dosage unit forms administered for the approved indication contained in the commercial products or of the maximal, single MCRA dose administered during the clinical trials of each MCRA, that is considered to be equivalent to the Maximum Tolerated Dose as determined during the clinical trials;

the non-anticholinergic antiemetic agent, Component (b) is present in an amount of from 50% to 300% of the amount of the said non-anticholinergic antiemetic agent contained as a sole active ingredient in the currently used brand or generic drugs, in particular in an amount ranging from 50% of the minimum amount to 300% of the maximum amount of said typical non-anticholinergic antiemetic agent contained in the corresponding, currently used generic or brand drug for its antiemetic indication in IR form; and the nsPAChA Component (c) is present in an amount of from 50% to 600%, preferably from 1.2-fold to 6 times the maximum IR amount of said nsPAChA contained in the currently administered IR dosage unit forms indicated in the anticholinergic therapy; more particularly, the nsPAChA is present, in an IR unit form, in an amount ranging from 50% to 400%, preferably from 120% to 400%, the maximum amount of said nsPAChA contained in the currently administered IR dosage unit forms for the treatment of the above-cited disorders or, in an ER unit form, in an amount ranging from 75% to 600%, preferably from 120% to 600%, the maximum amount of said nsPAChA contained in the currently administered unit dosage IR forms or in an amount which ranging from 75% to 400% the maximum amount of said nsPAChA contained in the currently administered unit dosage ER forms for the anticholinergic therapy.

Any one of the Components (a) may be combined with any one Component (b) and with any one Component (c) in a ternary fixed-dose combination comprising said Component (a), said Component (b) and said Component (c) in a pharmaceutical composition in dosage unit form in admixture with a pharmaceutical carrier for IR or ER administration.

In particular, the fixed-dose combination of the invention consists of a pharmaceutical composition in dosage unit form comprising or consisting essentially of (a) any of the MCRAs as illustrated in the above "The MCRAs" section, each in a pharmaceutical composition in admixture with a pharmaceutical carrier, said MCRA being preferably selected from the group consisting of AF267 and pharmaceutically acceptable salts and solvates thereof; cevimeline and pharmaceutically acceptable salts and solvates thereof; EUK 1001 and pharmaceutically acceptable salts and solvates thereof; milameline and pharmaceutically acceptable salts and solvates thereof; RS-86 and pharmaceutically acceptable salts and solvates thereof; sabcomeline and pharmaceutically acceptable salts and solvates thereof; talsaclidine and pharmaceutically acceptable salts and solvates thereof; tazomeline and pharmaceutically acceptable salts and solvates thereof; xanomeline and pharmaceutically acceptable salts and solvates thereof; AC-42 and pharmaceutically acceptable salts and solvates thereof; TBPB and pharmaceutically acceptable salts and solvates thereof; 4-Fluoro-6-methyl-1-[1-(tetrahydro-2H-pyran-4-yl)-4-piperidinyl]-1,3-dihydro-2H-benzimidazol-2-one and pharmaceutically acceptable salts and solvates thereof; 5-Fluoro-6-methyl-1-[1-(tetrahydro-2H-pyran-4-yl)-4-piperidinyl]-1,3-dihydro-2H-benzimidazol-2-one and pharmaceutically acceptable salts and solvates thereof; 4-(R)-ethyl-3-(2-methylbenzamido)-1,4'-bipiperidine-1'-carboxylate and pharmaceutically acceptable salts and solvates thereof; ethyl 3-[(3-exo)-(2-benzamidoethyl)amino]-8-azabicyclo[3.2.1]octane-8-carboxylate and pharmaceutically acceptable salts and solvates thereof; racemic 3-Methyl-5-(piperidin-3-yl)-1,2,4-oxadiazole, its enantiomers and pharmaceutically acceptable salts and solvates thereof such as S-(+)-3-methyl-5-(piperidin-3-yl)-1,2,4-oxadiazole D-tartrate and R-(−)-3-Methyl-5-(piperidin-3-yl)-1,2,4-oxadiazole L-tartrate; and MK-7622 and pharmaceutically acceptable salts and solvates thereof;

(b) any of the naAEAs as illustrated in the above "The naAEAs" section, said naAEA being preferably selected from the group consisting of alosetron and pharmaceutically acceptable salts and solvates thereof, especially its hydrochloride; azasetron and pharmaceutically acceptable salts and solvates thereof, especially its hydrochloride; ondansetron and pharmaceutically acceptable salts and solvates thereof, especially its monohydrochloride dihydrate; granisetron and pharmaceutically acceptable salts and solvates thereof, especially its hydrochloride; dolasetron and pharmaceutically acceptable salts and solvates thereof, especially its monomethanesulfonate monohydrate, ramosetron and pharmaceutically acceptable salts and solvates thereof, especially its hydrochloride; tropisetron and pharmaceutically acceptable salts and solvates thereof, especially its hydrochloride; palonosetron and pharmaceutically acceptable salts and solvates thereof, especially its hydrochloride; domperidone and pharmaceutically acceptable salts and solvates thereof, especially its maleate; metoclopramide and pharmaceutically acceptable salts and solvates thereof, especially its hydrochloride monohydrate; bromopride and pharmaceutically acceptable salts and solvates thereof, especially its monohydrochloride or the dihydrochloride monohydrate; alizapride and pharmaceutically acceptable salts and solvates thereof, especially its hydrochloride; clebopride and pharmaceutically acceptable salts and solvates thereof, especially its malate and the hydrochloride monohydrate; meclizine (meclozine) and pharmaceutically acceptable salts and solvates thereof, especially its hydrochloride monohydrate; promethazine and pharmaceutically acceptable salts and solvates thereof, especially its hydrochloride; chlorpromazine and pharmaceutically acceptable salts and solvates thereof, especially its hydrochloride; prochlorperazine and pharmaceutically acceptable salts and solvates thereof, especially its dimaleate, its dimesylate and its the 1,2-ethanedisulfonate (1:1) (edisilate); hydroxyzine and pharmaceutically acceptable salts and solvates thereof such as the dihydrochloride or the 4-[(3-carboxy-2-hydroxynaphthalen-1-yl)methyl]-3-hydroxynaphthalene-2-carboxylate (pamoate) dronabinol; nabilone; aprepitant; netupitant, rolapitant, and casopitant; and (c) any of the nsPAChAs as illustrated in the above "The nsPAChAs" section, said nsPAChA being preferably selected from the group consisting of anisotropine pharmaceutically acceptable quaternary salts, butylscopolamine pharmaceutically acceptable salts, cimetropium pharmaceutically acceptable salts, clidinium pharmaceutically acceptable salts, fesoterodine and pharmaceutically acceptable salts thereof, glycopyrronium pharmaceutically acceptable salts, otilonium pharmaceutically acceptable salts, oxyphencyclimine and pharmaceutically acceptable salts thereof, prifinium pharmaceutically acceptable salts, propiverine and pharmaceutically acceptable salts thereof, solifenacin and pharmaceutically acceptable salts thereof, tolterodine and pharmaceutically acceptable salts thereof, timepidium pharmaceutically acceptable salts, trospium pharmaceutically acceptable salts and valethamate pharmaceutically acceptable salts;

in admixture with at least one pharmaceutical carrier or vehicle.

In particular, the fixed-dose combination of the invention, according to a first aspect, consists of a pharmaceutical composition comprising or consisting essentially of (a) a MCRA selected from the group consisting of cevimeline hydrochloride hemihydrate, in an amount of from 34.5 mg to 180 mg, xanomeline, as free base, as oxalate or as L-tartrate, in an amount of from 90 mg to 450 mg, milameline hydrochloride, in an amount of from 2.4 mg to 12 mg and MK 7622, as free base, as hydrochloride, as fumarate or as methanesulfonate, in an amount selected from the group consisting of from more than 5 mg to 15 mg, from more than 15 mg to 45 mg, from more than 45 mg to 270 mg, from more than 15 mg to 225 mg, from more than 45 mg to 225 mg, and from 54 mg to 180 mg;

(b) a naAEA selected from the group consisting of selected from the group consisting of alosetron hydrochloride, in an amount (in alosetron) of from 0.25 mg to 6 mg; azasetron hydrochloride, in an amount (in azasetron) of from 5 mg to 60 mg; dolasetron mesylate, in an amount (in dolasetron) of from 25 mg to 600 mg; granisetron hydrochloride, in an amount (in granisetron) of from 0.5 mg to 6 mg; ondansetron hydrochloride dihydrate, in an amount (in ondansetron) of from 2 mg to 64 mg; palonosetron hydrochloride, in an amount (in palonosetron) of from 0.25 mg to 3 mg; ramosetron hydrochloride, in an amount (in ramosetron) of from 0.0125 mg to 0.3 mg, tropisetron hydrochloride, in an amount (in tropisetron) of from 2.5 mg to 30 mg; domperidone and pharmaceutically acceptable salts and solvates thereof, in an amount (in domperidone) of from 5 mg to 60 mg; haloperidol, in an amount of from 0.5 mg to 60 mg; chlorpromazine hydrochloride, in an amount (in chlorpromazine) of from 12.5 mg to 600 mg; prochlorperazine dimaleate, in an amount (in prochlorperazine) of from 2.5 mg to 30 mg; metoclopramide monohydrochloride monohydrate, in an amount (in metoclopramide) of from 5 mg to 60 mg; bromopride monohydrochloride or dihydrochloride monohydrate, in an amount (in bromopride) of from 5 mg to 60 mg; clebopride hydrogen malate or hydrochloride monohydrate, in an amount (in clebopride) of from 0.25 mg to 3 mg; levosulpiride, in an amount of from 12.5 mg to 600 mg; alizapride hydrochloride, in an amount (in alizapride) of from 25 mg to 300 mg; trimethobenzamide monohydrochloride, in an amount (in trimethobenzamide) of from 50 mg to 600 mg; meclizine (also called meclozine) and pharmaceutically acceptable salts and solvates thereof, in an amount (in meclizine) of from 6.25 mg to 300 mg; promethazine hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant, in an amount of from 25 mg to 300 mg; and (c) a nsPAChA selected from the group consisting of glycopyrronium pharmaceutically acceptable salts, in an amount that is equivalent to from 0.5 mg to 16 mg of glycopyrronium bromide; propiverine and pharmaceutically acceptable salts thereof, in an amount that is equivalent to from 7.5 mg to 240 mg of propiverine hydrobromide; solifenacin and pharmaceutically acceptable salts thereof, in an amount that is equivalent to from 5 mg to 60 mg, preferably from 5 mg to 40 mg, of solifenacin succinate; trospium pharmaceutically acceptable salts, in an amount that is equivalent to from 20 mg to 480 mg of trospium chloride; and TTS-oxybutynin, in a released amount of from 3.9 mg/24 h to 7.8 mg/24 h, in admixture with a pharmaceutical carrier or vehicle.

According to a second aspect, in the above fixed-dose combination Component (c) is selected from the group consisting of anisotropine methylbromide, in an amount of from 25 mg to 300 mg, normally from 60 mg to 200 mg; butylscopolamine bromide in an amount of from 5 mg to 60 mg, normally from 12 mg to 40 mg; cimetropium bromide, in an amount of from 25 mg to 200 mg; clidinium bromide in an amount of from 1.25 mg to 15 mg, normally from 3 mg to 104-2 mg; fesoterodine fumarate, in an amount of from 4 mg to 48 mg, normally from 9.6 mg to 32 mg; glycopyrronium bromide in an amount of from 1 mg to 12 mg, normally from 2.2 to 8 mg; otilonium bromide in an amount of from 20 mg to 240 mg, normally from 48 mg to 160 mg; prifinium bromide in an amount of from 15 mg to 180 mg, normally from 36 mg to 120 mg; propiverine hydrochloride, in an amount of from 7.5 mg to 180 mg, normally from 18 mg to 120 mg; solifenacin succinate, in an amount of from 5 mg to 60 mg, normally from 12 mg to 25 mg or 21 mg; tolterodine tartrate, in an amount of from 1 mg to 16 mg, normally from 4.8 mg to 16 mg; timepidium bromide in an amount of from 7.5 mg to 180 mg, normally from 36 mg to 120 mgr; trospium chloride, in an amount of from 24 mg to 480 mg; TTS-oxybutynin, as a patch releasing from 3.9 mg/24 h to 7.8 mg/24 h, advantageously from 3.9 mg/24 h to 5.85 mg/24 h, normally 3.9 mg/24 h oxybutynin; and valethamate bromide in an amount of from 5 mg to 60 mg, normally from 12 mg to 40 mg.

According to a further embodiment, a particularly advantageous fixed-dose combination consists of a pharmaceutical dosage unit form comprising or consisting essentially of
(a) xanomeline; and
(b) granisetron; and
(c) oxybutynin
in admixture with at least one pharmaceutical carrier or vehicle, in a formulation in a patch for transdermal administration.

More advantageously, the above patch releases xanomeline an amount/24 hours giving xanomeline plasma concentrations in human of from 16.572 ng/ml to 78.6 ng/ml; granisetron, in an amount of from 1.5 mg/24 h to 5 mg/24 h; and oxybutynin, in an amount of from 3.9 mg/24 h to 5.85 mg/24 h.

Preferably, said patch releases amount/24 hours giving xanomeline plasma concentrations in human of from 16.572 ng/ml to 78.6 ng/ml; granisetron, in an amount of from 1.5 mg/24 h to 3 mg/24 h; and oxybutynin, in an amount of from 3.9 mg/24 h.

In all of these fixed-combinations, solifenacin succinate is preferably present as Component (c) in an amount selected from the group consisting of from 5 mg to 60 mg, from 10 mg to 40 mg, from 12 mg to 30 mg, from 12 mg to 25 mg and of 21 mg.

According to the present invention, each of the above fixed-dose combinations may include, as a further component (d), an AChEI also formulated in a pharmaceutical composition, said AChEI being selected from the group consisting of 1,2,3,4-tetrahydro-9-acridinamine (tacrine) and pharmaceutically acceptable salts and solvates thereof, (±)-2,3-dihydro-5,6-dimethoxy-2-[[1-(phenylmethyl)-4-piperidinyl]methyl]-1H-inden-1-one (donepezil) and pharmaceutically acceptable salt and solvates thereof, (S)—N-Ethyl-N-methyl-3-[1-(dimethylamino)ethyl]-phenyl carbamate (rivastigmine) and pharmaceutically acceptable salts and solvates thereof, 4aS,6R,8aS-3-methoxy-11-methyl-4a,5,9,10,11,12-hexahydroxy-6H-benzofuro[3a,3,2-e,f]benzazepin-6-ol (galantamine) and pharmaceutically acceptable salts and solvates thereof.

The above fixed-dose combinations and any of the pharmaceutical compositions that are part of the above combinations and kits are formulated with pharmaceutical carriers, diluents, vehicles and devices according to known and conventional methods and/or technologies in the art and as illustrated in the "The Formulations" section below. In addition, any of the above fixed-dose combinations and any of the above pharmaceutical compositions may further include a component (d) an AChEI.

The AChEI Component (d) when included in the combination with Component (a), Component (b) and/or Component (c) as described herein, may be present in an amount of from about 100% to about 1000% of a recommended dose of Component (d) contained in a unit form used for the treatment of Alzheimer type dementia.

Among the preferred AChEIs, in the fixed-dose combinations of the present invention, donepezil hydrochloride is present at a dose of from 5 mg to 98 mg, advantageously from 10 mg to 98 mg, preferably from 15 mg to 69 mg, normally from 15 mg to 60 mg; rivastigmine, as hydrogen tartrate, is present, in a composition for oral administration, at a dose, in rivastigmine, of from 1.5 mg to 30 mg, advantageously from 6 mg to 30 mg, preferably from 9 mg to 24 mg, normally from 9 mg to 18 mg; rivastigmine, as the free base, is present in patch releasing from 4.6 mg/24 h to 52 mg/24 h, advantageously from 9.6 mg/24 h to 39.9 mg/24 h, normally from 13.3 mg/24 h to 39.9 mg/24 h or from 4.6 mg/24 h to 13.3 mg/24 h rivastigmine; and galantamine, as hydrobromide, is present in an amount of from 4 mg to 96 mg, advantageously from 12 mg to 96 mg, normally from 18 mg to 48 mg.

The Formulations

The unit form of the present invention may be a tablet, a capsule, a pre-measured volume of a liquid solution or suspension for oral administration or a TTS as a gel or patch, including spray patches, for transdermal application. In said unit form the nsPAChA and the MCRA, as free base are as a pharmaceutically acceptable salt or solvate thereof, may be mixed together or separated according to known technologies in admixture with a pharmaceutical carrier in a pharmaceutical composition.

Component (a), Component (b) and Component (c) are formulated with conventional pharmaceutical carriers in known formulations for oral use wherein said components are mixed together or separated, for example in two or three tablets introduced in a capsule or in a two-compartment capsule, wherein one of the Components (a), (b) and (c), is in a first of the two compartments and the two other Components and the second of the two compartments, or in a multilayer (di-layer or tri-layer) tablet wherein the three components are all in IR or in ER form or one or two Components is in IR form and the other(s) is/are in ER form, according to known technologies. Component (d) may be optionally included in the first or second compartment, or optionally included in a multilayer tablet as described herein above, with one or more of Components (a), (b) and (c).

The pharmaceutical carriers and vehicles are those commonly used for the preparation of compositions for oral, buccal, including sublingual, and parenteral, in particular transdermal, administration. Appropriate unit forms comprise the oral forms such as tablets, including orodispersible tablets and orosoluble tablets, soft or hard gelatin capsules, powders or granulates in sachets and suitably measured oral solutions or suspensions as well as transdermal therapeutic systems such as patches for transdermal administration.

Component (a), Component (b) and Component (c) may also be present in form of one of their complexes with a cyclodextrin, for example α-cyclodextrin, β-cyclodextrin, γ-cyclodextrin, 2-hydroxypropyl-β-cyclodextrin or methyl-β-cyclodextrin.

Component (a), Component (b) and Component (c), with optionally a further Component (d), may also be formulated in the form of microcapsules, optionally with one or more carriers or additives.

For oral administration, Component (a), Component (b) and Component (c), with optionally a further Component (d), together or separately, are formulated by mixing the active ingredient with conventional pharmaceutical acceptable carriers enabling said active ingredients to be formulated in tablets, dragees, orally disintegrating tablets, capsules, liquid solutions or suspensions, syrups and the like.

Carriers for IR tablets may include, but are not limited to, starches, cellulose and derivatives thereof; lubricants such as talc, stearic acid or magnesium stearate; diluents such as talc, powdered cellulose, lactose, starches such as maize or corn starch, mannitol, sorbitol; disaggregating agents such as microcrystalline cellulose or crospovidone; lubricants such as polyethylene glycol or magnesium stearate; ligands such as methylcellulose, sodium carboxymethylcellulose, alginic acid, alginates; sweeteners, such as sucrose, dextrose, mannitol, saccharin; or flavoring agents such as natural or synthetic oils.

Carriers for orally disintegrating tablets may include, but are not limited to, lubricants, aggregating, sweetening, flavoring or disaggregating agents as well as agents improving the buccal mucosa absorption of Component (a), Component (b) and Component (c) such as sorbitol, mannitol, lactose and cellulose.

Carriers for liquid, normally aqueous, suspensions or solutions may include, but are not limited to, antioxidants, such as sodium metabisulfite or sodium sulfite, thickening agents, such as microcrystalline cellulose, hydroxypropylcellulose, carboxymethylcellulose or polyvinylpyrrolidone, preservatives such as methyl paraben, ethyl paraben, sodium ethylenediaminotetracetate, sodium benzoate or an alkaline salt of sorbic acid, as well as flavoring and sweetening agents.

The sweeteners contained in the orally disintegrating tablets and the liquid suspensions or solutions may be natural, optional reduced sugars such as sucrose, dextrose, xylitol, mannitol or sorbitol, or synthetic product such as sodium saccharine or aspartame.

The flavoring agents are pharmaceutically acceptable flavors and tastes of synthetic and natural oils, the latter extracted from plants, leaves, flowers, fruits and their combinations, which include, but are not limited to, cinnamon, peppermint, anise and citron leaves, bitter almond, or citrus fruits, in particular orange and/or lemon, linden and grapefruit oils. Also chocolate, vanilla or eucalyptus flavor and essences of fruit, in particular apple, pear, peach, strawberry, cherry, apricot, orange, lemon and/or grapes may be advantageously used.

The composition according to the present invention may be in form of a capsule containing two tablets as described herein above, one of them comprising Component (a), and the other comprising Component (b) and Component (c) in admixture with each other and with a pharmaceutical carrier. The unit form may also be a capsule containing two tablets as described herein above, one of them comprising Component (b), and the other comprising Component (a) and Component (c) in admixture with each other and with a pharmaceutical carrier. The unit form may also be a capsule containing two tablets as described herein above, one of them comprising Component (c), and the other comprising Component (a) and Component (b) in admixture each other and with a pharmaceutical carrier.

The unit form may also be a capsule containing three tablets as described herein above, one of them comprising Component (a), the second comprising Component (a) and the third comprising Component (c) in admixture with each other and with a pharmaceutical carrier. Component (d) may be optionally included in the composition as described herein above, with one or more of Components (a), (b) and (c).

The combination may be formulated in tablets in which one or both of the two components is in controlled-release formulation, for example as a dispersion of said component in hydroxypropylmethyl cellulose or in a film-coated microgranule. Advantageously, the MCRA, in an ER-formulation is in the core and the nsPAChA and the naAEA, in IR-formulation, are in the outer layer in multi-layer tablets in which, for example, both the core and the outer layers are coated with a film. Analogously, capsules made of two separated compartments, one containing Component (a), in IR- or ER-formulation and the other containing Component (b) and Component (c), in ER- or, preferably, in IR formulation, may be used. Component (d) may be optionally included in the combination as described herein above, with one or more of Components (a), (b) and (c).

Carriers and vehicles for ER tablets may include, but are not limited to, retardant materials such as acrylic and methacrylic acid polymers and copolymers; cellulose derivatives such as hydroxypropylmethylcellulose, hydroxyethylcellulose, hydroxypropylethylcellulose, hydroxypropylcellulose, methylcellulose, ethylcellulose, or sodium carboxymethylcellulose; gums; waxes; glycerides or aliphatic alcohols or a mixture thereof.

Component (a), Component (b) and Component (c), with optionally a further Component (d), as the base thereof or as a pharmaceutically acceptable salt thereof, may also be formulated, together or separately in any TTS such as a patch, a gel, a cream, a spray, an ointment, a lotion or a paste. Advantageously, in said TTS, Component (a) or Component (b) or Component (c) is present in admixture with the common diluents and permeation enhancers for the TTS administration; or Component (a) and Component (c) are both present in admixture with the common diluents and permeation enhancers for the TTS administration; or the Component (a) and Component (c) are both present in admixture with the common diluents and permeation enhancers, or Component (a), Component (b) and Component (c) are altogether present in admixture with the common diluents and permeation enhancers. Component (d) may be optionally included in the TTS as described herein above, with one or more of Components (a), (b) and (c).

The permeation enhancer may be any compound which allows the improved permeation of drugs through the skin (see for example the review in Pharmaceutical Technology, November 1997, pages 58-66, the disclosure of which is herein incorporated by reference in its entirety). Such substances may include, but are not limited to, be lower ($C_1$-$C_4$) alkanols; fatty alcohols such as lauryl alcohol (dodecanol), alone or in combination with a lower alkanol; fatty acids such as linolenic acid or oleic acid; fatty acid esters such as isopropyl palmitate, stearate, linoleate, oleate or myristate; glycerol; glycerol monoesters such as glycerol monostearate, monolinoleate or monooleate; glycerol diesters; glycerol triesters such as triacetin; sucrose monostearate, monolinoleate or monooleate; sorbitan esters; fatty alcohol ethers having from 10 to 20 carbon atoms; glycols, such as diethylene glycol or propylene glycol; or glycols lower alkyl ethers, such as diethylene glycol mono($C_2$-$C_4$)alkyl ether, in particular diethylene glycol monoethyl ether.

These permeation enhancers are present in an amount from 0.01 to 20% by weight of the total weight of the composition, advantageously in an amount of from 0.05 to 10% by weight, preferably from 0.1 to 5% by weight.

The oxybutynin TTS for use according to the present invention may be in any oxybutynin delivering transdermal pharmaceutical form, such as a patch, a gel, a cream, a spray, an ointment, a lotion or a paste, wherein oxybutynin is present in admixture with the common diluents and permeation enhancers, said pharmaceutical form containing oxybutynin base or a pharmaceutically acceptable salt thereof, such as its hydrochloride, hydrobromide, sulfate, phosphate, mesilate, acetate, maleate, succinate, lactate, citrate, hydrogen tartrate, tartrate, napsilate or embonate.

Appropriate permeation enhancers are for example the aforementioned ones, and are present in an amount from 0.01 to 20% by weight of the total weight of the composition, advantageously in an amount of from 0.05 to 10% by weight, preferably from 0.1 to 5% by weight.

Advantageously, the oxybutynin TTS is a patch releasing 3.9-5.85 mg/day of oxybutynin, administered in combination, for example, with oral ondansetron (as hydrochloride dihydrate) and a MCRA. Another advantageous combination is an oxybutynin patch delivering 3.9 mg/day of oxybutynin and an oral or transdermal granisetron (as the freebase or as hydrochloride), at a dose of from 1 mg to 3.1 mg and with a MCRA. A routine treatment can be made with a combination of an oxybutynin patch delivering 3.9 mg/day of oxybutynin and an oral ondansetron (as hydrochloride dihydrate, at a dose of from 8 mg to 32 mg and a MCRA. In particular, a TTS consisting of a patch is obtained as described for example in U.S. Pat. Nos. 5,212,199, 5,227,169, 5,747,065, 6,743,441, 7,081,249, 7,081,250, 7,081,251, 7,081,252, 7,087,241, US 2004/0057985 U.S. Pat. No. 8,420,117, US 2014/0271796, U.S. Pat. Nos. 8,802,134, 8,877,235, the disclosures of which are each incorporated herein by reference in their entirety.

Typically, a TTS in form of a patch is manufactured by mixing a predetermined amount of oxybutynin, of rivastigmine or of an association of the two drugs with the aforementioned permeation enhancer in a laminated composite which basically contains at least one reservoir comprising a adhesive which is a pressure-sensitive adhesive suitable for the contact with the skin, a backing layer and a strip to be removed just before the application of the patch on the subject's skin. The oxybutynin TTS may be manufactured according to one of the methods illustrated in the above-cited patent documents.

Use

As set forth herein, Component (a), Component (b) and Component (c) may be administered concurrently or sequentially to a patient suffering from a hypocholinergic disorder of the CNS such as Alzheimer type dementia and schizophrenia. In particular, Component (a), Component (b) and Component (c) can be administered in a specific dosage regimen as illustrated above—to treat Alzheimer type dementia and schizophrenia, Component (a), Component (b) and Component (c) being administered simultaneously or sequentially to one another, in each case by the same or different administration route.

By the combination of Component (a), Component (b) and Component (c) such as in the same unit form, Component (b) and Component (c) act synergistically to allow for the safe administration of high doses of Component (a) without dangerous adverse effects linked to the peripheral cholinergic action of said Component (a). Accordingly,
the therapeutic efficacy of Component (a) to safely improve cognition of patients suffering from a hypocholinergic disorder of the CNS such as Alzheimer type dementia or schizophrenia is enhanced, due to the synergistic antiemetic/peripheral anticholinergic action of Component (b) and Component (c).

Thus, the present invention in one aspect, provides a combination comprising or consisting essentially of, as Components:
(a) a muscarinic cholinergic receptor agonists (MCRA); and
(b) a non-anticholinergic antiemetic agent
(c) a non-selective, peripheral anticholinergic agents (nsPAChAs) for use in the treatment of a hypocholinergic disorder of the CNS.

The nsPAChA used as Component (a), their properties and doses are described in the "nsPAChAs" section above.

The MCRAs used as Component (b), their properties and doses are described in the "MCRAs" section above.

For use, Component (a), Component (b) and Component (c), together or separately, are formulated in pharmaceutical compositions prepared as described in the "Formulation" section above.

The present invention, in another aspect, provides a method for treating a hypocholinergic disorder of the CNS, which comprises administering to a patient in need of said treatment a combination comprising or consisting essentially of, as Components:
(a) a muscarinic cholinergic receptor agonists (MCRA); and
(b) a non-anticholinergic antiemetic agent
(c) a non-selective, peripheral anticholinergic agents (nsPAChAs).

The method is carried out by administering Component (a), Component (b) and Component (c) of said combination concurrently, or sequentially. Component (a), Component (b) and Component (c) may be independently administered by oral or parenteral route, in particular by intramuscular or intravenous injection or by transdermal administration by a TTS such as a gel or a patch.

The MCRAs used as Component (a), their properties and doses are described in the "MCRAs" section above.

The naAEA used as Component (b), their properties and doses are described in the "naAEAs section" above.

The nsPAChA used as Component (c), their properties and doses are described in the "nsPAChAs section" above.

For administering the combination to said patient, Component (a), Component (b) and Component (c), together or separately, are formulated in pharmaceutical compositions prepared as described in the "Formulation" section above.

In the case of simultaneous administration of the three components, Component (a), Component (b) and Component (c), in admixture with a pharmaceutical carrier or vehicle, may be associated in the same pharmaceutical composition, formulated as described in "The Formulations" section above, in a unit dose for oral or parenteral, including transdermal, route, according to known or conventional methods or technologies in the art.

The doses of the above dose-ranges are given in order to present the possibility of manufacturing pharmaceutical compositions and of administering said doses in said pharmaceutical composition. However, the discovery of the beneficial competitive antagonist/agonist action of the nsPAChA and of the MCRA, combined with a nsPAChA/naAEA synergism, enables the full efficacy of the MCRA.

Example 1

Study 1—Establishment of the Dose-Response to Xanomeline in a Mouse Model of Diarrhea Male Swiss mice (4-6 weeks old), N=10 per treatment group were used, and treated intra-peritoneally (i.p.) with either vehicle (vehicle group) or increasing doses of xanomeline, a representative muscarinic agonist. Mice were randomly assigned to one of two experimental groups (vehicle; or increasing doses of xanomeline). Each animal was identified by its group name, cage number, series (day) of experiment, and number (1 to 10) written with permanent ink on the tail.

Mice were placed individually in cages without any bedding materials. During the experiment the number of fecal pellets were counted at different time-points, starting one hour before the time of the administration of the test compound (T0), as outlined below:
T−1 h to T0: counting of the accumulated fecal pellets excreted.
T0: administration of the test compound,
T0 to T+2 h: counting of the accumulated fecal pellets excreted.
T+2 h to T+4 h: counting of the accumulated fecal pellets excreted.

The total number of fecal pellets for each mouse was counted over time. An analysis of variance (ANOVA) was performed on the results. Fisher's Protected Least Significant Difference was used for pairwise comparisons; p values ≤0.05 were considered significant. Grubbs' test (http://www.graphpad.com/quickcs/Grubbs1.cfm) was used to detect outliers for each parameter in each experimental group.

Results confirmed that xanomeline i.p. (0.3 to 30 mg/kg) dose-dependently causes diarrhea.

Study 2—Antagonism of Xanomeline-Induced Diarrhea in Mice by Oxybutynin

Male Swiss mice (4-6 weeks old), N=10 per treatment group were used. Animals were pretreated with i.p. oxybutynin (a representative peripheral muscarinic receptor antagonist) or vehicle; 30 minutes later animals were treated with xanomeline at a dose of 30 mg/kg that caused diarrhea (as determined in Experiment 1). The dose of oxybutynin ordinarily ranged from 0.3 to 30 mg/kg.

Mice were placed individually in cages without any bedding materials. During the experiment the number of fecal pellets was counted at different time-points as outlined below:
T−1 h to T0: counting of the accumulated fecal pellets excreted.
T0: administration of oxybutinin.
T30 min: administration of vehicle or xanomeline.
T 30 min to T 2.5 h: counting of accumulated fecal pellets excreted.
T+2.5 h to T+4.5 h: counting of accumulated fecal pellets excreted.

The total number of fecal pellets for each mouse was counted over time. An analysis of variance (ANOVA) was performed on the results. Fisher's Protected Least Significant Difference was used for pairwise comparisons. The p value ≤0.05 were considered significant. Grubbs' test (http//www atgraphpad.com/quickcalcs/Grubbs1.cfm) was used to detect outliers for each parameter in each experimental group.

Results showed that oxybutynin dose-dependently antagonized the diarrhea induced by xanomeline, thus confirming that the representative nsPAChA oxybutynin suppresses the adverse effects of the representative muscarinic antagonist xanomeline.

Example 2

Evaluation of Cognition with Oxybutynin and Xanomeline in the T-Maze Alternation Task in Mice The T-maze continuous alternation task (T-CAT) is useful as model for studying compounds with cognitive enhancing properties. The T-maze consists of 2 choice arms and 1 start arm mounted to a square center. Manual doors are provided to close specific arms during the force choice alternation task.

Male Swiss mice (4-6 weeks old), N=10 per treatment group were used, and were pretreated with:

Oxybutynin at the dose that blocked fecal pellet excretion in Study 2 of Example 1. Thirty minutes later mice were treated with either vehicle or one of 4 doses of xanomeline:

the highest dose that did not cause diarrhea;

a dose that caused diarrhea.

Mice were randomly assigned to one of the different experimental treatment groups. Each animal was identified by its group name, cage number, series (day) of experiment, and number (1 to 10) written with permanent ink on the tail.

The T-maze apparatus is made of gray Plexiglas with a main stem (55 cm long×10 cm wide×20 cm high) and two arms (30 cm long×10 cm wide×20 cm high) positioned at 90 degree angle relative to the main stem. A start box (15 cm long×10 cm wide) is separated from the main stem by a guillotine door. Horizontal doors are also provided to close specific arms during the force choice alternation task.

The experimental protocol consisted of one single session, which started with 1 "forced-choice" trial, followed by 14 "free-choice" trials. In the first "forced-choice" trial, animals were confined for 5 seconds to the start arm and then were released while either the left or the right goal arm was blocked by the horizontal door. Animals then negotiated the maze, eventually entering the open goal arm, and returned to the start position. Immediately after the return of the animals to the start position, the left or right goal door was opened and the animals were allowed to choose freely between the left and right goal arm ("free choice trials). An animal was considered as having entered in arm when it placed its four paws in the arm. A session was terminated and animals were removed from the maze as soon as 14 free-choice trials had been performed or 10 min had elapsed, whichever event occurred first.

The apparatus was cleaned between each animal using 40% ethanol. Urine and feces were removed from the maze. During the trials, animal handling and the visibility of the operator was minimized as much as possible.

The percentage of alternation over the 14 free-choice trials was determined for each mouse and was used as an index of working memory performance. This percentage is defined as entry in a different arm of the T-maze over successive trials (i.e., left-right-left-right, etc).

Analysis of variance (ANOVA) was performed on the results. Fisher's Protected Least Significant Difference was used for pairwise comparisons; p values ≤0.05 were considered significant. The drug-induced improvement of memory was calculated by setting the respective response of the saline/vehicle as 100% and that of the test group as 0% reversion. Grubbs' test (http://www.graphpad.com/quickcalcs/Grubbs1.cfm) was used to detect outliers for each parameter in each experimental group.

Results showed a dose-dependent increase in performance in the T-maze in animals treated with i.p. xanomeline. At the higher dose, however, animals were too sick to perform the test. Pretreatment with i.p. oxybutynin restored the animals' ability to perform the T-maze test.

The invention claimed is:

1. A pharmaceutical combination comprising as Components:
(a) a muscarinic cholinergic receptor agonist (MCRA)
(b) a non-anticholinergic antiemetic agent (naAEA); and
(c) a muscarinic receptor antagonist selected from the group consisting of the non-selective, peripheral anticholinergic agents (nsPAChAs);
wherein said MCRA Component (a) is selected from the group consisting of cevimeline and pharmaceutically acceptable salts thereof, milameline and pharmaceutically acceptable salts thereof; xanomeline and pharmaceutically acceptable salts thereof, and MK-7622 and pharmaceutically acceptable salts thereof; said naAEA Component (b) is selected from the group consisting of ondansetron and pharmaceutically acceptable salts and solvates thereof, domperidone and pharmaceutically acceptable salts and solvates thereof and metoclopramide and pharmaceutically acceptable salt and solvates thereof; and said nsPAChA Component (c) is oxybutynin in a transdermal patch.

2. The combination of claim 1, wherein said MCRA Component (a) is selected from the group consisting of cevimeline and pharmaceutically acceptable salts thereof, in an amount (in cevimeline) of from 34.5 mg to 180 mg; milameline and pharmaceutically acceptable salts thereof, in an amount (in milameline) of from 2.4 mg to 12 mg; xanomeline and pharmaceutically acceptable salts thereof, in an amount (in xanomeline) of from 90 mg to 450 mg; and MK-7622 and pharmaceutically acceptable salts thereof, in an amount (in MK-7622) of from from 5 mg to 270 mg; in a pharmaceutical composition in admixture with a pharmaceutical carrier; said naAEA Component (b) is selected from the group consisting of ondansetron and pharmaceutically acceptable salts and solvates thereof, in an amount (in ondansetron) of from 4 mg to 64 mg, domperidone and pharmaceutically acceptable salts and solvates thereof, in an amount, in domperidone of from 5 mg to 30 mg; and metoclopramide and pharmaceutically acceptable salts and solvates thereof, in an amount (in metoclopramide) of from 5 mg to 30 mg; in a pharmaceutical composition in admixture with a pharmaceutical carrier; and said nsPAChA Component (c) is oxybutynin in admixture with a pharmaceutical carrier or vehicle in a transdermal patch releasing from 3.9 mg/24 h to 7.8 mg/24 h oxybutynin.

3. The combination of claim 2, wherein said MCRA Component (a) is cevimeline or a pharmaceutically acceptable salt thereof; said naAEA Component (b) is ondansetron or a pharmaceutically acceptable salt thereof; and (c) said nsPAChA is oxybutynin in a transdermal patch releasing 3.9 mg/24 h oxybutynin.

* * * * *